(12) United States Patent
Doudna et al.

(10) Patent No.: US 11,118,194 B2
(45) Date of Patent: Sep. 14, 2021

(54) MODIFIED SITE-DIRECTED MODIFYING POLYPEPTIDES AND METHODS OF USE THEREOF

(71) Applicants: The Regents of the University of California, Oakland, CA (US); F. Hoffmann-La Roche AG, Basel (CH)

(72) Inventors: Jennifer A. Doudna, Berkeley, CA (US); Brett T. Staahl, San Francisco, CA (US); Anirvan Ghosh, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 414 days.

(21) Appl. No.: 16/061,291

(22) PCT Filed: Dec. 15, 2016

(86) PCT No.: PCT/US2016/067040
§ 371 (c)(1),
(2) Date: Jun. 11, 2018

(87) PCT Pub. No.: WO2017/106569
PCT Pub. Date: Jun. 22, 2017

(65) Prior Publication Data
US 2018/0363009 A1 Dec. 20, 2018

Related U.S. Application Data

(60) Provisional application No. 62/269,755, filed on Dec. 18, 2015.

(51) Int. Cl.
*C12N 9/22* (2006.01)
*C12P 21/02* (2006.01)
*C12N 15/90* (2006.01)
*C12P 19/34* (2006.01)

(52) U.S. Cl.
CPC ............ *C12N 15/907* (2013.01); *C12N 9/22* (2013.01); *C12N 15/90* (2013.01); *C12P 19/34* (2013.01); *C12P 21/02* (2013.01); *C07K 2319/09* (2013.01); *C12N 2310/20* (2017.05)

(58) Field of Classification Search
CPC ...... C07K 14/47; C12N 15/113; C12N 15/10; C12N 15/90; C12N 15/63; C12N 9/22; C12N 9/16
See application file for complete search history.

(56) References Cited

U.S. PATENT DOCUMENTS

| 9,834,791 B2 * | 12/2017 | Zhang ................. C12N 15/902 |
| 10,323,073 B2 * | 6/2019 | Tremblay ................ A61P 9/00 |
| 2010/0267928 A1 * | 10/2010 | Heckl .................... A61K 51/08 530/325 |
| 2014/0227787 A1 | 8/2014 | Zhang |

FOREIGN PATENT DOCUMENTS

| WO | WO 2013/176772 | 3/2013 |
| WO | WO 2014/093712 | 6/2014 |
| WO | WO 2014/204725 | 12/2014 |
| WO | WO 2015/139139 | 9/2015 |

OTHER PUBLICATIONS

Hsu, et al.; "Development and Applications of CRISPR-Cas9 for Genome Engineering"; Cell; vol. 157, No. 6, pp. 1262-1278 (Jun. 5, 2014).
Staahl, et al.; "Efficient genome editing in the mouse brain by local delivery of engineered Cas9 ribonucleoprotein complexes"; Nature Biotechnology; vol. 35, No. 5, 7 pages (May 2017).
Zetsche, et al.; "Cpf1 is a single RNA-guided endonuclease of a Class 2 CRISPRCas system"; Cell; vol. 163, No. 3, pp. 759-771 (Oct. 22, 2015).

* cited by examiner

*Primary Examiner* — Maryam Monshipouri
(74) *Attorney, Agent, or Firm* — Bozicevic, Field & Francis LLP; Paula A. Borden

(57) ABSTRACT

The present disclosure provides modified site-directed modifying polypeptides, and ribonucleoproteins comprising the modified polypeptides. The modified site-directed modifying polypeptides are modified for passive entry into target cells. The modified site-directed modifying polypeptides are useful in a variety of methods for target nucleic acid modification, which methods are also provided.

13 Claims, 62 Drawing Sheets
Specification includes a Sequence Listing.

FIG. 1A

PKKKRKV

VSRKRPRP

EGAPPAKRAR

PPQPKKKPLDGE

QRKRQK

EEKRKR

RPAATKKAGQAKKKKLD

AVKRPAATKKAGQAKKKKLD

AVKRPAATKKAGQAKKK

KRPAATKKAGQAKKKKLD

YRKCLQAGMNLEARKTKKKIKGIQQATA

MSPKRIAKRRSPPADAIPKSKKVKVSHR

MPKTRRRPRRSQRKRPPT

RQARRNRRRRWR

SKCLGWLWG

VHSHKKKKIRTSPTFTTPKTLRLRRQPKYPR-KSAPRRNKLDHY

NQSSNFGPMKGGNFGGRSSGPYGGGGQYFAKPRNQGGY

RSSINDKIIELKDLVMGTDAKMHKSGVLRKAIDYIKYLQQVNHKLRQENMVLKLANQK
NKL

PAAKRVKLD

KRKGSQMVLLERKKLKA

KRKNKKDLSTNQRALRR

KRKTKKDISNNQRSLRR

FIG. 1B

KRQHDNGNNHENSQKKR

KKLTKKQLKAQQFRKSK

KRHSQNDHSHSGRNKRR

KKWCDEYFYITHRKETR

KKNQEKSDQNETSKKRK

RKKLQDAREYKIGKERK

RKRDSENEEESEGTKKR

KRPHDDDGSSEKKKKKK

KRPQLGEIPNPMKKHKP

RKDHLRASTIMQKRAEK

KRKRGTSSGSEKKKIER

KRNRNGKDANSQNRKKF

RKGRPSTTCGHCKELRR

KKLKMIMMSNKQKKLYK

KKKHKKHKKHKKDKKKD

KKKAQNRAAQKAFRERK

RRAASSSGSVPPTLKKK

KKNNNTRTSSVRSKRRR

RKDFQNNSILRNSMKRK

KKSVPPPRMMVTRSMKR

RKEQLDKFEVKQKKRAG

RRERRTARRKDERKQEK

KRKNLDARHETVKRSKS

KRPYNTRNYGHDDKKFK

FIG. 1C

KKEKKEKKDKKEKKEKK

KKRKLEDDDEEKKEKKE

KKPSKEDSFSKYTRRRR

RRLKKIKSKTYRKIKKK

KRQLPTYEAASTRKYFK

KRLSSQNVNYDLKRRKI

KRFLLLFSFLKRNQKKK

KKAGRGNAKGIQGRKIK

RRRRDTQQVELRKAKRD

KRDSPSENEEKPNKRFK

KKDSKDKNEPLAKRTRH

RKGGRKPSLTPPKNKRA

RRLLAKDAMIAQRSKKI

RKRLNLPSEISHRKVR

KKRKIKDPRSTKARKSK

KRKRDDDEDSKDSKKAK

KKPKLEEVDEEEEKKPK

KRLDTPSRYLLRKARR

KKRKAQPLKNPKKSLKR

RKHKFDTSTWALPNKRR

KRELSSSKKEEAKREKE

KKLSTSLGGPSNGGKRK

KKRKQAKLLLKEKNRKQ

KRPISTIVEQELPKKFK

FIG. 1D

KKEKEKEKKEKEKQKKK

KKNNSERDKRTEKLKKI

RKNDAEAKRLRMEERKR

KRLRNLHffiLNCKYKSK

KKSTSVNVSDGKIKRRD

RKFKKDEHIAKLKKIGR

KKYDTKYLSGIAKRLNK

KRKGSQMVFLERKKLKA

KKDRLGDVLATAQRIRR

RRKREFHNAVERRRREL

RRKERSVSLFEIRTKEK

KKVMPAIVVRQAKSWRR

KKQNWSHMSRAQRAKLR

RRSQGRIKANEFEKKFK

KRSATGAKRAQFRKKRK

RRSSSSSQISPEHRKKS

KKPTSLKNKKDKQGKKK

KKMLPQAERERffiREKR

KKLYGDVSEVHERHRHR

KKKQGNHDRLGGYQRKK

RRGTYYMMQSRLRRERR

KRQREYYLMEQLKGIKR

RKTSELNRRKMLRKQKI

FIG. 1E

RKNIQNQSSRIATKIKR

KKDA NKAVTLKSGKK

KKHTESTASGIIKSIKK

KKLRKHARSREKRKHEK

KKPAAKKTSTSVDGKKR

KRVTIQKKDIKLARRLR

RKKASHACDQCRRKRIK

KRRMVSDLPPPSKKKAL

KRENNESRIVVLKYSKK

RRAYLHYIPKYNRYEKR

KKIKSLNAKQWKINKKR

KKKHKKDKKKAKKAKKA

KKDEKDTISSKKKRKLD

KKKTSKKVHKDRSKKSK

RRSKNSSTNTNADTKKR

KRLKLEESDKNnEKGKK

RKKGIRKFTPSMQRRLK

KKRTTRRKKDPNAPKRR

KKHYNNSKARRERKSGK

RKTTARKKKKKTSTKKK

KKGNDETYNLDIKKVLK

KKMVSISDLKSKLSKRR

KKNNDL EMNKLKKKS

RREEALNNKGNGKSVKK

KRLSGIMRSQQEHHRRK

FIG. 1F

KRRNPTRHEYNSRGKRL

KRNRELKRKEEARLSKK

KKDYEFDQSTTSFDKKK

KKLMFFVVKKFDKIRDK

KRLSERKAEKAEIRKRR

KKPRVVLNERKRRRRA

KKLGEFLNLLKAVVKRK

KREIYRISFQLSKIRRA

KKKLMPKSALLIRKYQK

KKTHLLDATDWRKLGR

RRVIAETFAKSSRNKSK

KRRHERYDQEERLRKQR

RKSDEPVSVKPSKKKSK

RKHSLISSLQARKSKSK

RRGSSNTSGSGGKRNSK

KKELKRREKQALLEKKK

KRPSKETPTSENKRSKG

KRDNFRFLEDAIKQLKK

RRQLIDKEKLQLKQKEK

KKKGVGKNVGVGKKVQK

RKRMRAVARLEKIKKKA

KRLSDTIVPPRSKRSQR

KKAKKDFYRFQVRERKK

RRTSKRHSREFSSSRKR

FIG. 1G

KKTKTNASKAEHIEKKK

KKKDRTDISKLCDKKER

KRDHKKQDFDAAKAKVR

KKRIINGESKSSTKKGK

KKYSKKTTSRPKREKRQ

KKTVNYKQLLIDKNKKR

KKPRLRLVCLQCKKIKR

KKNDNKSKGAQKRKNAK

KRPTSVVFIVPGSNKKK

KKDDKAMEPPNEKPHRK

KKVLLKEKAEAAKAKAK

KRNKDNRNSRVKKRKKY

KKNTRKGGKVYGKHKKK

KKKKKSKNGTISKTGKK

KKKAENKDIKKKKNSKK

KKKKSKKSKKSKKSKKS

PKKKRKVED

PKKKRKVDT

FIG. 2A
4x N-terminal NLS's Significantly Improves Passive Cas9 RNP uptake into Neural Stem Cells
Design of Cas9 Protein
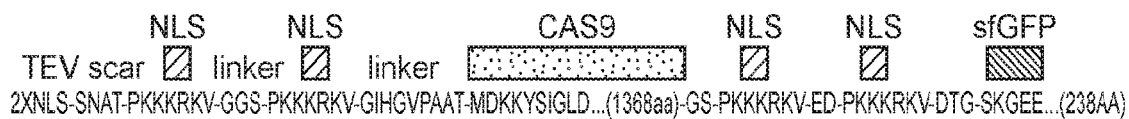
2XNLS-SNAT-PKKKRKV-GGS-PKKKRKV-GIHGVPAAT-MDKKYSIGLD...(1368aa)-GS-PKKKRKV-ED-PKKKRKV-DTG-SKGEE...(238AA)
N-term NLS
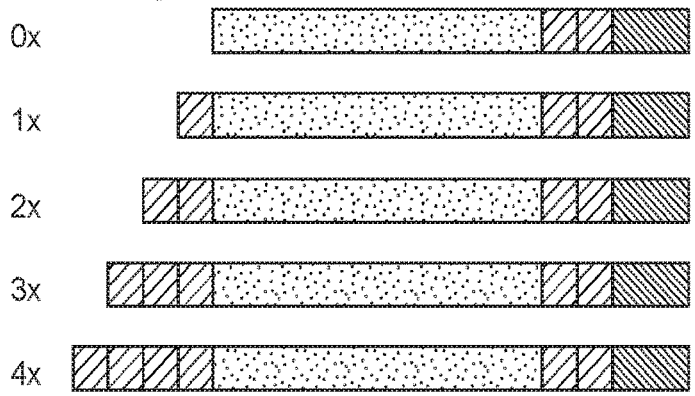
FIG. 2B
4xNLS-Cas9 design is significantly more efficient at editing cells
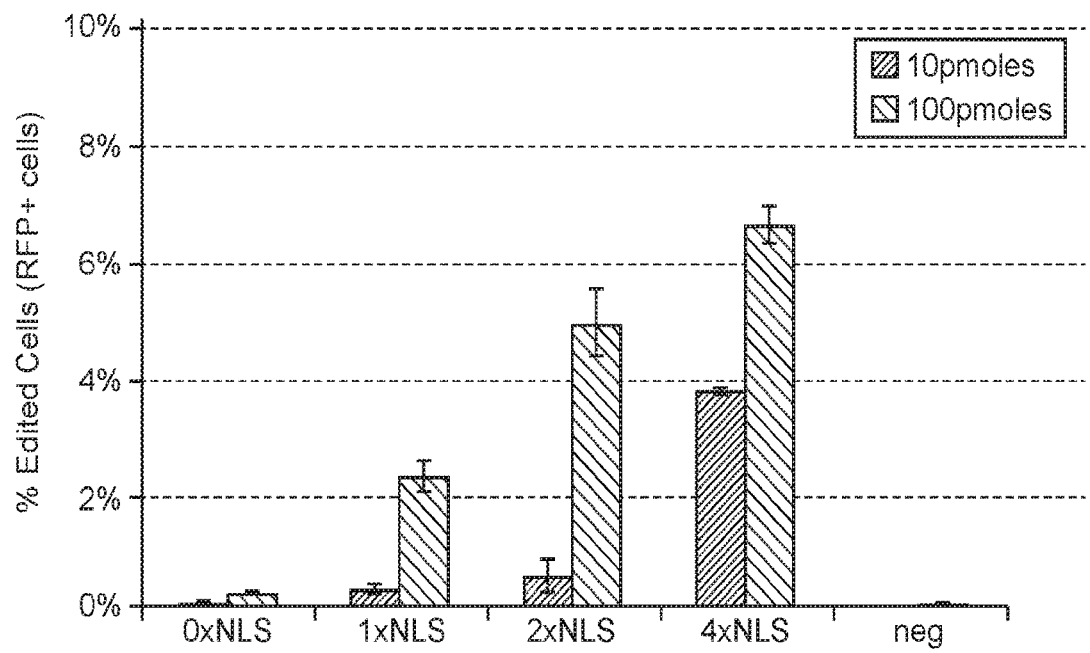

4xNLS-Cas9 Significantly Improves *in vivo* Cortical Cas9 RNP genome-editing.

CTX S1

4xNLS-Cas9 Significantly Improves *in vivo* Hippocampal Cas9 RNP genome-editing.

Subretinal Cas9 RNP injections: Genome-editing in retina includes cells surrounding injection site and distal Muller glia.

FIG. 7A

BS104 (4xNLS-SpyCas9-2xNLS-sfGFP)
Number of amino acids: 1678
Molecular weight: 193406.1
Theoretical pI: 6.72
Ext. coefficient 139360

SNATPKKKRKVGGSPKKKRKVGGSPKKKRKVGGSPKKKRKVGIHGVPAATMDKKYSIGLD
IGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPIFGNIVDEVAYHE
KYPTIYHLRKKLVDSTDKADLRLIYLALAHMIKFRGHFLIEGDLNPDNSDVDKLFIQLVQ
TYNQLFEENPINASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAILLSDILRVNT
EITKAPLSASMIKRYDEHHQDLTLLKALVRQQLPEKYKEIFFDQSKNGYAGYIDGGASQE
EFYKFIKPILEKMDGTEELLVKLNREDLLRKQRTFDNGSIPHQIHLGELHAILRRQEDFY
PFLKDNREKIEKILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGI
RDKQSGKTILDFLKSDGFANRNFMQLIHDDSLTFKEDIQKAQVSGQGDSLHEHIANLAGS
PAIKKGILQTVKVVDELVKVMGRHKPENIVIEMARENQTTQKGQKNSRERMKRIEEGIKE
LGSQILKEHPVENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNLTKAERGGLSE
LDKAGFIKRQLVETRQITKHVAQILDSRMNTKYDENDKLIREVKVITLKSKLVSDFRKDF
QFYKVREINNYHHAHDAYLNAVVGTALIKKYPKLESEFVYGDYKVYDVRKMIAKSEQEIG
KATAKYFFYSNIMNFFKTEITLANGEIRKRPLIETNGETGEIWDKGRDFATVRKVLSMP
QVNIVKKTEVQTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPKYSLFELENGR
KRMLASAGELQKGNELALPSKYVNFLYLASHYEKLKGSPEDNEQKQLFVEQHKHYLDEII
EQISEFSKRVILADANLDKVLSAYNKHRDKPIREQAENIIHLFTLTNLGAPAAFKYFDTT
IDRKRYTSTKEVLDATLIHQSITGLYETRIDLSQLGGDGSPKKKRKVEDPKKKRKVDTGS
KGEELFTGVVPILVELDGDVNGHKFSVRGEGEGDATNGKLTLKFICTTGKLPVPWPTLVT
TLTYGVQCFSRYPDHMKQHDFFKSAMPEGYVQERTISFKDDGTYKTRAEVKFEGDTLVNR
IELKGIDFKEDGNILGHKLEYNFNSHNVYITADKQKNGIKANFKIRHNVEDGSVQLADHY
QQNTPIGDGPVLLPDNHYLSTQSVLSKDPNEXRDHMVLLEFVTAAGITHGMDELYK

FIG. 7B

SNATPKKKRKVGGSPKKKRKVGGSPKKKRKVGGSPKKKRKVGIHGVPAATMDKKYSIGLD
IGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPIFGNIVDEVAYHE
KYPTIYHLRKKLVDSTDKADLRLIYLALAHMIKFRGHFLIEGDLNPDNSDVDKLFIQLVQ
TYNQLFEENPINASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAILLSDILRVNT
EITKAPLSASMIKRYDEHHQDLTLLKALVRQQLPEKYKEIFFDQSKNGYAGYIDGGASQE
EFYKFIKPILEKMDGTEELLVKLNREDLLRKQRTFDNGSIPHQIHLGELHAILRRQEDFY
PFLKDNREKIEKILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGI
RDKQSGKTILDFLKSDGFANRNFMQLIHDDSLTFKEDIQKAQVSGQGDSLHEHIANLAGS
PAIKKGILQTVKVVDELVKVMGRHKPENIVIEMARENQTTQKGQKNSRERMKRIEEGIKE
LGSQILKEHPVENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNLTKAERGGLSE
LDKAGFIKRQLVETRQITKHVAQILDSRMNTKYDENDKLIREVKVITLKSKLVSDFRKDF
QFYKVREINNYHHAHDAYLNAVVGTALIKKYPKLESEFVYGDYKVYDVRKMIAKSEQEIG
KATAKYFFYSNIMNFFKTEITLANGEIRKRPLIETNGETGEIVWDKGRDFATVRKVLSMP
QVNIVKKTEVQTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPKYSLFELENGR
KRMLASAGELQKGNELALPSKYVNFLYLASHYEKLKGSPEDNEQKQLFVEQHKYLDEII
EQISEFSKRVILADANLDKVLSAYNKHRDKPIREQAENIIHLFTLTNLGAPAAFKYFDTT
IDRKRYTSTKEVLDATLIHQSITGLYETRIDLSQLGGDGSPKKKRKVEDPKKKRKVDTGS

FIG. 8

Francisella tularensis subsp. novicida U112 Cpf1
type V CRISPR-associated protein Cpf1

```
   1  msiyqefvnk  yslsktlrfe  lipqgktlen  ikarglildd  ekrakdykka  kqiidkyhqf
  61  fieeilssvc  isedllqnys  dvyfklkksd  ddnlqkdfks  akdtikkqis  eyikdsekfk
 121  nlfnqnlida  kkgqesdlil  wlkqskdngi  elfkansdit  didealeiik  sfkgwttyfk
 181  gfhenrknvy  ssndiptsii  yrivddnlpk  flenkakyes  lkdkapeain  yeqikkdlae
 241  eltfdidykt  sevnqrvfsl  devfeianfn  nylnqsgitk  fntiiggkfv  ngentkrkgi
 301  neyinlysqq  indktlkkyk  msvlfkqils  dtesksfvid  kleddsdvvt  tmqsfyeqia
 361  afktveeksi  ketisllfdd  lkaqkldlsk  iyfkndkslt  dlsqqvfddy  svigtavley
 421  itqqiapknl  cnpskkeqel  iakktekaky  lsletiklal  eefnkhrdid  kqcrfeeila
 481  nfaaipmifd  eiaqnkdnla  qisikyqnqg  kkdllqasae  ddvkaikdll  dqtnnllhkl
 541  kifhisqsed  kanildkdeh  fylvfeecyf  elanivplyn  kirnyitqkp  ysdekfklnf
 601  enstlangwd  knkepdntai  lfikddkyyl  gvmnkknnki  fddkaikenk  gegykkivyk
 661  llpgankmlp  kvffsaksik  fynpsedilr  irnhsthtkn  gspqkgyekf  efniedcrkf
 721  idfykqsisk  hpewkdfgfr  fsdtqrynsi  defyrevenq  gykltfenis  esyidsvvnq
 781  gklylfqiyn  kdfsayskgr  pnlhtlywka  lfdernlqdv  vyklngeael  fyrkqsipkk
 841  ithpakeaia  nknkdnpkke  svfeydlikd  krftedkfff  hcpitinfks  sgankfndei
 901  nlllkekand  vhilsidrge  rhlayytlvd  gkgniikqdt  fniigndrmk  tnyhdklaai
 961  ekdrdsarkd  wkkinnikem  kegylsqvvh  eiaklvieyn  aivvfedlnf  qfkrgrfkve
1021  kqvyqklekm  lieklnylvf  kdnefdktgg  vlrayqltap  fetfkkmgkq  tgiiyyvpag
1081  ftskicpvtg  fvnqlypkye  svsksqeffs  kfdkicynld  kgyfefsfdy  knfgdkaakg
1141  kwtiasfgsr  linfrnsdkn  hnwdtrevyp  tkelekllkd  ysieyghgec  ikaaicgesd
1201  kkffakltsv  lntilqmrns  ktgteldyli  spvadvngnf  fdsrqapknm  pqdadangay
1261  higlkglmll  griknnqegk  klniviknee  yfefvqnrnn      (SEQ ID NO: 1252)
```

FIG. 8 (Cont.)

GenBankAccessionNo. WP_021736722
type V CRISPR-associated protein Cpf1 [Acidaminococcus sp. BV3L6].

```
   1  mtqfegftnl  yqvsktlrfe  lipqgktlkh  iqeqgfieed  karndhykel  kpiidriykt
  61  yadqclqlvq  ldwenlsaai  dsyrkektee  trnalieeqa  tyrnaihdyf  igrtdnltda
 121  inkrhaeiyk  glfkaelfng  kvlkqlgtvt  ttehenallr  sfdkfttyfs  gfyenrknvf
 181  saedistaip  hrivqdnfpk  fkenchiftr  litavpslre  hfenvkkaig  ifvstsieev
 241  fsfpfynqll  tqtqidlynq  llggisreag  tekikglnev  lnlaiqknde  tahiiaslph
 301  rfiplfkqil  sdrntlsfil  eefksdeevi  qsfckyktll  rnenvletae  alfnelnsid
 361  lthifishkk  letissalcd  hwdtlrnaly  erriseltgk  itksakekvq  rslkhedinl
 421  qeiisaagke  lseafkqkts  eilshahaal  dqplpttlkk  qeekeilksq  ldsllglyhl
 481  ldwfavdesn  evdpefsarl  tgiklemeps  lsfynkarny  atkkpysvek  fklnfqmptl
 541  asgwdvnkek  nngailfvkn  glyylgimpk  qkgrykalsf  eptektsegf  dkmyydyfpd
 601  aakmipkcst  qlkavtahfq  thttpillsn  nfiepleitk  eiydlnnpek  epkkfqtaya
 661  kktgdqkgyr  ealckwidft  rdflskytkt  tsidlsslrp  ssqykdlgey  yaelnpllyh
 721  isfqriaeke  imdavetgkl  ylfqiynkdf  akghhgkpnl  htlywtglfs  penlaktsik
 781  lngqaelfyr  pksrmkrmah  rlgekmlnkk  lkdqktpipd  tlyqelydyv  nhrlshdlsd
 841  earallpnvi  tkevsheiik  drrftsdkff  fhvpitlnyq  aanspskfnq  rvnaylkehp
 901  etpiigidrg  ernliyitvi  dstgkileqr  slntiqqfdy  qkkldnreke  rvaarqawsv
 961  vgtikdlkqg  ylsqviheiv  dlmihyqavv  vlenlnfgfk  skrtgiaeka  vyqqfekmli
1021  dklnclvlkd  ypaekvqgvl  npyqltdqft  sfakmgtqsg  flfyvpapyt  skidpltgfv
1081  dpfvwktikn  hesrkhfleg  fdflhydvkt  qdfilhfkmn  rnlsfqrglp  qfmpawdivf
1141  eknetqfdak  gtpfiagkri  vpvienhrft  gryrdlypan  elialleekg  ivfrdgsnil
1201  pkllenddsh  aidtmvalir  svlqmrnsna  atgedyinsp  vrdlngvcfd  srfqnpewpm
1261  dadangayhi  alkgqillnh  lkeskdlklq  ngisnqdwla  yiqelrn     (SEQ ID NO: 1253)
```

FIG. 8 (Cont.)

GenBankWP_051666128 type V CRISPR-associated protein Cpf1 [Lachnospiraceae bacterium ND2006].

```
   1  mlknvgidrl  dvekgrknms  klekftncys  lsktlrfkai  pvgktqenid  nkrllvedek
  61  raedykgvkk  lldryylsfi  ndvlhsiklk  nlnnyislfr  kktrtekenk  elenleinlr
 121  keiakafkgn  egykslfkkd  iietilpefl  ddkdeialvn  sfngfttaft  gffdnrenmf
 181  seeakstsia  frcinenltr  yisnmdifek  vdaifdkhev  qeikekilns  dydvedffeg
 241  effnfvltqe  gidvynalig  qfvtesgeki  kglneyinly  nqktkqklpk  fkplykqvls
 301  dreslsfyge  gytsdeevle  vfrntlnkns  eifssikkle  klfknfdeys  sagifvkngp
 361  aistiskdif  gewnvirdkw  naeyddihlk  kkavvtekye  ddrrksfkki  gsfsleqlqe
 421  yadadlsvve  klkeiiiqkv  deiykvygss  eklfdadfvl  ekslkkndav  vaimkdllds
 481  vksfenyika  ffgegketnr  desfygdfvl  aydillkvdh  iydairnyvt  qkpyskdkfk
 541  lyfqnpqfmg  gwdkdketdy  ratilrygsk  yylaimdkky  akclqkidkd  dvngnyekin
 601  ykllpgpnkm  lpkvffskkw  mayynpsedi  qkiykngtfk  kgdmfnlndc  hklidffkds
 661  isrypkwsna  ydfnfsetek  ykdiagfyre  veeqgykvsf  esaskkevdk  lveegklymf
 721  qiynkdfsdk  shgtpnlhtm  yfkllfdenn  hgqirlsgga  elfmrraslk  keelvvhpan
 781  spianknpdn  pkktttlsyd  vykdkrfsed  qyelhipiai  nkcpknifki  ntevrvllkh
 841  ddnpyvigid  rgernllyiv  vvdgkgnive  qyslneiinn  fngiriktdy  hslldkkeke
 901  rfearqnwts  ienikelkag  yisqvvhkic  elvekydavi  aledlnsgfk  nsrvkvekqv
 961  yqkfekmlid  klnymvdkks  npcatggalk  gyqitnkfes  fksmstqngf  ifyipawlts
1021  kidpstgfvn  llktkytsia  dskkfissfd  rimyvpeedl  fefaldyknf  srtdadyikk
1081  wklysygnri  rifrnpkknn  vfdweevclt  saykelfnky  ginyqqgdir  allceqsdka
1141  fyssfmalms  lmlqmrnsit  grtdvdflis  pvknsdgify  dsrnyeaqen  ailpknadan
1201  gayniarkvl  waigqfkkae  dekldkvkia  isnkewleya  qtsvkh      (SEQ ID NO: 1254)
```

FIG. 8 (Cont.)

GenBank WP_018359861
type V CRISPR-associated protein Cpf1
Porphyromonas macacae

```
   1 mktqhffedf tslyslskti rfelkpigkt lenikkngli rrdeqrlddy eklkkvidey
  61 hedfianils sfsfseeilq syiqnlsese arakiektmr dtlakafsed eryksifkke
 121 lvkkdipvwc paykslckkf dnfttslvpf henrknlyts neitasipyr ivhvnlpkfi
 181 qniealcelq kkmgadlyle mmenlrnvwp sfvktpddlc nlktynhlmv qssiseynrf
 241 vggystedgt khqginewin iyrqrnkemr lpglvflhkq ilakvdsssf isdtlenddq
 301 vfcvlrqfrk lfwntvsske ddaaslkdlf cglsgydpea iyvsdahlat isknifdrwn
 361 yisdairrkt evlmprkkes veryaekisk qikkrqsysl aelddllahy seeslpagfs
 421 llsyftslgg qkylvsdgev ilyeegsniw devliafrdl qvildkdfte kklgkdeeav
 481 svikkaldsa lrlrkffdll sgtgaeirrd ssfyalytdr mdklkgllkm ydkvrnyltk
 541 kpysiekfkl hfdnpsllsg wdknkelnnl svifrqngyy ylgimtpkgk nlfktlpklg
 601 aeemfyekme ykqiaepmlm lpkvffpkkt kpafapdqsv vdiynkktfk tgqkgfnkkd
 661 lyrlidfyke altvhewklf nfsfspteqy rnigeffdev reqaykvsmv nvpasyidea
 721 vengklylfq iynkdfspys kgipnlhtly wkalfseqnq srvyklcggg elfyrkaslh
 781 mqdttvhpkg isihkknlnk kgetslfnyd lvkdkrfted kfffhvpisi nyknkkitnv
 841 nqmvrdyiaq nddlqiigid rgernllyis ridtrgnlle qfslnviesd kgdlrtdyqk
 901 ilgdreqerl rrqewksie sikdlkdgym sqvvhkicnm vvehkaivvl enlnlsfmkg
 961 rkkveksvye kfermlvdkl nylvvdkknl snepgglyaa yqltnplfsf eelhrypqsg
1021 ilffvdpwnt sltdpstgfv nllgrinytn vgdarkffdr fnairydgkg nilfdldlsr
1081 fdvrvetqrk lwtlttfgsr iakskksgkw mverienlsl cflelfeqfn igyrvekdlk
1141 kailsqdrke fyvrliylfn lmmqirnsdg eedyilspal neknlqfdsr lieakdlpvd
1201 adangaynva rkglmvvqri krgdhesihr igraqwlryv qegive (SEQ ID NO: 1255)
```

FIG. 8 (Cont.)

GenBank WP_050786240
type V CRISPR-associated protein Cpf1
Prevotella disiens

```
   1  mkvmenyqef  tnlfqlnktl  rfelkpigkt  celleegkif  asgsflekdk  vradnvsyvk
  61  keidkkhkif  ieetlssfsi  sndllkqyfd  cynelkafkk  dcksdeeevk  ktalrnkcts
 121  iqramreais  qaflkspqkk  llaiknlien  vfkadenvqh  fseftsyfsg  fetnrenfys
 181  deekststay  rlvhdnlpif  ikniyifekl  keqfdaktls  eifenyklyv  agssldevfs
 241  leyfnnrltq  kgidnynavi  gkivkedkqe  iqglnehinl  ynqkhkdrrl  pffislkkqi
 301  lsdrealswl  pdmfkndsev  ikalkgfyie  dgfennvltp  latllssldk  ynlngifirn
 361  nealsslsqn  vyrnfsidea  idanaelqtf  nnyelianal  rakikketkq  grksfekyee
 421  yidkkvkaid  slsiqeinel  venyvsefns  nsgnmprkve  dyfslmrkgd  fgsndlieni
 481  ktklsaaekl  lgtkyqetak  difkkdensk  likelldatk  qfqhfikpll  gtgeeadrdl
 541  vfygdflply  ekfeeltlly  nkvrnrltqk  pyskdkirlc  fnkpklmtgw  vdskteksdn
 601  gtqyggylfr  kkneigeydy  flgisskaql  frkneavigd  yerldyyqpk  antiygsaye
 661  gensykedkk  rlnkviiayi  eqikqtnikk  siiesiskyp  nisdddkvtp  ssllekikkv
 721  sidsyngils  fksfqsvnke  vidnllktis  plknkaefld  linkdyqift  evqavideic
 781  kqktfiyfpi  snvelekemg  dkdkplclfq  isnkdlsfak  tfsanlrkkr  gaenlhtmlf
 841  kalmegnqdn  ldlgsgaify  raksldgnkp  thpaneaikc  rnvankdkvs  lftydiyknr
 901  rymenkflfh  lsivqnykaa  ndsaqlnssa  teyirkaddl  hiigidrger  nllyysvidm
 961  kgniveqdsl  niirnndlet  dyhdlldkre  kerkanrqnw  eavegikdlk  kgylsqavhq
1021  iaqlmlkyna  iialedlgqm  fvtrgqkiek  avyqqfeksl  vdklsylvdk  krpynelggi
1081  lkayqlassi  tknnsdkqng  flfyvpawnt  skidpvtgft  dllrpkamti  keaqdffqaf
1141  dnisyndkgy  fefetnydkf  kirmksaqtr  wtictfgnri  krkkdknywn  yeevelteef
1201  kklfkdsnid  yencnlkeei  qnkdnrkffd  dlikllqltl  qmrnsddkgn  dyiispvana
1261  egqffdsrng  dkklpldada  ngayniarkg  lwnirqikqt  kndkklnlsi  sstewldfvr
1321  ekpylk      (SEQ ID NO: 1256)
```

FIG. 8 (Cont.)

GenBank WP_021296342
Alicyclobacillus acidoterrestris
type V CRISPR-associated protein C2c1

```
   1 mavksikvkl rlddmpeira glwklhkevn agvryytewl sllrqenlyr rspngdgeqe
  61 cdktaeecka ellerlrarq venghrgpag sddellqlar qlyellvpqa igakgdaqqi
 121 arkflsplad kdavgglgia kagnkprwvr mreagepgwe eekekaetrk sadrtadvlr
 181 aladfglkpl mrvytdsems svewkplrkg qavrtwdrdm fqqaiermms weswnqrvgq
 241 eyaklveqkn rfeqknfvgq ehlvhlvnql qqdmkeaspg leskeqtahy vtgralrgsd
 301 kvfekwgkla pdapfdlyda eiknvqrrnt rrfgshdlfa klaepeyqal wredasfltr
 361 yavynsilrk lnhakmfatf tlpdatahpi wtrfdklggn lhqytflfne fgerrhairf
 421 hkllkvengv arevddvtvp ismseqldnl lprdpnepia lyfrdygaeq hftgefggak
 481 iqcrrdqlah mhrrrgardv ylnvsvrvqs qseargerrp pyaavfrlvg dnhrafvhfd
 541 klsdylaehp ddgklgsegl lsglrvmsvd lglrtsasis vfrvarkdel kpnskgrvpf
 601 ffpikgndnl vavhersqll klpgeteskd lraireerqr tlrqlrtqla ylrllvrcgs
 661 edvgrrersw aklieqpvda anhmtpdwre afenelqklk slhgicsdke wmdavyesvr
 721 rvwrhmgkqv rdwrkdvrsg erpkirgyak dvvggnsieq ieylerqykf lkswsffgkv
 781 sgqviraekg srfaitlreh idhakedrlk kladriimea lgyvyalder gkgkwvakyp
 841 pcqlilleel seyqfnndrp psennqlmqw shrgvfqeli nqaqvhdllv gtmyaafssr
 901 fdartgapgi rcrrvparct qehnpepfpw wlnkfvveht ldacplradd liptgegeif
 961 vspfsaeegd fhqihadlna aqnlqqrlws dfdisqirlr cdwgevdgel vliprltgkr
1021 tadsysnkvf ytntgvtyye rergkkrrkv faqeklseee aellveadea reksvvlmrd
1081 psgiinrqnw trqkefwsmv nqriegylvk qirsrvplqd sacentgdi
```

(SEQ ID NO: 1280)

FIG. 8 (Cont.)

GenBank WP_026976134.1
Alicyclobacillus contaminans
type V CRISPR-associated protein C2c1

```
  1 mgfntaellr  kveeemrkts  vgfdtdnpfa  hritrrairg  wdriaeawrr  lppdapesey
 61 ieafkdiqrk  nprkigsepl  fknlaapgvr  sellnnpqvl  itfakynelq  rqlakakqfa
121 qktlphpvfh  pvwvrydklg  gnlhhyqiep  avhandthkv  kfsslllpqe  dgsyaevkdv
181 tvslapslqf  ptglvhpkvt  tpprtglvtv  mdeeagkpvv  cyrdrghdal  vpvafggakl
241 qfnrahlsag  yrkgvlsagg  ggsiyfnvtl  dvqvpnerdv  sktfsfsrdr  dlvslkaeel
301 krymetkplg  mpgvrvmsvd  lgvrygaais  vfevkpfaev  rkdklhypit  gcegfvaehe
361 rsvilklpge  gvrtagkqse  rkqalaaira  emsilrkwlr  vsqvteedra  kavrglllede
421 rgggwtmdpg  edsdhqplqq  flhearlavg  elvnlvhlsp  aeweravier  hrrleritas
481 hirvfqtmrk  vwgkrrneda  ahtggislah  iehliqqrkl  firwsthart  ygevrrlpkh
541 egfakrlqkh  tnhvkedrik  kladmivmaa  rgyrfldkra  rwvktrhapc  dlilfedlsr
601 yrftmdrppt  ensqlmnwsh  rellktvkmq  aalfgigvgt  vpaaftsrfd  aqtgapglrc
661 krvtkqdkek  tpfwliqfae  itgvnvtnve  pgqlipvdgg  ewfvspkgpr  aadglkcvha
721 dinaahnlqr  rfwiprlpsv  kcrryveaeg  faavpsstaf  mkvhgkgafv  svdgefyeyq
781 kgrrvavnra  drtsstlded  egdigeemlv  ssngagefvr  mfydesgyvg  ygrwmdskvf
841 wgkvrqivhr  aiqdqvekra  aargengats  sr
```

(SEQ ID NO: 1281)

FIG. 8 (Cont.)

GenBank WP_027186183.1
Desulfovibrio inopinatus
type_V CRISPR-associated protein C2c1

```
   1 mptrtinlkl vlgknpenat lrralfsthr lvnqatkrie eflllcrgea yrtvdnegke
  61 aeiprhavqe ealafakaaq rhngcistye dqeildvlrq lyerlvpsvn enneagdaqa
 121 anawvsplms aesegglsvy dkvldpppvw mklkeekapg weaasqiwiq sdegqsllnk
 181 pgspprwirk lrsgqpwqdd fvsdqkkkqd eltkgnapli kqlkemgllp lvnpffrhll
 241 dpegkgvspw drlavraava hfisweswnh rtraeynslk lrrdefeaas defkddftll
 301 rqyeakrhst lksialadds npyrigvrsl rawnrvreew idkgateeqr vtilsklqtq
 361 lrgkfgdpdl fnwlaqdrhv hlwsprdsvt plvrinavdk vlrrrkpyal mtfahprfhp
 421 rwilyeapgg snlrqyaldc tenalhitlp llvddahgtw iekkirvpla psgqiqdltl
 481 eklekkknrl yyrsgfqqfa glaggaevlf hrpymehder seesllerpg avwfkltldv
 541 atqappnwld gkgrvrtppe vhhfktalsn kskhtrtlqp glrvlsvdlg mrtfascsvf
 601 eliegkpetg rafpvaders mdspnklwak hersfkltlp getpsrkeee ersiaraeiy
 661 alkrdiqrlk sllrlgeedn dnrrdalleq ffkgwgeedv vpgqafprsl fqglgaapfr
 721 stpelwrqhc qtyydkaeac lakhisdwrk rtrprptsre mwyktrsyhg gksiwmleyl
 781 davrklllsw slrgrtygai nrqdtarfgs lasrllhhin slkedriktg adsivqaarg
 841 yiplphqkgw eqryepcqli lfedlaryrf rvdrprrens qlmqwnhrai vaettmqael
 901 ygqiventaa gfssrfhaat gapgvrcrfl lerdfdndlp kpyllrelsw mlgntkvese
 961 eeklrllsek irpgslvpwd ggeqfatlhp krqtlcviha dmnaaqnlqr rffgrcqeaf
1021 rlvcqphgdd vlrlastpga rllgalqqle ngqgafelvr dmgstsqmnr fvmkslgkkk
1081 ikplqdnngd deledvlsvl peeddtgrit vfrdssgiff pcnvwipakq fwpavramiw
1141 kvmashslg
```

(SEQ ID NO: 1282)

FIG. 8 (Cont.)

GenBank WP_031386437.1
Desulfonatronum thiodismutans
type V CRISPR-associated protein C2c1

```
   1 mvlgrkddta elrralwtth ehvnlavaev ervllrcrgr sywtldrrgd pvhvpesqva
  61 edalamarea qrrngwpvvg edeeillalr ylyeqivpsc llddlgkplk gdaqkigtny
 121 agplfdsdtc rrdegkdvac cgpfhevagk ylgalpewat piskqefdgk dashlrfkat
 181 ggddaffrvs iekanawyed panqdalknk aynkddwkke kdkgisswav kyiqkqlqlg
 241 qdprtevrrk lwlelgllpl fipvfdktmv gnlwnrlavr lalahllswe swnhravqdq
 301 alarakrdel aalflgmedg faqlreyelr rnesikqhaf epvdrpyvvs gralrswtrv
 361 reewlrhgdt qesrknicnr lqdrlrgkfg dpdvfhwlae dgqealwker dcvtsfslln
 421 dadgllekrk gyalmtfada rlhprwamye apggsnlrty qirktenglw advvllsprn
 481 esaaveektf nvrlapsgql snvsfdqiqk gskmvgrcry qsanqqfegl lggaeilfdr
 541 krianeqhga tdlaskpghv wfkltldvrp qapqgwldgk grpalppeak hfktalsnks
 601 kfadqvrpgl rvlsvdlgvr sfaacsvfel vrggpdqgty fpaadgrtvd dpeklwakhe
 661 rsfkitlpge npsrkeeiar raameelrsl ngdirrlkai lrlsvlqedd prtehlrlfm
 721 eaivddpaks alnaelfkgf gddrfrstpd lwkqhchffh dkaekvvaer fsrwrtetrp
 781 kssswqdwre rrgyaggksy wavtyleavr glilrwnmrg rtygevnrqd kkqfgtvasa
 841 llhhinqlke driktgadmi iqaargfvpr kngaqwvqvh epcrlilfed laryrfrtdr
 901 srrensrlmr wshreivnev gmqgelyglh vdtteagfss rylassgapg vrcrhlveed
 961 fhdglpgmhl vgeldwllpk dkdrtanear rllggmvrpg mlvpwdggel fatlnaasql
1021 hvihadinaa qnlqrrfwgr cgeairivcn qlsvdgstry emakapkarl lgalqqlkng
1081 dapfhltsip nsqkpensyv mtptnagkky ragpgekssg eedelaldiv eqaeelaqgr
1141 ktffrdpsgv ffapdrwlps eiywsrirrr iwqvtlerns sgrqeraemd empy
```

(SEQ ID NO: 1283)

FIG. 8 (Cont.)

GenBank WP_027726362
Tuberibacillus calidus
type V CRISPR-associated protein C2c1

```
   1 matksfilkm ktknnpqlrl slwkthelfn fgvayymdll slfrqkdlym hndedpdhpv
  61 vlkkeelqer lwmkvretqq knqfhgevsk devletlral yeelvpsavg ksgeanqisn
 121 kylypltdpa sqsgkgtans grkprwkklk eagdpswkda yekwekerqe dpklkilaal
 181 qsfgliplfr pftendhkav isvkwmpksk nqsvrkfdkd mfnqaierfl sweswnekva
 241 edyektvsiy eslqkelkgi stkafeimer vekayeahlr eitfsnstyr ignrairgwt
 301 eivkkwmkld psapqgnyld vvkdyqrrhp resgdfklfe llsrpenqaa wreypeflpl
 361 yvkyrhaeqr mktakkqatf tlcdpirhpl wvryeersgt nlnkyrlimn ekekvvqfdr
 421 liclnadghy eeqedvtvpl apsqqfddqi kfssedtgkg khnfsyyhkg inyelkqtlg
 481 gariqfdreh llrrqqvkag nvgriflnvt lniepmqpfs rsgnlqtsvg kalkvyvdgy
 541 pkvvnfkpke ltehikesek ntltlgvesl ptglrvmsvd lgqrqaaais ifevvsekpd
 601 dnklfypvkd tdlfavhrts fniklpgekr terrmleqqk rdqairdlsr klkflknvln
 661 mqklektder ekrvnrwikd rereeenpvy vqefemiskv lysphsvwvd qlksihrkle
 721 eqlgkeiskw rqsisqgrqg vygislknie diektrrllf rwsmrpenpg evkqlqpger
 781 faidqqnhln hlkddrikkl anqivmtalg yrydgkrkkw iakhpacqlv lfedlsryaf
 841 ydersrlenr nlmrwsrrei pkqvaqiggl ygllvgevga qyssrfhaks gapgircrvv
 901 kehelyiteg gqkvrnqkfl dslvenniie pddarrlepg dlirdqggdk fatldergel
 961 vithadinaa qnlqkrfwtr thglyrirce sreikdavvl vpsdkdqkek menlfgigyl
1021 qpfkqendvy kwvkgekikg kktssqsddk elvseilqea svmadelkgn rktlfrdpsg
1081 yvfpkdrwyt ggryfgtleh llkrklaerr lfdggssrrg lfngtdsntn ve
```

(SEQ ID NO: 1284)

FIG. 8 (Cont.)

GenBank WP_041902512.1
Bacillus thermoamylovorans
type V CRISPR-associated protein C2c1

```
   1 matrsfilki epneevkkgl wkthevlnhg iayymnilkl irqeaiyehh eqdpknpkkv
  61 skaeiqaelw dfvlkmqkcn sfthevdkdv vfnilrelye elvpssvekk qeanqlsnkf
 121 lyplvdpnsq sgkgtassgr kprwynlkia gdpsweeekk kweedkkkdp lakilgklae
 181 ygliplfipf tdsnepivke ikwmeksrnq svrrldkdmf iqalerflsw eswnlkvkee
 241 yekvekehkt leerikediq afksleqyek erqeqllrdt lntneyrlsk rglrgwreii
 301 qkwlkmdene psekylevfk dyqrkhprea gdysvyefls kkenhfiwrn hpeypylyat
 361 fceidkkkkd akqqatftla dpinhplwvr feersgsnln kyrilteqlh teklkkkltv
 421 qldrliypte sggweekgkv divllpsrqf ynqifldiee kgkhaftykd esikfplkgt
 481 lggarvqfdr dhlrryphkv esgnvgriyf nmtvniepte spvskslkih rddfpkfvnf
 541 kpkeltewik dskgkklksg iesleiglrv msidlgqrqa aaasifevvd qkpdiegklf
 601 fpikgtelya vhrasfnikl pgetlvksre vlrkarednl klmnqklnfl rnvlhfqqfe
 661 diterekrvt kwisrqensd vplvyqdeli qirelmykpy kdwvaflkql hkrleveigk
 721 evkhwrksls dgrkglygis lknideidrt rkfllrwslr ptepgevrrl epgqrfaidq
 781 lnhlnalked rlkkmantii mhalgycydv rkkkwqaknp acqiilfedl snynpyeers
 841 rfensklmkw srreiprqva lqgeiyglqv qevgaqfssr fhaktgspgi rcsvvtkekl
 901 qdnrffknlq regrltldki avlkegdlyp dkggekfisl skdrklvtth adinaaqnlq
 961 krfwtrthgf ykvyckayqv dgqtvyipes kdqkqkiiee fqegyfilkd gvyewgnagk
1021 lkikkgsskq ssselvdsdi lkdsfdlase lkgeklmlyr dpsgnvfpsd kwmaagvffg
1081 kleriliskl tnqysistie ddsskqsm
```

(SEQ ID NO: 1285)

FIG. 8 (Cont.)

GenBank WP_026557978.1
Bacillus sp. NSP2.1
type V CRISPR-associated protein C2c1

```
   1 mairsiklkl  kthtgpeaqn  lrkgiwrthr  llnegvayym  kmlllfrqes  tgerpkeelq
  61 eelichireq  qqrnqadknt  qalpldkale  alrqlyellv  pssvgqsgda  qiisrkflsp
 121 lvdpnseggk  gtskagakpt  wqkkkeandp  tweqdyekwk  krreedptas  vittleeygi
 181 rpifplytnt  vtdiawlplq  snqfvrtwdr  dmlqqaierl  lsweswnkrv  qeeyaklkek
 241 maqlneqleg  gqewislleq  yeenrerelr  enmtaandky  ritkrqmkgw  nelyelwstf
 301 pasasheqyk  ealkrvqqrl  rgrfgdahff  qylmeeknrl  iwkgnpqrih  yfvarneltk
 361 rleeakqsat  mtlpnarkhp  lwvrfdargg  nlqdyyltae  adkprsrrfv  tfsqliwpse
 421 sqwmekkdve  velalsrqfy  qqvkllkndk  gkqkiefkdk  gsgstfnghl  ggaklqlerg
 481 dlekeeknfe  dgeigsvyln  vvidfeplqe  vkngrvqapy  gqvlqlirrp  nefpkvttyk
 541 seqlvewika  spqhsagves  lasgfrvmsi  dlglraaaat  sifsveessd  knaadfsywi
 601 egtplvavhq  rsymlripge  qvekqvmekr  derfqlhqrv  kfqirvlaqi  mrmankqygd
 661 rwdeldslkq  aveqkkspld  qtdrtfwegi  vcdltkvlpr  neadweqavv  qihrkaeeyv
 721 gkavqawrkr  faaderkgia  glsmwnieel  eglrkllisw  srrtrnpqev  nrferghtsh
 781 qrllthiqnv  kedrikqlsh  aivmtalgyv  yderkqewca  eypacqvilf  enlsqyrsnl
 841 drstkenstl  mkwahrsipk  yvhmqaepyg  iqigdvraey  ssrfyaktgt  pgirckkvrg
 901 qdlqgrrfen  lqkrlvneqf  lteeqvkqlr  pgdivpddsg  elfmtltdgs  gskevvflqa
 961 dinaahnlqk  rfwqrynelf  kvscrvivrd  eeeylvpktk  svqaklgkql  fvkksdtawk
1021 dvyvwdsqak  lkgkttftee  sespeqledf  qeiieeaeea  kgtyrtlfrd  psgvffpesv
1081 wypqkdfwge  vkrklygklr  erfltkar
```

(SEQ ID NO: 1286)

FIG. 8 (Cont.)

GenBank WP_015927307.1
Methylobacterium nodulans
type V CRISPR-associated protein C2c1

```
  1 mltkqdkqqk ityctnmnev feaklgsadl llnwdhlrgr irdrvdagdi gsaflklald
 61 vahvlpdgvd dqlaraafhf qsakgakskh adsvqaglrv lsidlgvrsf atcsvfelkd
121 tapttgvafp laefrlwavh ersftlelpg envgaagqqw raqadaelrq lrgglnrhrq
181 llraatvqkg erdayltdlr eawsakelwp feasllsele rcstvadplw qdtckraarl
241 yrtefgavvs ewrsrtrsre drkyagksmw svqhltdvrr flqswslagr asgdirrldr
301 erggvfakdl ldhidalkdd rlktgadliv qaargfqrne fgywvqkhap chvilfedls
361 ryrmrtdrpr rensqlmqwa hrgvpdmvgm qgeiygiqdr rdpdsarkha rqplaafcld
421 tpaafssryh astmtpgirc hplrkrefed qgflellkre negldlngyk pgdlvplpgg
481 evfvclnang lsrihadina aqnlqrrfwt qhgdafrlpc gksavqgqir waplsmgkrq
541 agalggfgyl eptghdsgsc qwrktteaew rrlsgaqkdr deaaaaedee lqgleeelle
601 rsgervvffr dpsgvvlptd lwfpsaafws ivraktvgrl rshldaqaea syavaagl
```

(SEQ ID NO: 1287)

FIG. 8 (Cont.)

AUX0013399408.1 - Gut metagenome contig-6000335, whole genome shotgun sequence type V CRISPR-associated protein C2c3

```
   1 mkkfelkqnf rnnysgktlr nfrqtlaqia nkkssdsilt ikfkldcskt gklpkyenli
  61 slydtiedik kgtlsyylft livsgfkffg sasqakafst kdifkdndfy nqfkiqshld
 121 lpdfvpskiy qrlkknvrst ngkdnafkas vivaeyrkei gklknkdess ehqceelfkk
 181 igtaletrfs swqdlinncs tgceiideil ndsfgtlpsi kkmvlasttq ssdgeqdgia
 241 iaydpdstfi ksdellnpyf avatilksmp peiqqdkksa yvkanlttpt hnalswifgk
 301 gitlfqtest eklcamfnvs dkrvieqvqd aakavklpae ldlnhctlkf qdfrsslggh
 361 ldswttnylk rldelndlll nlpknlslpd ifmidgkdfi eysgcnrdei qqmidfvvne
 421 qnriklqesl nallgkgnnq icsddistvk dfseivnslh sfvqqidnsl eqssneansi
 481 fselkkkiek nekwdiwknn lkkipklnkl sggvpdawke ireieqkfhe isenqkkhft
 541 evmewidagn gtidifesrf kydellkksk knnlqsadel afrsvlnklg rfarqgndlv
 601 cekiknwfke qnifdsskdf nryfinqkgf ifkhpsskkd nspynlsanl lekryevtnt
 661 vgalleqces dpaivndpfs mrslvefral wfsinisgis keqhiptkia qpklddstyq
 721 esvsptlkyr lekeqitsse lnsiftvyks llsqlsirls rnsfylrtkf swignnsliy
 781 cpkettwkip aayfksdlwn eykdkqiliv neeydvdvvk tfesvykivk skdnneknri
 841 lpllkqlphd wmfklpfgas naekckvlkl eknnkkfkpl svskdslarl sgpstyfnqi
 901 deimmndese lsemtllade pvrqqmsngk ieiipddyvm slaipitrsl kkgntesfpf
 961 knivsidqge agfayavfkl sdcgneraep iatglipips irrlihsvkk yrgkkqriqn
1021 fnqkfdstmf tlrenvtgdi cglivalmkk ynafpilekq vgnlesgskq lmlvykavns
1081 kflaakvdmq ndqrrswwyq gnswntpilr isnpnqsnnk nivkningkk yeelkiypgy
1141 svsaymtsci chvcgrnale llknddstgk vkkyqinqdg evtiggevik lyrkpdrltp
1201 vknlakkgnr ertyasiner aptvsvqkae lsadelqkii kknmrraprs lmskdttqsr
1261 yfcvfkncpc hnkeqhadvn aainigrrfl kdcilddnke kd
```

(SEQ ID NO: 1290)

FIG. 8 (Cont.)

CEQE01148443.1 - marine metagenome genome assembly TARA_037_MES_0.22-1.6, contig TARA_037_MES_0.22-1.6_scaffold26048_1, whole genome shotgun sequence type V CRISPR-associated protein C2c3

```
   1 mrsnyhggrn arqwrkqisg larrtketvf tykfpletda aeidfdkavq tygiaegvgh
  61 gsliglvcaf hlsgfrlfsk ageamafrnr sryptdafae klsaimgiql ptlspegldl
 121 ifqspprsrd giapvwsene vrnrlytnwt grgpankpde hlleiageia kqvfpkfggw
 181 ddlasdpdka laaadkyfqs qgdfpsiasl paaimlspan stvdfegdyi aidpaaetll
 241 hqavsrcaar lgrerpdldq nkgpfvsslq dalvssqnng lswlfgvgfq hwkekspkel
 301 ideykvpadq hgavtqvksf vdaiplnplf dtthyqefra svagkvrswv anywkrlldl
 361 ksllatteft lpesisdpka vslfsgllvd pqglkkvads lparlvsaee aidrlmgvgi
 421 ptaadiaqve rvadeigafi gqvqqfnnqv kqklenlqda ddeeflkglk ielpsgdkep
 481 painrisgga pdaaaeisel eeklqrllda rsehfqtise waeenavtld piaamveler
 541 lrlaergatg dpeeyalrll lqrigrlanr vspvsagsir ellkpvfmee refnlffhnr
 601 lgslyrspys tsrhqpfsid vgkakaidwi agldqissdi ekalsgagea lgdqlrdwin
 661 lagfaisqrl rglpdtvpna laqvrcpddv rippllamll eeddiardvc lkafnlyvsa
 721 ingclfgalr egfivrtrfq rigtdqihyv pkdkaweypd rlntakgpin aavssdwiek
 781 dgavikpvet vrnlsstgfa gagvseylvq aphdwytpld lrdvahlvtg lpveknitkl
 841 krltnrtafr mvgassfkth ldsvllsdki klgdftiiid qhyrqsvtyg gkvkisyepe
 901 rlqveaavpv vdtrdrtvpe pdtlfdhiva idlgersvgf avfdiksclr tgevkpihdn
 961 ngnpvvgtva vpsirrlmka vrshrrrqp nqkvnqtyst alqnyrenvi gdvcnridtl
1021 merynafpvl efqiknfqag akqleivygs vlhrytfsgv dahkakrrey wyngelwehp
1081 ylmakkwnee tnsmsgapkp vslfpgvtvn aartsqichq cqrnpmshlr gltgtieiss
1141 dglleleddgt irlfetsdyd edkfkqsrre krrldanvll sgrhraeyiy tvakrnlrrp
1201 pknvmtkdtt qsrytclykn cswtghaden aainigrryl aeridmpask tkaav
```

(SEQ ID NO: 1291)

FIG. 8 (Cont.)

CEVA01036528.1 - marine metagenome genome assembly TARA_125_SRF_0.45-0.8, contig TARA_125_SRF_0.45-0.8_scaffold80227_1, whole genome shotgun sequence
type V CRISPR-associated protein C2c3

```
   1 mrprfhggmn ardwrkhvgv laqqhkettr tytfpldttg saidfdaalq aynavegvgy
  61 gsllglacav hlsgfrlfst gkeaatfrnr arypnaafqa alrkelgtti ttltpetldr
 121 lfssrpkrrn gvplpwnqds irdrlytnwv kprpgdtpda vlfqiatgia qeitedvssw
 181 tdlaknsdrg lkaahryfar vggfpafdnl tppatvqptd ttidydpnap fhlvshadqt
 241 lihqsislca hrirqedpal dpnksgfikq lqnnflsqtf yglswlfgag yvhfrectan
 301 dlaiqygipn ncrdgihqik sfadailpnt ffekkhyrkd srsvgkkaks wisnywqrll
 361 qlqtwvddht wvtlpqelte aqfkplfrgl lvdavelmai aerlpqrlad crdsldclmq
 421 kgpqaatknd veivekvree iesfvgqieq lgnqlrhqle nenndqvhrd nlhqlknrlp
 481 ldlrrpqaln kisggvpdva ksirgletql dqvlkerrsh fgrltkwake cgitldplqp
 541 liesekqrva ergsahdake lairlllqri grlghrlspt nataiqellr pvfavkrefn
 601 lffhnhmgal yrspystsrh qpfqinvdva hgtdwigtie tliqnlftqi qddallrdlv
 661 qlegfvfshk lralpgvips elarpnnlqq mglpalllvl lqadqvhret vlrvfnlygs
 721 aingylfqal rpgfivragf qrletkklry vpkaqswqyp drlhhaksai knslsagwik
 781 knhqgailpq ktltalvkqk slkdtgvpey lvqaphdwyv pidlrgpaip iegltvgteg
 841 peltqlgpmk ddcafraigp ssfkskidag llpqdvkygd mtlifdqhyq qsisfangtf
 901 siqyqptslq vkaaipvvdk rprdtrnnsh lydrivaidl gerkigyaif dlkqvlkseq
 961 lepmredgkp ligsisirsi rglmkavqth rnrrqpnyri dqtyskalmh yresvigdvc
1021 naidtlcary ggfpvlessv rnfevgsaql ktvygsvsrr ytwsavdahk nqrqqywlgg
1081 tkdkipiwth pylmtrewde knskwsnrsk plkmhpgvev hpagtsqich qckrnpigal
1141 wnvadtvvld dqgqldlddg tirlnsgyid tteikrarrk kirlpenkpl tgshktshvr
1201 avarrnlrqp pkstrakdtt qsrytclyvd cghechaden aainigrkyl qerihieasr
1261 qalstr    (SEQ ID NO: 1292)
```

FIG. 8 (Cont.)

CEPS01188136.1 - marine metagenome genome assembly TARA_038_MES_0.22-1.6, contig TARA_038_MES_0.22-1.6_C8568097_1, whole genome shotgun sequence
type V CRISPR-associated protein C2c3

```
   1 mvaglkkikr dgvtmksnyh ggvkarawrk rigglarrqk etvftykfpl eteeagidfd
  61 kavqtygiae gisqgsligl vcafhlsgfr lfskadetka fcnqgrypnq afaeklrnel
 121 svtlpklspq sldvlfqssp ksknqvapew sknairnrly tnwtgkgagt npdehlleia
 181 ediaaeidsd ldgwkdleeh pekglsaadr yfqaqgdfps ltglppsvpl tpqnstvafe
 241 gdpvclnpsd ntllhqavar cagrilqeqp nlspdknrfi nqlqdelvss qnnglswlfg
 301 vgfkywkems vdqladdykv kstdldalkq vksfidaipl nplfdtphyg efrasvagkm
 361 rswvknywkr lldlksqlgt aninlpegld eqraenlfsg llidskglrq vtdklpsrlk
 421 kaedtidrlm gdgnptsddi eqvetvaaei safigqveqf nnqleqrlen plegddetfl
 481 kqlkidlpae fkkppainri sggspdptae iaeleekldr lmsarkehye tiaewasank
 541 vtldpmeamt tleaqrlter gaegdqeefa lrlllqrigr lanrlspqga tairdllrpv
 601 ftekrefnlf fhnrmgslyr spystsrhqp ftidvavakn tdwmdaldgi aetimkglsq
 661 agdelslrlr cwinisqfsl sqrlrglpdt vpgelalvrs addvrippml alqleedevs
 721 revclkafnl yvsaingclf ralregfivr tkfqrlerdv lsyvpktklw nypqrldtar
 781 gpihsalaaa winkegsvid pvetvtalsd tgfsddgipe ylvqaphdwy tpidlrdisk
 841 pvsglpvkkn itglkrqkkq tafrmvgpss fkshldstll seevklgdft lifdqyykqr
 901 vsyngrvkit fepdrlhvea avpvidkrvr psteedalfd hllaidlgek rvgyavydik
 961 aclrtgdikp ledgdgkpiv gsvavpsirr lmkavrshrq qrqpnqkvnq tystalmnyr
1021 envigdvcnr idtlmekyna fpvlessvmn feagsrqlem vygsvlhryt yskidahtak
1081 rkeywytgey wdhpylmahk wnertrsysg slsaltlypq vmvhpagtsq rchqckrnpm
1141 veikqltgqv einadgslel ddgticlyeg ydyspeeykk akrekrrldp nvplsgrhqa
1201 khvsavakrn lrrptvsmms gdttqaryvc lytdcdftgh adenaainig wkylterial
1261 seskdkagv       (SEQ ID NO: 1293)
```

FIG. 8 (Cont.)

GenBank WP_044921188
Lachnospiraceae bacterium MA2020
type VI CRISPR-associated protein C2c2

```
   1 mqiskvnhkh vavgqkdrer itgfiyndpv gdeksledvv akrandtkvl fnvfntkdly
  61 dsqesdksek dkeliskgak fvaksfnsai tilkkqnkiy stltsqqvik elkdkfggar
 121 iydddieeal tetlkksfrk envrnsikvl ienaagirss lskdeeeliq eyfvkqlvee
 181 ytktklqknv vksiknqnmv iqpdsdsqvl slsesrrekq ssavssdtlv nckekdvlka
 241 fltdyavlde dernsllwkl rnlvnlyfyg sesirdysyt keksvwkehd eqkanktlfi
 301 deichitkig kngkeqkvld yeenrsrcrk qninyyrsal nyaknntsgi fenedsnhfw
 361 ihlienever lynqiengee fkfetgyise kvwkavinhl sikyialgka vynyamkels
 421 spgdiepgki ddsyingits fdyeiikaee slqrdismnv vfatnylaca tvdtdkdfll
 481 fskedirsct kkdgnlckni mqfwggystw knfceeylkd dkdalellys lksmlysmrn
 541 ssfhfstenv dngswdteli gklfeedcnr aariekekfy nnnlhmfyss sllekvlerl
 601 ysshherasq vpsfnrvfvr knfpsslseq ritpkftdsk deqiwqsavy ylckeiyynd
 661 flqskeaykl fregvknldk ndinnqkaad sfkqavvyyg kaignatlsq vcqaimteyn
 721 rqnndglkkk sayaekqnsn kykhyplflk qvlqsafwey ldenkeiygf isaqihksnv
 781 eikaedfian yssqqykklv dkvkktpelq kwytlgrlin prqanqflgs irnyvqfvkd
 841 iqrrakengn pirnyyevle sdsiikilem ctklngttsn dihdyfrded eyaeyisqfv
 901 nfgdvhsgaa lnafcnsese gkkngiyydg inpivnrnwv lcklygspdl iskiisrvne
 961 nmihdfhkqe dlireyqikg icsnkkeqqd lrtfqvlknr velrdiveys eiinelygql
1021 ikwcylrerd lmyfqlgfhy lclnnasske adyikinvdd rnisgailyq iaamyinglp
1081 vyykkddmyv alksgkkasd elnsneqtsk kinyflkygn nilgdkkdql ylaglelfen
1141 vaeheniiif rneidhfhyf ydrdrsmldl ysevfdrfft ydmklrknvv nmlynilldh
1201 nivssfvfet gekkvgrgds evikpsakir lranngvssd vftykvgskd elkiatlpak
1261 neefllnvar liyypdmeav senmvregvv kveksndkkg kisrgsntrs snqskynnks
1321 knrmnysmgs ifekmdlkfd     (SEQ ID NO: 1300)
```

FIG. 8 (Cont.)

GenBank WP_022785443.1
Lachnospiraceae bacterium NK4A179
type VI CRISPR-associated protein C2c2

```
   1 mkiskvreen rgakltvnak tavvsenrsq egilyndpsr ygksrknded rdryiesrlk
  61 ssgklyrifn edknkretde lqwflseivk kinrrnglvl sdmlsvddra fekafekyae
 121 lsytnrrnkv sgspafetcg vdaataerlk giisetnfin riknnidnkv sediidriia
 181 kylkkslcre rvkrglkkll mnafdlpysd pdidvqrdfi dyvledfyhv raksqvsrsi
 241 knmnmpvqpe qdgkfaitvs kggtesgnkr saekeafkkf lsdyaslder vrddmlrrmr
 301 rlvvlyfygs ddsklsdvne kfdvwedhaa rrvdnrefik lplenklang ktdkdaerir
 361 kntvkelyrn qnigcyrqav kaveednngr yfddkmlnmf fihrieygve kiyanlkqvt
 421 efkartgyls ekiwkdliny isikyiamgk avynyamdel nasdkkeiel gkiseeylsq
 481 issfdyelik aeemlqreta vyvafaarhl ssqtveldse nsdflllkpk gtmdkndknk
 541 lasnnilnfl kdketlrdti lqyfgqhslw tdfpfdkyla ggkddvdflt dlkdviysmr
 601 ndsfhyaten hnngkwnkel isamfehete rmtvvmkdkf ysnnlpmfyk nddlkkllid
 661 lykdnveras qvpsfnkvfv rknfpalvrd kdnlgieldl kadadkgene lkfynalyym
 721 fkeiyynafl ndknvrerfi tkatkvadny drnkernlkd riksagsdek kklreqlqny
 781 iaendfgqri knivqvnpdy tlaqicqlim teynqqnngc mqkksaarkd inkdsyqhyk
 841 mlllvnlrka flefikenya fvlkpykhdl cdkadfvpdf akyvkpyagl isrvagssel
 901 qkwyivsrfl spaqanhmlg flhsykqyvw diyrrasetg teinhsiaed kiagvditdv
 961 davidlsvkl cgtisseisd yfkddevyae yissyldfey dggnykdsln rfcnsdavnd
1021 qkvalyydge hpklnrniil sklygerrfl ekitdrvsrs diveyyklkk etsqyqtkgi
1081 fdsedeqkni kkfqemkniv efrdlmdyse iadelqgqli nwiylrerdl mnfqlgyhya
1141 clnndsnkqa tyvtldyqgk knrkingail yqicamying lplyyvdkds sewtvsdgke
1201 stgakigefy ryaksfents dcyasgleif enisehdnit elrnyiehfr yyssfdrsfl
1261 giysevfdrf ftydlkyrkn vptilynill qhfvnvrfef vsgkkmigid kkdrkiakek
1321 ecaritirek ngvyseqfty klkngtvyvd ardkrylqsi irllfypekv nmdemievke
1381 kkkpsdnntg kgyskrdrqq drkeydkyke kkkkegnfls gmggninwde inaqikn
```

(SEQ ID NO: 1301)

FIG. 8 (Cont.)

GenBank WP_031473346.1
Clostridium aminophilum
type VI CRISPR-associated protein C2c2

```
   1 mkfskvdhtr savgiqkatd svhgmlytdp kkqevndldk rfdqlnvkak rlynvfnqsk
  61 aeedddekrf gkvvkklnre kdllfhrev srynsignak ynyygiksnp eeivsnlgmv
 121 eslkgerdpq kvisklllyy lrkglkpgtd glrmileasc glrklsgdek elkvflqtld
 181 edfekktfkk nlirsienqn mavqpsnegd piigitqgrf nsqkneeksa iermmsmyad
 241 lnedhredvl rklrrlnvly fnvdtektee ptlpgevdtn pvfevwhdhe kgkendrqfa
 301 tfakiltedr etrkkeklav kealndlksa irdhnimayr csikvteqdk dqlffedqri
 361 nrfwihhies averilasin peklyklrig ylgekvwkdl lnylsikyia vgkavfhfam
 421 edlgktgqdi elgklsnsvs ggltsfdyeq iradetlqrq lsvevafaan nlfravvgqt
 481 gkkieqskse eneedfllwk aekiaesikk egegntlksi lqffggassw dlnhfcaayg
 541 nessalgyet kfaddlrkai yslrnetfhf ttlnkgsfdw nakligdmfs heaatgiave
 601 rtrfysnnlp mfyresdlkr imdhlyntyh prasqvpsfn svfvrknfrl flsntlntnt
 661 sfdtevyqkw esgvyylfke iyynsflpsg dahhlffegl rrirkeadnl pivgkeakkr
 721 navqdfgrrc delknlslsa icqmimteyn eqnngnrkvk stredkrkpd ifqhykmlll
 781 rtlqeafaiy irreefkfif dlpktlyvmk pveeflpnwk sgmfdslver vkqspdlqrw
 841 yvlckflngr llnqlsgvir syiqfagdiq rrakanhnrl ymdntqrvey ysnvlevvdf
 901 cikgtsrfsn vfsdyfrded ayadyldnyl qfkdekiaev ssfaalktfc neeevkagiy
 961 mdgenpvmqr nivmaklfgp devlknvvpk vtreeieeyy qlekqiapyr qngyckseed
1021 qkkllrfqri knrvefqtit efseiinell gqliswsflr erdllyfqlg fhylclhndt
1081 ekpaeykeis redgtvirna ilhqvaamyv gglpvytlad kklaafekge adcklsiskd
1141 tagagkkikd ffryskyvli kdrmltdqnq kytiylagle lfentdehdn itdvrkyvdh
1201 fkyyatsden amsildlyse ihdrfftydm kyqknvanml enillrhfvl irpefftgsk
1261 kvgegkkitc karaqieiae ngmrsedfty klsdgkknis tcmiaardqk ylntvarlly
1321 ypheakksiv dtrekknnkk tnrgdgtfnk gkgtarkekd ngprefndtg fsntpfagfd
1381 pfrns    (SEQ ID NO: 1302)
```

FIG. 8 (Cont.)

GenBank WP_027114339.1
Lachnospiraceae bacterium NK4A144
type VI CRISPR-associated protein C2c2

```
   1 mkiskvdhtr mavakgnqhr rdeisqilyk dptktgsidf derfkklncs akilyhvfng
  61 iaegsnkykn ivdkvnnnld rvlftgksyd rksiididtv lrnvekinaf dristeereq
 121 iiddlleiql rkglrkgkag lrevlligag vivrtdkkqe iadfleilde dfnktnqakn
 181 iklsienqgl vvspvsrgee rifdvsgaqk gksskkaqek ealsaflldy adldknvrfe
 241 ylrkirrlin lyfvknddv mslteipaev nlekdfdiwr dheqrkeeng dfvgcpdill
 301 adrdvkksns kqvkiaerql resireknik ryrfsiktie kddgtyffan kqisvfwihr
 361 ienaverilg sindkklyrl rlgylgekvw kdilnflsik yiavgkavfn famddlqekd
 421 rdiepgkise navngltsfd yeqikademl qrevavnvaf aannlarvtv dipqngeked
 481 illwnksdik kykknskkgi lksilqffgg astwnmkmfe iayhdqpgdy eenylydiiq
 541 iiyslrnksf hfktydhgdk nwnreligkm iehdaervis verekfhsnn lpmfykdadl
 601 kkildllysd yagrasqvpa fntvlvrknf peflrkdmgy kvhfnnpeve nqwhsavyyl
 661 ykeiyynlfl rdkevknlfy tslknirsev sdkkqklasd dfasrceeie drslpeicqi
 721 imteynaqnf gnrkvksqrv ieknkdifrh ykmlliktla gafslylkqe rfafigkatp
 781 ipyettdvkn flpewksgmy asfveeiknn ldlqewyivg rflngrmlnq lagslrsyiq
 841 yaedierraa enrnklfskp dekieackka vrvldlciki strisaeftd yfdseddyad
 901 ylekylkyqd daikelsgss yaaldhfcnk ddlkfdiyvn agqkpilqrn ivmaklfgpd
 961 nilsevmekv tesaireyyd ylkkvsgyrv rgkcstekeq edllkfqrlk navefrdvte
1021 yaevinellg qliswsylre rdllyfqlgf hymclknksf kpaeyvdirr nngtiihnai
1081 lyqivsmyin gldfyscdke gktlkpietg kgvgskigqf ikysqylynd psykleiyna
1141 glevfenide hdnitdlrky vdhfkyyayg nkmslldlys effdrfftyd mkyqknvvnv
1201 lenillrhfv ifypkfgsgk kdvgirdckk eraqieiseq sltsedfmfk lddkageeak
1261 kfparderyl qtiakllyyp neiedmnrfm kkgetinkkv qfnrkkkitr kqknnssnev
1321 lsstmgylfk nikl  (SEQ ID NO: 1303)
```

FIG. 8 (Cont.)

GenBank WP_034560163.1
Carnobacterium gallinarum
type VI CRISPR-associated protein C2c2

```
   1 mritkvkikl dnklyqvtmq keekygtlkl neesrkstae ilrlkkasfn ksfhsktins
  61 qkenknatik kngdyisqif eklvgvdtnk nirkpkmslt dlkdlpkkdl alfikrkfkn
 121 ddiveiknld lislfynalq kvpgehftde swadfcqemm pyreyknkfi erkiillans
 181 ieqnkgfsin petfskrkrv lhqwaievqe rgdfsildek lsklaeiynf kkmckrvqde
 241 lndleksmkk gknpekekea ykkqknfkik tiwkdypykt higliekike neelnqfnie
 301 igkyfehyfp ikkerctede pyylnsetia ttvnyqlkna lisylmqigk ykqfglenqv
 361 ldskklqeig iyegfqtkfm dacvfatssl kniiepmrsg dilgkrefke aiatssfvny
 421 hhffpyfpfe lkqmkdrese lipfgeqtea kqmqniwalr gsvqqirnei fhsfdknqkf
 481 nlpqldksnf efdasenstg ksqsyietdy kflfeaeknq leqffierik ssgaleyypl
 541 kslekLfakk emkfslqsqv vafapsykkl vkkghsyqta tegtanylgl syynryelke
 601 esfqaqyyll kliyqyvflp nfsqgnspaf retvkailri nkdearkkmk knkkflrkya
 661 feqvremefk etpdqymsyl qsemreekvr kaekndkgfe knitmnfekl lmqifvkgfd
 721 vflttfagke lllsseekvi keteislskk inerektlka siqvehqlva tnsaisywlf
 781 cklldsrhln elrnemikfk qsrikfnhtq haeliqnllp iveltilsnd ydekndsqnv
 841 dvsayfedks lyetapyvqt ddrtrvsfrp ilklekyhtk slieallkdn pqfrvaatdi
 901 qewmhkreei gelvekrknl htewaegqqt lgaekreeyr dyckkidrfn wkankvtlty
 961 lsqlhylitd llgrmvgfsa lferdlvyfs rsfselgget yhisdyknls gvlrlnaevk
1021 pikiknikvi dneenpykgn epevkpfldr lhaylenvig ikavhgkirn qtahlsvlql
1081 elsmiesmnn lrdlmaydrk lknavtksmi kildkhgmil klkidenhkn feieslipke
1141 iihlkdkaik tnqvseeycq lvlallttnp gnqln     (SEQ ID NO: 1304)
```

FIG. 8 (Cont.)

GenBank WP_013443710.1
Paludibacter propionicigenes
type VI CRISPR-associated protein C2c2

```
   1  mrvskvkvkd  ggkdkmvlvh  rkttgaqlvy  sgqpvsnets  nilpekkrqs  fdlstlnkti
  61  ikfdtakkqk  lnvdqykive  kifkypkqel  pkqikaeeil  pflnhkfqep  vkywknqkee
 121  sfnltllive  avqaqdkrkl  qpyydwktwy  iqtksdllkk  siennridlt  enlskrkkal
 181  laweteftas  gsidlthyhk  vymtdvlckm  lqdvkpltdd  kgkintnayh  rglkkalqnh
 241  qpaifgtrev  pneanradnq  lsiyhlevvk  ylehyfpikt  skrrntaddi  ahylkaqtlk
 301  ttiekqlvna  iraniiqqgk  tnhhelkadt  tsndlirikt  neafvlnltg  tcafaannir
 361  nmvdneqtnd  ilgkgdfiks  llkdntnsql  ysfffgegls  tnkaeketql  wgirgavqqi
 421  rnnvnhykkd  alktvfnisn  fenptitdpk  qqtnyadtiy  karfinelek  ipeafaqqlk
 481  tggavsyyti  enlkslltlf  qfslcrstip  fapgfkkvfn  gginyqnakq  desfyelmle
 541  qylrkenfae  esynaryfml  kliynnlflp  gfttdrkafa  dsvgfvqmqn  kkqaekvnpr
 601  kkeayafeav  rpmtaadsia  dymayvqsel  mqeqnkkeek  vaeetrinfe  kfvlqvfikg
 661  fdsflrakef  dfvqmpqpql  tatasnqqka  dklnqleasi  tadckltpqy  akaddathia
 721  fyvfcklldа  ahlsnlrnel  ikfresvnef  kfhhlleiie  icllsadvvp  tdyrdlysse
 781  adclarlrpf  ieqgaditnw  sdlfvqsdkh  spvihaniel  svkygttkll  eqiinkdtqf
 841  ktteanftaw  ntaqksieql  ikqredhheq  wvkaknaddk  ekqerkreks  nfaqkfiekh
 901  gddyldicdy  intynwldnk  mhfvhlnrlh  gltiellgrm  agfvalfdrd  fqffdeqqia
 961  defklhgfvn  lhsidkklne  vptkkikeiy  dirnkiiqin  gnkinesvra  nliqfisskr
1021  nyynnaflhv  sndeikekqm  ydirnhiahf  nyltkdaadf  slidlinelr  ellhydrklk
1081  navskafidl  fdkhqmilkl  klnadhklkv  eslepkkiyh  lgssakdkpe  yqyctnqvmm
1141  aycnmcrsll  emkk
```

(SEQ ID NO: 1305)

FIG. 8 (Cont.)

GenBank WP_012985477.1
Listeria seeligeri
type VI CRISPR-associated protein C2c2

```
   1 mwisiktlih hlgvlffcdy mynrrekkii evktmritkv evdrkkvlis rdknggklvy
  61 enemqdnteq imhhkkssfy ksvvnkticr peqkqmkklv hgllqensqe kikvsdvtkl
 121 nisnflnhrf kkslyyfpen spdkseeyri einlsqlled slkkqqgtfi cwesfskdme
 181 lyinwaenyi ssktklikks irnnriqste srsgqlmdry mkdilknknp fdiqsvseky
 241 qlekltsalk atfkeakknd keinyklkst lqnherqiie elkenselnq fnieirkhle
 301 tyfpikktnr kvgdirnlei geiqkivnhr lknkivqril qegklasyei estvnsnslq
 361 kikieeafal kfinaclfas nnlrnmvypv ckkdilmige fknsfkeikh kkfirqwsqf
 421 fsqeitvddi elaswglrga iapirneiih lkkhswkkff nnptfkvkks kiingktkdv
 481 tseflyketl fkdyfyseld svpeliinkm esskildyys sdqlnqvfti pnfelsllts
 541 avpfapsfkr vylkgfdyqn qdeaqpdynl klniynekaf nseafqaqys lfkmvyyqvf
 601 lpqfttnndl fkssvdfilt lnkerkgyak afqdirkmnk dekpseymsy iqsqlmlyqk
 661 kqeekekinh fekfinqvfi kgfnsfiekn rltyichptk ntvpendnie ipfhtdmdds
 721 niafwlmckl ldakqlselr nemikfscsl qsteeistft kareviglal lngekgcndw
 781 kelfddkeaw kknmslyvse ellqslpytq edgqtpvinr sidlvkkygt etileklfss
 841 sddykvsakd iaklheydvt ekiaqqeslh kqwiekpgla rdsawtkkyq nvindisnyq
 901 waktkveltq vrhlhqltid llsrlagyms iadrdfqfss nyilerense yrvtswills
 961 enknknkynd yelynlknas ikvsskndpq lkvdlkqlrl tleylelfdn rlkekrnnis
1021 hfnylngqlg nsilelfdda rdvlsydrkl knavskslke ilsshgmevt fkplyqtnhh
1081 lkidklqpkk ihhlgekstv ssnqvsneyc qlvrtlltmk
```

(SEQ ID NO: 1306)

FIG. 8 (Cont.)

GenBank WP_036091002.1
Listeria newyorkensis
type VI CRISPR-associated protein C2c2

```
   1 mkitkmrvdg rtivmertsk egqlgyegid gnktteiifd kkkesfyksi lnktvrkpde
  61 keknrrkqai nkainkeite lmlavlhqev psqklhnlks lntesltklf kpkfqnmisy
 121 ppskgaehvq fcltdiavpa irdldeikpd wgiffeklkp ytdwaesyih ykqttiqksi
 181 eqnkiqspds prklvlqkyv taflngeplg ldlvakkykl adlaesfklv dlnedksany
 241 kikaclqqhq rnildelked pelnqygiev kkyiqryfpi krapnrskha radflkkeli
 301 estveqqfkn avyhvleqg kmeayeltdp ktkdlqdirs geafsfkfin acafasnnlk
 361 milnpecekd ilgkgnfkkn lpnsttrsdv vkkmipffsd elqnvnfdea iwairgsiqq
 421 irnevyhckk hswksilkik gfefepnnmk yadsdmqklm dkdiakipef ieeklkssgv
 481 vrfyrhdelq siwemkqgfs llttnapfvp sfkrvyakgh dyqtsknryy nldlttfdil
 541 eygeedfrar yfltklvyyq qfmpwftadn nafrdaanfv lrlnknrqqd akafinirev
 601 eegemprdym gyvqgqiaih edsiedtpnh fekfisqvfi kgfdrhmrsa nlkfiknprn
 661 qgleqseiee msfdikveps flknkddyia fwifckmlda rhlselrnem ikydghltge
 721 qeiiglallg vdsrendwkq ffssereyek imkgyvveel yqrepyrqsd gktpilfrgv
 781 eqarkygtet viqrlfdanp efkvskcnla ewerqketie etikrrkelh newaknpkkp
 841 qnnaffkeyk eccdaidayn whknkttlay vnelhhllie ilgryvgyva iadrdfqcma
 901 nqyfkhsgit erveywgdnr lksikkldtf lkkeglfvse knarnhiahl nylslksect
 961 llylserlre ifkydrklkn avskslidil drhgmsvvfa nlkenkhrlv ikslepkklr
1021 hlggkkidgg yietnqvsee ycgivkrlle m
```

(SEQ ID NO: 1307)

FIG. 8 (Cont.)

GenBank ERK53440.1
Leptotrichia wadei F0279
type VI CRISPR-associated protein C2c2

```
   1 mymkitkidg vshykkqdkg ilkkkwkdld erkqrekiea rynkqieski ykeffrlknk
  61 kriekeedqn ikslyffike lylnekneew elkninleil ddkervikgy kfkedvyffk
 121 egykeyylri lfnnliekvq nenrekvrkn kefldlkeif kkyknrkidl llksinnnki
 181 nleykkenvn eeiyginptn dremtfyell keiiekkdeq ksileekldn fditnfleni
 241 ekifneetei niikgkvlne lreyikekee nnsdnklkqi ynlelkkyie nnfsykkqks
 301 kskngkndyl ylnflkkimf ieevdekkei nkekfknkin snfknlfvqh ildygkllyy
 361 kendeyiknt gqletkdley iktketlirk mavlvsfaan syynlfgrvs gdilgtevvk
 421 ssktnvikvg shifkekmln yffdfeifda nkiveilesi sysiynvrng vghfnklilg
 481 kykkkdintn krieedlnnn eeikgyfikk rgeierkvke kflsnnlqyy yskekienyf
 541 evyefeilkr kipfapnfkr iikkgedlfn nknnkkyeyf knfdknsaee kkeflktrnf
 601 llkelyynnf ykeflskkee fekivlevke ekksrgninn kksgvsfqsi ddydtkinis
 661 dyiasihkke mervekynee kqkdtakyir dfveeifltg finylekdkr lhflkeefsi
 721 lcnnnnnvvd fninineeki keflkendsk tlnlylffnm idskrisefr nelvkykqft
 781 kkrldeekef lgikielyet liefviltre kldtkkseei dawlvdklyv kdsneykeye
 841 eilklfvdek ilsskeapyy atdnktpill snfektrkyg tqsflseiqs nykyskveke
 901 niedynkkee ieqkkksnie klqdlkvelh kkweqnkite keiekynntt rkineynylk
 961 nkeelqnvyl lhemlsdlla rnvaffnkwe rdfkfiviai kqflrendke kvneflnppd
1021 nskgkkvyfs vskykntven idgihknfmn liflnnkfmn rkidkmncai wvyfrnyiah
1081 flhlhtknek islisqmnll iklfsydkkv qnhilkstkt llekyniqin feisndknev
1141 fkykiknrly skkgkmlgkn nkfeilenef lenvkamley se
```

(SEQ ID NO: 1308)

FIG. 8 (Cont.)

GenBank WP_023911507.1
Rhodobacter capsulatus
type VI CRISPR-associated protein C2c2

```
   1 mqigkvqgrt isefgdpagg lkrkistdgk nrkelpahls sdpkaligqw isgidkiyrk
  61 pdsrksdgka ihsptpskmq fdarddlgea fwklvseagl aqdsdydqfk rrlhpygdkf
 121 qpadsgaklk feadppepqa fhgrwygams krgndakela aalyehlhvd ekridgqpkr
 181 npktdkfapg lvvaralgie ssvlprgmar larnwgeeei qtyfvvdvaa svkevakaav
 241 saaqafdppr qvsgrslspk vgfalaehle rvtgskrcsf dpaagpsvla lhdevkktyk
 301 rlcargknaa rafpadktel lalmrhthen rvrnqmvrmg rvseyrgqqa gdlaqshywt
 361 sagqteikes eifvrlwvga falagrsmka widpmgkivn tekndrdlta avnirqvisn
 421 kemvaeamar rgiyfgetpe ldrlgaegne gfvfallryl rgcrnqtfhl garagflkei
 481 rkelektrwg kakeaehvvl tdktvaaira iidndakalg arlladlsga fvahyaskeh
 541 fstlyseivk avkdapevss glprlklllk radgvrgyvh glrdtrkhaf atklppppap
 601 relddpatka ryiallrlyd gpfrayasgi tgtalagpaa rakeaatala qsvnvtkays
 661 dvmegrssrl rppndgetlr eylsaltget atefrvqigy esdsenarkq aefienyrrd
 721 mlafmfedyi rakgfdwilk iepgatamtr apvlpepidt rgqyehwqaa lylvmhfvpa
 781 sdvsnllhql rkwealqgky elvqdgdatd qadarreald lvkrfrdvlv lflktgearf
 841 egraapfdlk pfralfanpa tfdrlfmatp ttarpaeddp egdgasepel rvartlrglr
 901 qiarynhmav lsdlfakhkv rdeevarlae iedetqeksq ivaaqelrtd lhdkvmkchp
 961 ktispeerqs yaaaiktiee hrflvgrvyl gdhlrlhrlm mdvigrlidy agayerdtgt
1021 flinaskqlg agadwavtia gaantdartq trkdlahfnv ldradgtpdl talvnrarem
1081 maydrkrkna vprsildmla rlgltlkwqm kdhllqdati tqaaikhldk vrltvggpaa
1141 vtearfsqdy lqmvaavfng svqnpkpgrrr ddgdawhkpp kpataqsqpd qkppnkapsa
1201 gsrlpppqvg evyegvvvkv idtgslgfla vegvagnigl hisrlrrire daiivgrryr
1261 frveiyvppk sntsklnaad lvrid
```
(SEQ ID NO: 1309)

FIG. 8 (Cont.)

GenBank WP_015770004.1
Leptotrichia buccalis
type VI CRISPR-associated protein C2c2

```
   1 mkvtkvggis hkkytsegrl vkseseenrt derlsallnm rldmyiknps stetkenqkr
  61 igklkkffsn kmvylkdntl slkngkkeni dreysetdil esdvrdkknf avlkkiylne
 121 nvnseelevf rndikkklnk inslkysfek nkanyqkine nniekvegks krniiydyyr
 181 esakrdayvs nvkeafdkly keediaklvl eienltklek ykirefyhei igrkndkenf
 241 akiiyeeiqn vnnmkeliek vpdmselkks qvfykyyldk eelndkniky afchfveiem
 301 sqllknyvyk rlsnisndki krifeyqnlk klienkllnk ldtyvrncgk ynyylqdgei
 361 atsdfiarnr qneaflrnii gvssvayfsl rniletenen ditgrmrgkt vknnkgeeky
 421 vsgevdkiyn enkknevken lkmfysydfn mdnkneiedf fanideaiss irhgivhfnl
 481 elegkdifaf kniapseisk kmfqneinek klklkifrql nsanvfryle kykilnylkr
 541 trfefvnkni pfvpsftkly sriddlknsl giywktpktn ddnktkeiid aqiyllkniy
 601 ygeflnyfms nngnffeisk eiielnkndk rnlktgfykl qkfediqeki pkeylaniqs
 661 lyminagnqd eeekdtyidf iqkiflkgfm tylanngrls liyigsdeet ntslaekkqe
 721 fdkflkkyeq nnnikipyei neflreiklg nilkyterln mfylilkllr hkeltnlkgs
 781 lekyqsanke eafsdqleli nllnldnnrv tedfeleade igkfldfngn kvkdnkelkk
 841 fdtnkiyfdg eniikhrafy nikkygmlnl lekiadkagy kisieelkky snkkneiekn
 901 hkmqenlhrk yarprkdekf tdedyesykq aienieeyth lknkvefnel nllqglllri
 961 lhrlvgytsi werdlrfrlk qefpenqyie eifnfenkkn vkykggqive kyikfykelh
1021 qndevkinky ssanikvlkq ekkdlyirny iahfnyipha eisllevien lrkllsydrk
1081 lknavmksvv dilkeygfva tfkigadkki giqtleseki vhlknlkkkk lmtdrnseel
1141 cklvkimfey kmeekksen
```
(SEQ ID NO: 1310)

FIG. 8 (Cont.)

GenBank WP_018451595.1
Leptotrichia shahii
type VI CRISPR-associated protein C2c2

```
   1 mgnlfghkrw yevrdkkdfk ikrkvkvkrn ydgnkyilni nennnkekid nnkfirkyin
  61 ykkndnilke ftrkfhagni lfklkgkegi irienndffl eteevvlyie aygkseklka
 121 lgitkkkiid eairqgitkd dkkieikrqe neeeieidir deytnktlnd csiilriien
 181 deletkksiy eifkninmsl ykiiekiien etekvfenry yeehlrekll kddkidvilt
 241 nfmeirekik snleilgfvk fylnvggdkk ksknkkmlve kilninvdlt vediadfvik
 301 elefwnitkr iekvkkvnne flekrrnrty iksyvlldkh ekfkierenk kdkivkffve
 361 niknnsikek iekilaefki delikkleke lkkgncdtei fgifkkhykv nfdskkfskk
 421 sdeekelyki iyrylkgrie kilvneqkvr lkkmekieie kilnesilse kilkrvkqyt
 481 lehimylgkl rhndidmttv ntddfsrlha keeldlelit ffastnmeln kifsreninn
 541 denidffgqd reknyvldkk ilnskikiir dldfidnknn itnnfirkft kigtnernri
 601 lhaiskerdl qgtqddynkv iniiqnlkis deevskalnl dvvfkdkkni itkindikis
 661 eennndikyl psfskvlpei lnlyrnnpkn epfdtietek ivlnaliyvn kelykklile
 721 ddleeneskn iflqelkktl gnideideni ienyyknaqi saskgnnkai kkyqkkviec
 781 yigylrknye elfdfsdfkm niqeikkqik dindnktyer itvktsdkti vinddfeyii
 841 sifallnsna vinkirnrff atsvwlntse yqniidilde imqlntlrne citenwnlnl
 901 eefiqkmkei ekdfddfkiq tkkeifnnyy ediknnilte fkddingcdv lekklekivi
 961 fddetkfeid kksnilqdeq rklsninkkd lkkkvdqyik dkdqeikski lcriifnsdf
1021 lkkykkeidn liedmesene nkfqeiyypk erknelyiyk knlflnignp nfdkiyglis
1081 ndikmadakf lfnidgknir knkiseidai lknlndklng yskeykekyi kklkenddff
1141 akniqnknyk sfekdynrvs eykkirdlve fnylnkiesy lidinwklai qmarferdmh
1201 yivnglrelg iiklsgyntg israypkrng sdgfytttay ykffdeesyk kfekicygfg
1261 idlsensein kpenesirny ishfyivrnp fadysiaeqi drvsnllsys trynnstyas
1321 vfevfkkdvn ldydelkkkf klignndile rlmkpkkvsv lelesynsdy iknliiellt
1381 kientndtl
```

(SEQ ID NO: 1311)

FIG. 9
Hippocampus
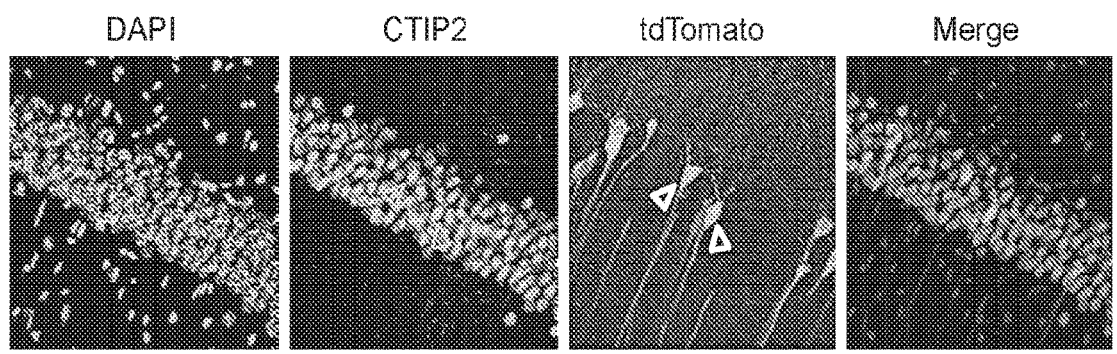
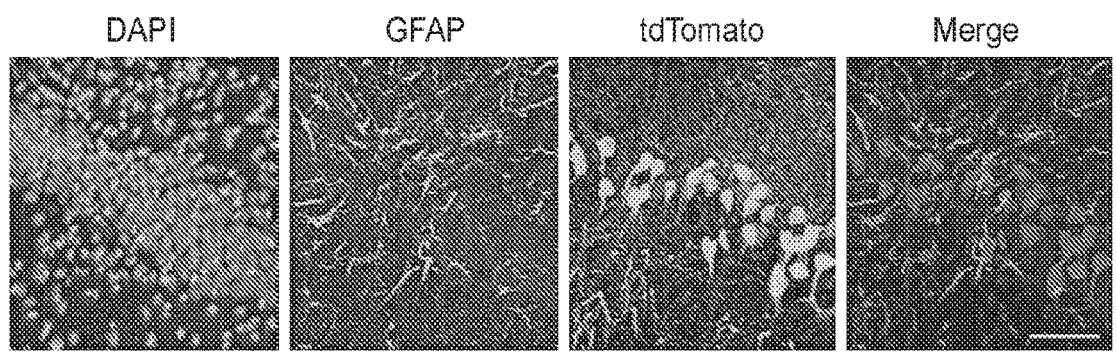
Striatum
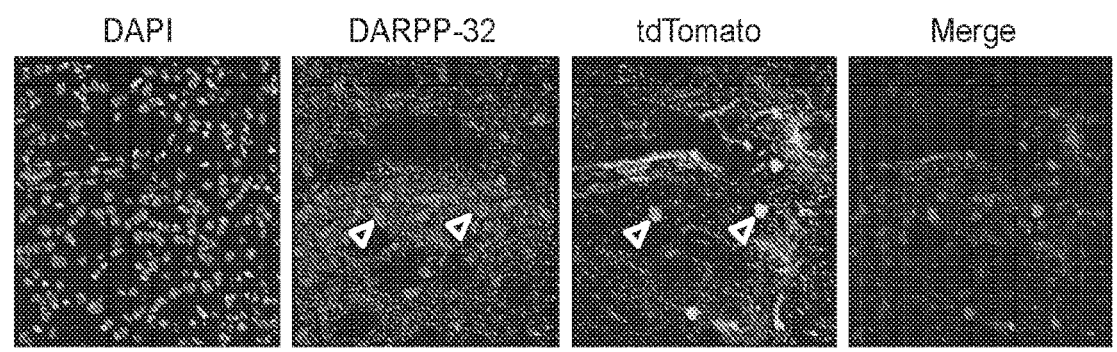
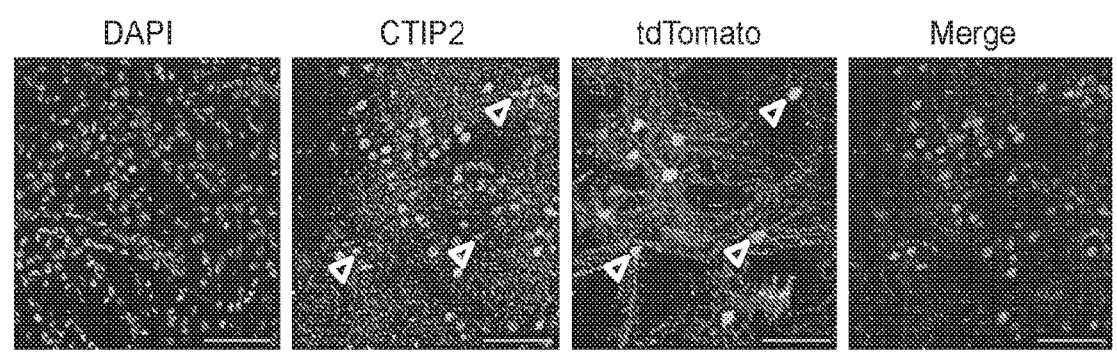

FIG. 10B
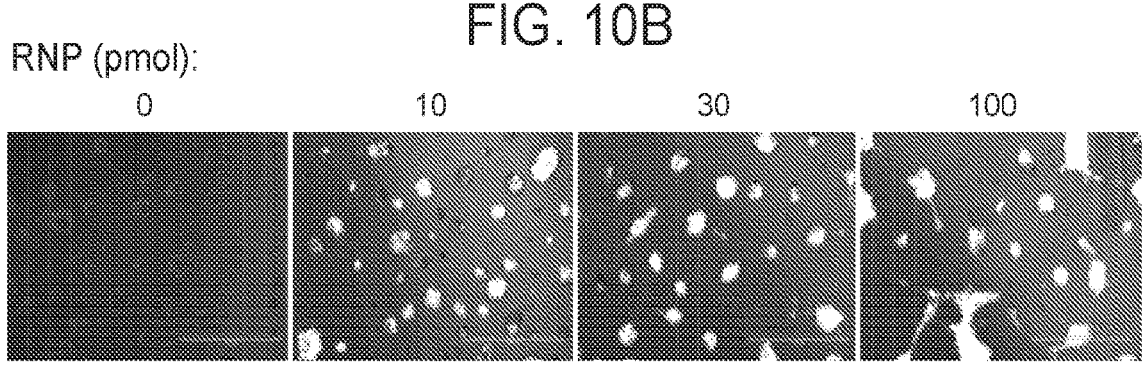
FIG. 10C
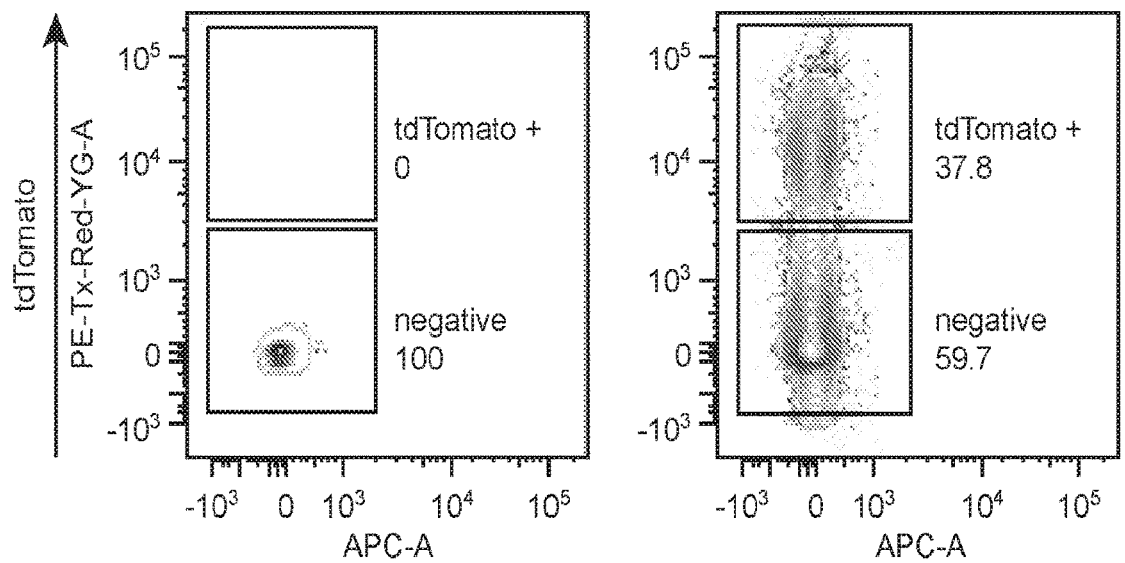
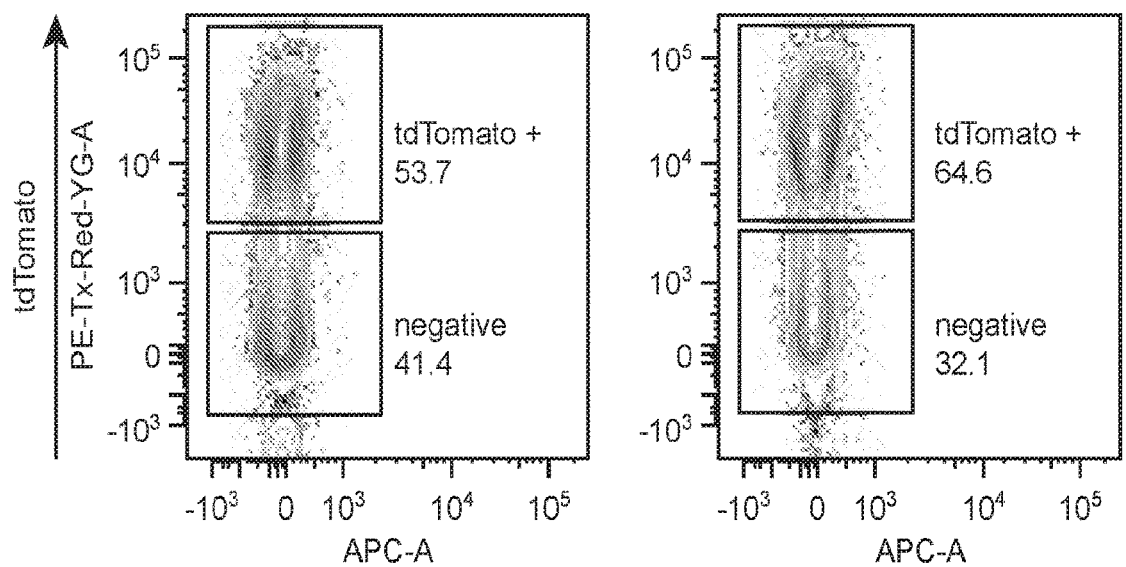

FIG. 11B

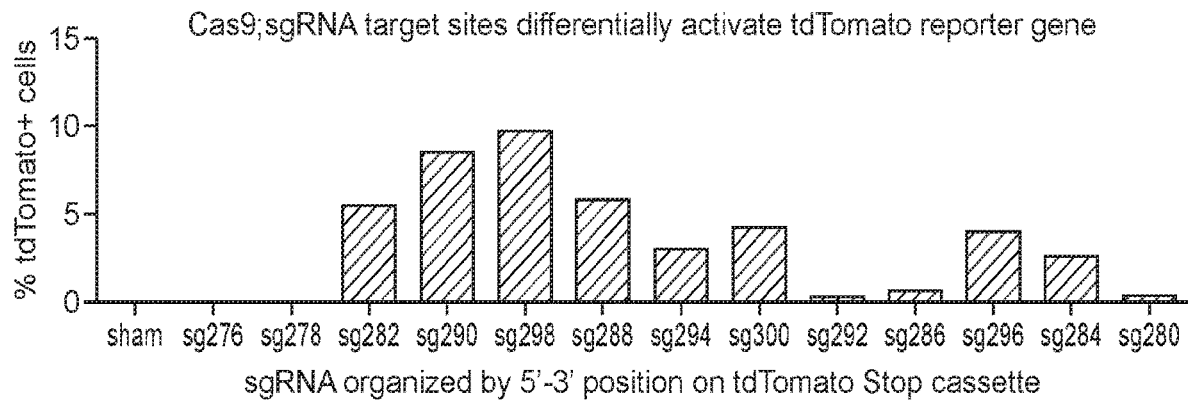

FIG. 11C

| sgRNA# | score | guide | PAM | # target sites | %tdTomato+ cells |
|---|---|---|---|---|---|
| sham | - | - | - | - | 0 |
| sg276 | 85 | CAATAACAAGCACGTTGCCC | AGG | 1X | 0 |
| sg278 | 84 | TAGGAACTTCTTAGGGCCCG | CGG | 1X | 0 |
| sg282 | 73 | CAGCCATACCACATTTGTAG | AGG | 3X | 5.4 |
| sg290 | 63 | AAACCTCTACAAATGTGGTA | TGG | 3X | 8.5 |
| sg298 | 54 | AAGTAAAACCTCTACAAATG | TGG | 3X | 9.7 |
| sg288 | 65 | TATGTTTCAGGTTCAGGGGG | AGG | 3X | 5.8 |
| sg294 | 57 | TTTTATGTTTCAGGTTCAGG | GGG | 3X | 2.9 |
| sg300 | 50 | ATTTTATGTTTCAGGTTCAG | GGG | 3X | 4.2 |
| sg292 | 59 | TTGTTTATTGCAGCTTATAA | TGG | 3X | 0.2 |
| sg286 | 66 | TTTTCACTGCATTCTAGTTG | TGG | 3X | 0.6 |
| sg296 | 55 | ATAAGATACATTGATGAGTT | TGG | 3X | 4 |
| sg284 | 68 | TCAATGTATCTTATCATGTC | TGG | 3X | 2.6 |
| sg280 | 79 | GTATGCTATACGAAGTTATT | AGG | 1X | 0.3 |

FIG. 11D

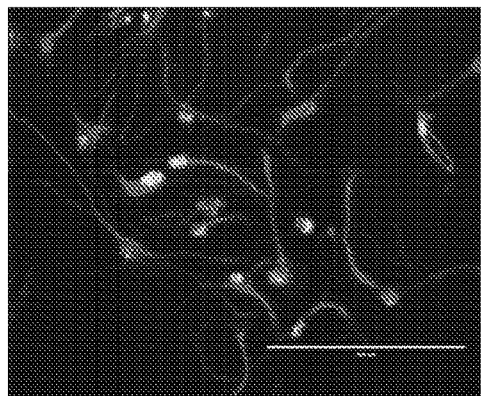

FIG. 14A
Location of intracranial injections
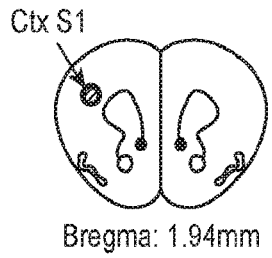
Ctx S1
Bregma: 1.94mm
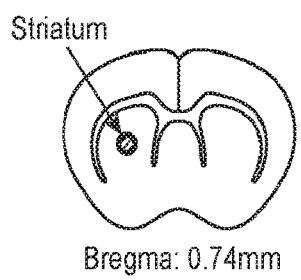
Striatum
Bregma: 0.74mm
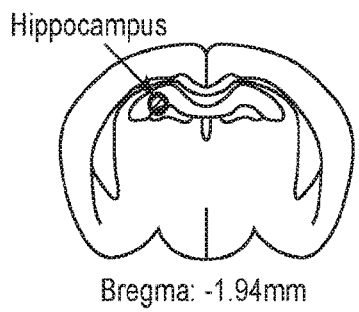
Hippocampus
Bregma: -1.94mm
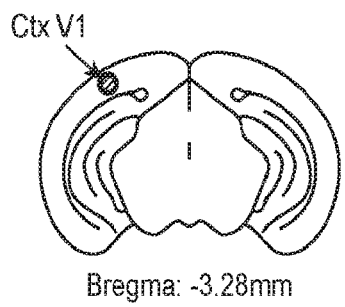
Ctx V1
Bregma: -3.28mm
FIG. 14B
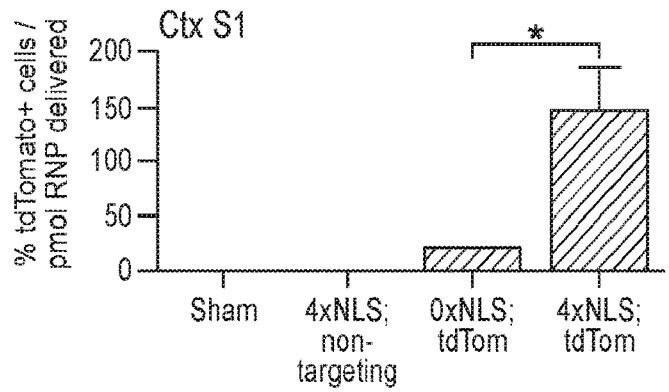
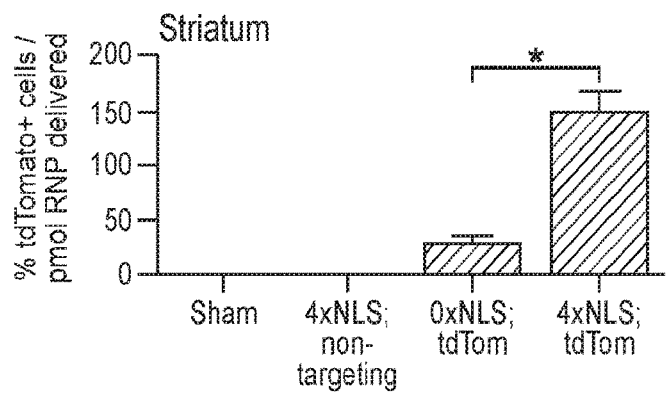
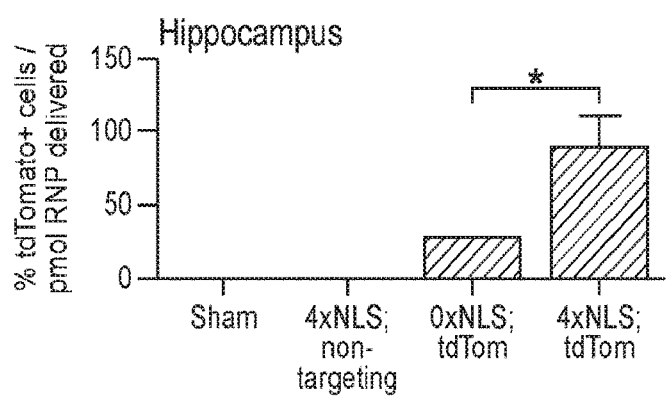
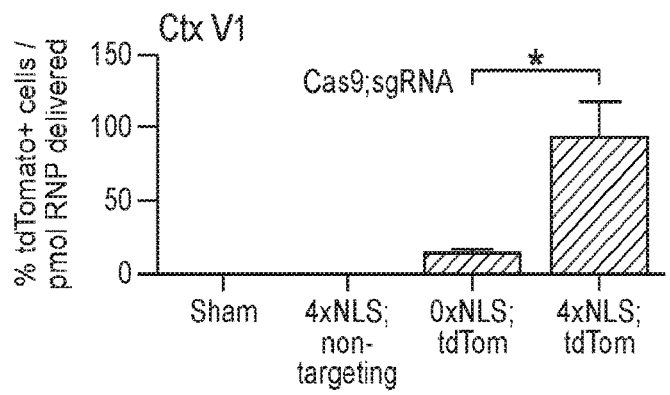

FIG. 17A
Location of bilateral intrastriatal injections
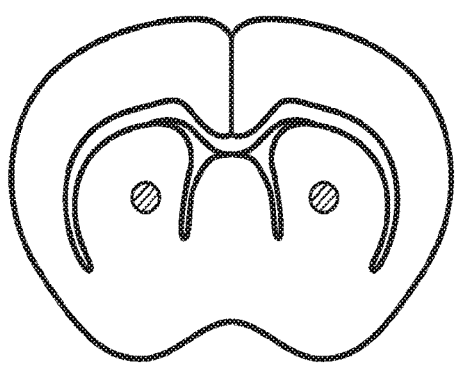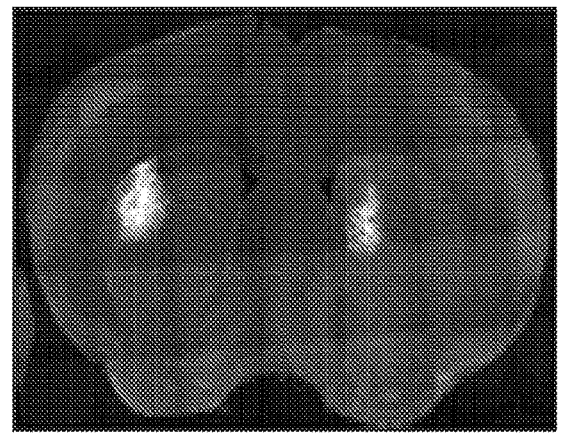
FIG. 17B
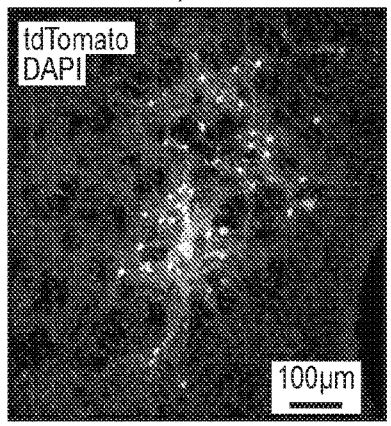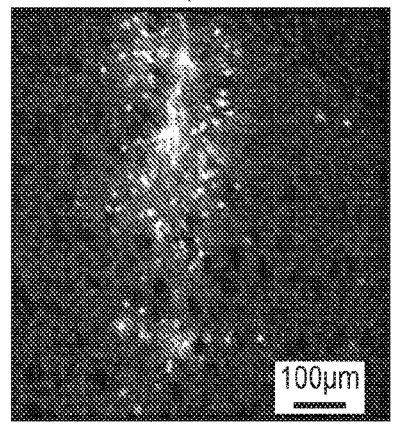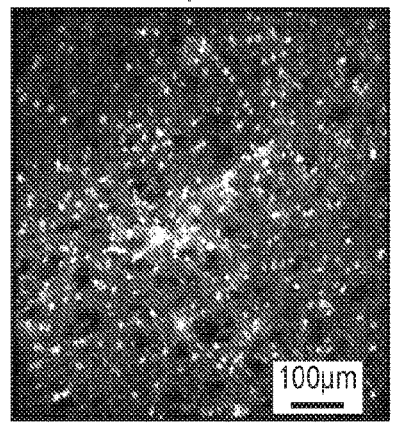

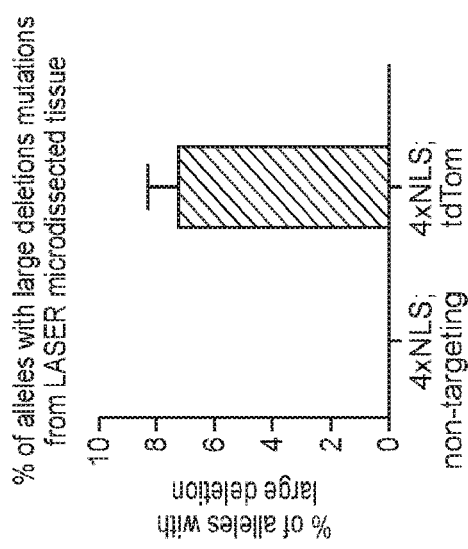
FIG. 17C
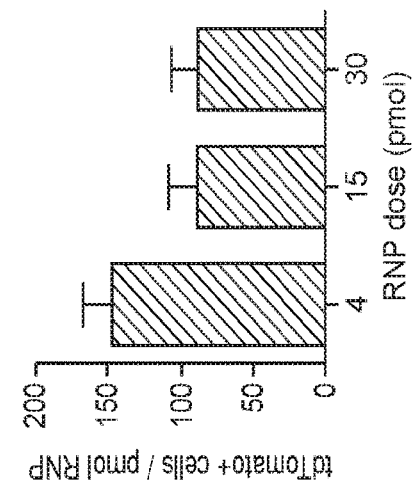
FIG. 17D
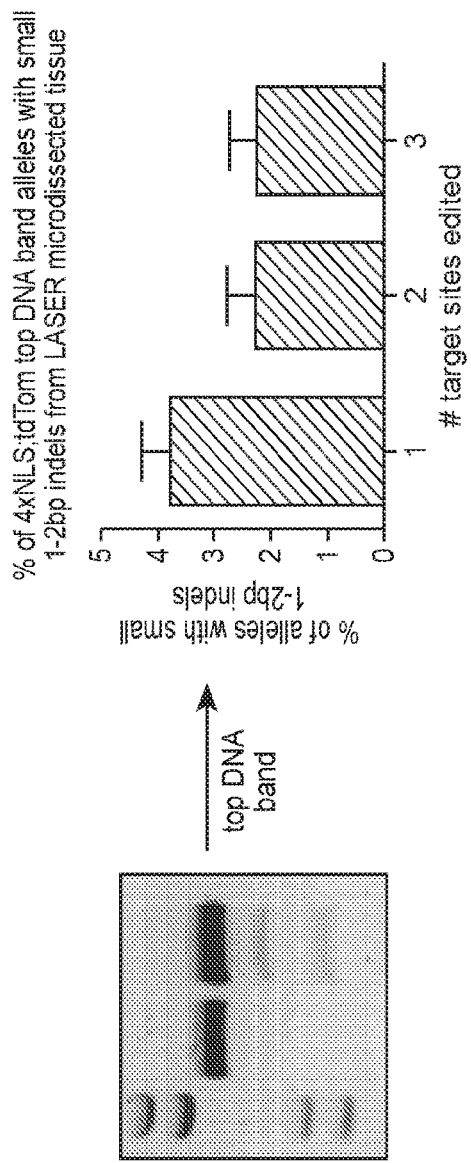
FIG. 17E
FIG. 17F
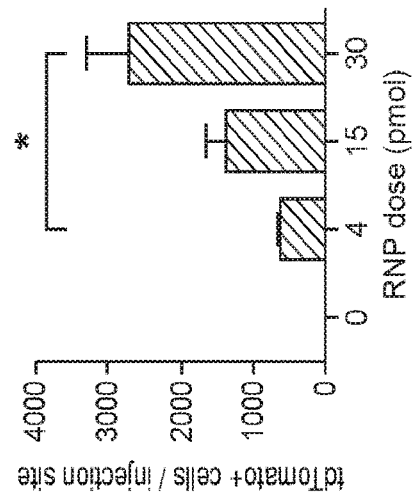

FIG. 18

0xNLS-Cas9;tdTom RNP, +/sense

```
1              10                  20   23
A A G T A A A A C C T C T A C A A A T G N G G    Reads
. . . . . . . . . . . . . . . . . . . . . . .    10
. . . . . . . . . . . . . . . . . . . . . . .    3
. . . . . . . . . . . . . . . . . . . . . . .    2
```

0xNLS-Cas9;tdTom RNP, -/antisense

```
1              10                  20   23
A A G T A A A A C C T C T A C A A A T G N G G    Reads
. . . . . . . . . . . . . . . . . . . . . . .    3
```

4xNLS-Cas9;tdTom RNP, +/sense

```
1              10                  20   23
A A G T A A A A C C T C T A C A A A T G N G G    Reads
. . . . . . . . . . . . . . . . . . . . . . .    22
. . . . . . . . . . . . . . . . . . . . . . .    14
. . . . . . . . . . . . . . . . . . . . . . .    11
```

4xNLS-Cas9;tdTom RNP, -/antisense

```
1              10                  20   23
A A G T A A A A C C T C T A C A A A T G N G G    Reads
. . . . . . . . . . . . . . . . . . . . . . .    11
. . . . . . . . . . . . . . . . . . . . . . .    8
. . . . . . . . . . . . . . . . . . . . . . .    4
```

FIG. 19

TEVscar NLS GGS linker ATG of Cas9 sFGFP

N-terminal NLS DNA sequences

1xNLS:
TCCAATGCCACCCCAAAGAAGAAGCGGAAAGTAGGCATCCACGGAGTCCCAGCAGCTACCATG

2xNLS:
TCCAATGCCACCCCAAAGAAGAAGCGGAAAGTAGGCGGCTCCCCAAGAAGAAGCGGAAAGTAGGTATCCACGGAGT
CCCAGCAGCTACCATG

4xNLS:
TCCAATGCCACCCCAAAGAAGAAGCGGAAAGTGGGTGGGTCCCCCAAGAAGAAGCGGAAAGTAGGCGGCTCCCCAA
AAGAAGAAGCGGAAAGTAGGGGGTAGCCCCAAGAAGAAGCGGAAAGTAGGTATCCACGGAGTCCCAGCAGCTACCATG

7xNLS:
TCCAATGCCACCCCAAAGAAGAAGCGGAAAGTGGGTGGGTCCCCCAAGAAGAAGCGGAAAGTAGGCGGCTCCCCAA
AAGAAGAAGCGGAAAGTAGGGGGTAGCCCCAAGAAGAAGCGGAAAGTAGGTGGTCCCCAAAGAAGAAGCGGAAAGTA
GGCGGCTCCCCAAGAAGAAGCGGAAAGTAGGGGGTAGCCCCAAGAAGAAGCGGAAAGTAGGTATCCACGGAGTCCC
AGCAGCTACCATG

US 11,118,194 B2

MODIFIED SITE-DIRECTED MODIFYING POLYPEPTIDES AND METHODS OF USE THEREOF

CROSS-REFERENCE

This application is a national stage application under 35 U.S.C. § 371 of PCT/US2016/067040, filed Dec. 15, 2016, which claims the benefit of U.S. Provisional Patent Application No. 62/269,755, filed Dec. 18, 2015, which application is incorporated herein by reference in its entirety.

INCORPORATION BY REFERENCE OF SEQUENCE LISTING PROVIDED AS A TEXT FILE

A Sequence Listing is provided herewith as a text file, "BERK-308WO_Seq_List_ST25.txt" created on Dec. 14, 2016 and having a size of 7,986 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, the Cas9 protein functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs).

RNA-programmed Cas9 has proven to be a versatile tool for genome engineering in multiple cell types and organisms. Guided by a dual-RNA complex or a chimeric single-guide RNA, Cas9 (or variants of Cas9 such as nickase variants) can generate site-specific DSBs or single-stranded breaks (SSBs) within target nucleic acids. Target nucleic acids can include double-stranded DNA (dsDNA) and single-stranded DNA (ssDNA) as well as RNA. When cleavage of a target nucleic acid occurs within a cell (e.g., a eukaryotic cell), the break in the target nucleic acid can be repaired by non-homologous end joining (NHEJ) or homology directed repair (HDR).

Thus, the Cas9 system provides a facile means of modifying genomic information. In addition, catalytically inactive Cas9 alone or fused to transcriptional activator or repressor domains can be used to alter transcription levels at sites within target nucleic acids by binding to the target site without cleavage.

SUMMARY

The present disclosure provides modified site-directed modifying polypeptides, and ribonucleoproteins comprising the modified polypeptides. The modified site-directed modifying polypeptides are modified for passive entry into target cells. The modified site-directed modifying polypeptides are useful in a variety of methods for target nucleic acid modification, which methods are also provided.

BRIEF DESCRIPTION OF THE DRAWINGS

FIG. 1A-1G depict amino acid sequences of polypeptides that facilitate crossing a eukaryotic cell membrane. Top to bottom, SEQ ID NOs: 1090-1249.

FIG. 2A-2D depict design (FIG. 2A) and characterization (FIG. 2B-2D) of a fusion site-directed modifying polypeptide according to embodiments of the present disclosure.

FIG. 7A-7B provide the amino acid sequence of a 4×NLS-Cas-2×NLS-sfGFP polypeptide (SEQ ID NO: 1250) (FIG. 7A) and the amino acid sequence of a 4×NLS-Cas-2×NLS polypeptide (SEQ ID NO: 1251)(FIG. 7B).

FIG. 8 provides example amino acid sequences of typeV and typeVI CRISPR/Cas polypeptides.

FIG. 10A-10G depict Cas9 RNP-mediated editing of neural progenitor/stem cells (NPCs).

FIG. 11A-11D provide various information on sgRNAs and NPCs. Sequences in FIG. 11C from top to bottom-SEQ ID NOs:1319-1331.

FIG. 14A-14C depict that injection of Cas9 RNP into multiple brain regions in adult mice results in precise and programmable genome-editing.

FIG. 17A-17F depict that increasing dose of 4×NLS-Cas9 RNP complexes significantly increases the number of tdTomato+ genome-edited cells in the striatum.

FIG. 18 depicts GUIDE-Seq analysis for off-target editing and 0×NLS-Cas9 compared to 4×NLS-Cas9 fidelity. AAGTAAAACCTCTACAAATGNGG is SEQ ID NO:1332.

FIG. 19 provides primary sequences for N-terminal NLS-Cas9 fusions. Sequences from top to bottom-SEQ ID NOs: 1490-1493.

DEFINITIONS

Figure 2C:
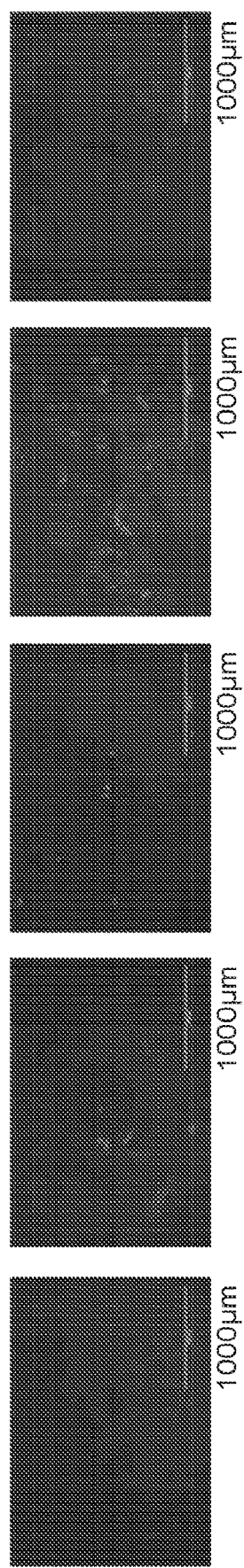

By "site-directed modifying polypeptide" or "site-directed DNA modifying polypeptide" or "site-directed target nucleic acid modifying polypeptide" or "RNA-binding site-directed polypeptide" or "RNA-binding site-directed modifying polypeptide" or "site-directed polypeptide" it is meant a polypeptide that binds a guide RNA and is targeted to a specific DNA sequence by the guide RNA. A site-directed modifying polypeptide can be class 2 CRISPR/Cas protein (e.g., a type II CRISPR/Cas protein, a type V CRISPR/Cas protein, a type VI CRISPR/Cas protein). An example of a type II CRISPR/Cas protein is a Cas9 protein ("Cas9 polypeptide"). Examples of type V CRISPR/Cas proteins are Cpf1, C2c1, and C2c3. An example of a type II CRISPR/Cas protein is a C2c2 protein. Class 2 CRISPR/Cas proteins (e.g., Cas9, Cpf1, C2c1, C2c2, and C2c3) as described herein are targeted to a specific DNA sequence by the RNA (a guide RNA) to which it is bound. The guide RNA comprises a sequence that is complementary to a target sequence within the target DNA, thus targeting the bound CRISPR/Cas protein to a specific location within the target DNA (the target sequence). For example, a Cpf1 polypeptide as described herein is targeted to a specific DNA sequence by the RNA (a guide RNA) to which it is bound. The guide RNA comprises a sequence that is complementary to a target sequence within the target DNA, thus targeting the bound Cpf1 protein to a specific location within the target DNA (the target sequence).

"Heterologous," as used herein, means a nucleotide or polypeptide sequence that is not found in the native nucleic acid or protein, respectively. For example, a fusion Cas9 polypeptide of the present disclosure comprises: a) a Cas9 polypeptide; and b) a heterologous polypeptide comprising an amino acid sequence from a protein other than Cas9 polypeptide.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or noncoding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such can be done to replace a codon with a redundant codon encoding the same or a conservative amino acid, while typically introducing or removing a sequence recognition site. It can also be performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a polypeptide that facilitates uptake of a ribonucleoprotein into a eukaryotic cell" includes a plurality of such polypeptides and reference to "the target nucleic acid" includes reference to one or more target nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides modified site-directed modifying polypeptides, and ribonucleoproteins comprising the modified polypeptides. The modified site-directed modifying polypeptides are modified for passive entry into target cells. The modified site-directed modifying polypeptides, and ribonucleoproteins comprising same, are useful in a variety of methods for target nucleic acid modification, which methods are also provided.

Ribonucleoproteins

The present disclosure provides modified site-directed modifying polypeptides, and ribonucleoproteins (RNP) comprising the modified polypeptides. The terms "RNP" and "RNP complex" are used herein interchangeably. The modification of the site-directed modifying polypeptides provides for passive entry into a target eukaryotic cell, i.e., an RNP that comprises a modified site-directed modifying polypeptide of the present disclosure crosses the plasma membrane of a eukaryotic cell without the need for any additional agent (e.g., small molecule agents, lipids, etc.) to facilitate crossing the plasma membrane.

Site-Directed Modifying Polypeptide

The present disclosure provides site-directed modifying polypeptides, and RNPs comprising the site-directed modifying polypeptides. A site-directed modifying polypeptide of the present disclosure is a fusion polypeptide that comprises: a) a class 2 CRISPR/Cas protein; and b) a fusion partner, where the fusion partner is a heterologous polypeptide that facilitates uptake of the RNP into a eukaryotic cell, i.e., the heterologous polypeptide facilitates crossing the plasma membrane of a eukaryotic cell such that the RNP crosses the plasma membrane and enters the cytoplasm of the eukaryotic cell. A site-directed modifying polypeptide of the present disclosure is also referred to herein as a "fusion site-directed modifying polypeptide."

A fusion site-directed modifying polypeptide (e.g., a fusion class 2 CRISPR/Cas polypeptide) of the present disclosure comprises a fusion partner that is a heterologous polypeptide that facilitates uptake of an RNP into a eukaryotic cell. Thus, where an RNP comprises a fusion site-directed modifying polypeptide (e.g., a fusion class 2 CRISPR/Cas polypeptide) of the present disclosure, the RNP crosses the plasma membrane without the need for any mechanical, electrical, or chemical means to facilitate crossing of the plasma membrane by the RNP, and entry of the RNP into the cytoplasm. For example, where an RNP comprises a fusion site-directed modifying polypeptide (e.g., a fusion class 2 CRISPR/Cas polypeptide) of the present disclosure, the RNP crosses the plasma membrane without the need for any other agent that facilitates a macromolecule to cross the plasma membrane, e.g., without the use of a transfection reagent(s), viral infection, conjugation, protoplast fusion, an agent that modifies electrical conductivity of the plasma membrane, or an agent that modifies membrane stability. For example, where an RNP comprises a fusion site-directed modifying polypeptide (e.g., a fusion class 2 CRISPR/Cas polypeptide) of the present disclosure, the RNP crosses the plasma membrane without the need for any other agent that facilitates a macromolecule to cross the plasma membrane, e.g., without use of a cationic liposome (e.g., lipofectamine); without the use of diethylaminoethyl (DEAE)-dextran; without the use of calcium phosphate; without the use of a dendrimer; etc. As another example, where an RNP comprises a fusion site-directed modifying polypeptide (e.g., a fusion class 2 CRISPR/Cas polypeptide) of the present disclosure, the RNP crosses the plasma membrane without the need for modulation of the electrical conductivity of the plasma membrane, e.g., without the need for electroporation. As another example, where an RNP comprises a fusion site-directed modifying polypeptide (e.g., a fusion class 2 CRISPR/Cas polypeptide) of the present disclosure, the RNP crosses the plasma membrane without the need for mechanical means of facilitating crossing the plasma membrane, e.g., without the use of microinjection, pressure, or particle bombardment.

As noted above, a fusion site-directed modifying polypeptide (e.g., a fusion class 2 CRISPR/Cas polypeptide) of the present disclosure comprises a fusion partner that is a heterologous polypeptide that facilitates uptake of an RNP into a eukaryotic cell. In some cases, a fusion site-directed modifying polypeptide (e.g., a fusion class 2 CRISPR/Cas polypeptide) of the present disclosure comprises two or more heterologous polypeptides that facilitate uptake of an RNP into a eukaryotic cell. In some cases, a fusion site-directed modifying polypeptide (e.g., a fusion class 2 CRISPR/Cas polypeptide) of the present disclosure comprises two heterologous polypeptides that facilitate uptake of an RNP into a eukaryotic cell. In some cases, a fusion site-directed modifying polypeptide (e.g., a fusion class 2 CRISPR/Cas polypeptide) of the present disclosure comprises three heterologous polypeptides that facilitate uptake of an RNP into a eukaryotic cell. In some cases, a fusion site-directed modifying polypeptide (e.g., a fusion class 2 CRISPR/Cas polypeptide) of the present disclosure comprises four heterologous polypeptides that facilitate uptake of an RNP into a eukaryotic cell. In some cases, a fusion site-directed modifying polypeptide (e.g., a fusion class 2 CRISPR/Cas polypeptide) of the present disclosure comprises five heterologous polypeptides that facilitate uptake of an RNP into a eukaryotic cell. In some cases, a fusion site-directed modifying polypeptide (e.g., a fusion class 2 CRISPR/Cas polypeptide) of the present disclosure comprises six heterologous polypeptides that facilitate uptake of an RNP into a eukaryotic cell.

In some cases, a fusion site-directed modifying polypeptide (e.g., a fusion class 2 CRISPR/Cas polypeptide) of the present disclosure comprises two or more heterologous polypeptides that facilitate uptake of an RNP into a eukaryotic cell. In some cases, the two or more heterologous polypeptides are separated by a linker of from 2 amino acids to 25 amino acids (e.g., 2 amino acids (aa), 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa). Suitable linkers are described below.

A heterologous polypeptide that facilitates uptake of an RNP into a eukaryotic cell and that is suitable for inclusion in a fusion polypeptide of the present disclosure can have a length of from about 5 amino acids to about 70 amino acids, e.g., from 5 amino acids (aa) to 10 aa, from 10 aa to 15 aa, from 15 aa to 20 aa, from 20 aa to 25 aa, from 25 aa to 30 aa, from 30 aa to 35 aa, from 35 aa to 40 aa, from 40 aa to 45 aa, from 45 aa to 50 aa, from 50 aa to 55 aa, from 55 aa to 60 aa, from 60 aa to 65 aa, or from 65 aa to 70 aa. In some cases, a heterologous polypeptide that facilitates uptake of an RNP into a eukaryotic cell has a length of from 5 amino acids to 10 amino acids (e.g., 5, 6, 7, 8, 9, or 10 amino acids). In some cases, a heterologous polypeptide that facilitates uptake of an RNP into a eukaryotic cell has a length of 7 amino acids. In some cases, a heterologous polypeptide that facilitates uptake of an RNP into a eukaryotic cell has a length of from 10 amino acids to 15 amino acids (e.g., 10, 11, 12, 13, 14, or 15 amino acids). In some cases, a heterologous polypeptide that facilitates uptake of an RNP into a eukaryotic cell has a length of from 15 amino acids to 20 amino acids (e.g., 15, 16, 17, 18, 19, or 20 amino acids). In some cases, a heterologous polypeptide that facilitates uptake of an RNP into a eukaryotic cell has a length of from 20 amino acids to 25 amino acids (e.g., 20, 21, 22, 23, 24, or 25 amino acids).

A heterologous polypeptide that facilitates uptake of an RNP into a eukaryotic cell and that is suitable for inclusion in a fusion polypeptide of the present disclosure can have a high percentage of arginine and/or lysine residues. For example, a suitable heterologous polypeptide that facilitates uptake of an RNP into a eukaryotic cell can have an amino acid sequence comprising from 20% to 80% arginine and/or lysine residues. As an example, a suitable heterologous polypeptide that facilitates uptake of an RNP into a eukaryotic cell can have an amino acid sequence comprising from 20% to 80% lysine residues. As an example, a suitable heterologous polypeptide that facilitates uptake of an RNP into a eukaryotic cell can have an amino acid sequence comprising from 20% to 80% arginine+lysine residues.

In some cases, a heterologous polypeptide that facilitates uptake of an RNP into a eukaryotic cell and that is suitable for inclusion in a fusion polypeptide of the present disclosure comprises the amino acid sequence K-K/R-X-K/R, where X is any amino acid. In some cases, a heterologous polypeptide that facilitates uptake of an RNP into a eukaryotic cell and that is suitable for inclusion in a fusion polypeptide of the present disclosure comprises the amino acid sequence K-K/R-X-K/R, where X is any amino acid; and has a length of from 7 to 17 amino acids. In some cases, a heterologous polypeptide that facilitates uptake of an RNP into a eukaryotic cell and that is suitable for inclusion in a fusion polypeptide of the present disclosure comprises the amino acid sequence K-K/R-X-K/R, where X is any amino acid; and has a length of from 5 to 15 amino acids. In some cases, a heterologous polypeptide that facilitates uptake of an RNP into a eukaryotic cell and that is suitable for inclusion in a fusion polypeptide of the present disclosure comprises the amino acid sequence K-K/R-X-K/R, where X is any amino acid; and has a length of from 15 to 20 amino acids.

Non-limiting examples of suitable heterologous polypeptides that facilitate uptake of an RNP into a eukaryotic cell are presented in FIG. 1A-1G. In some cases, a heterologous polypeptide that facilitates uptake of an RNP into a eukaryotic cell and that is suitable for inclusion in a fusion polypeptide of the present disclosure comprises the amino acid sequence PKKKRKV (SEQ ID NO: 1090). In some cases, a heterologous polypeptide that facilitates uptake of an RNP into a eukaryotic cell and that is suitable for inclusion in a fusion polypeptide of the present disclosure comprises the amino acid sequence PKKKRKV (SEQ ID NO: 1090), and has a length of 7 amino acids. In some cases, a heterologous polypeptide that facilitates uptake of an RNP into a eukaryotic cell and that is suitable for inclusion in a fusion polypeptide of the present disclosure comprises the amino acid sequence RPAATKKAGQAKKKKLD (SEQ ID NO: 1096). In some cases, a heterologous polypeptide that facilitates uptake of an RNP into a eukaryotic cell and that is suitable for inclusion in a fusion polypeptide of the present disclosure comprises the amino acid sequence RPAATKK-AGQAKKKKLD (SEQ ID NO: 1096), and has a length of 17 amino acids. In some cases, a heterologous polypeptide that facilitates uptake of an RNP into a eukaryotic cell and that is suitable for inclusion in a fusion polypeptide of the present disclosure comprises the amino acid sequence AVKRPAATKKAGQAKKKKLD (SEQ ID NO: 1097). In some cases, a heterologous polypeptide that facilitates uptake of an RNP into a eukaryotic cell and that is suitable for inclusion in a fusion polypeptide of the present disclosure comprises the amino acid sequence AVKRPAATKK-AGQAKKKKLD (SEQ ID NO: 1097), and has a length of 20 amino acids. In some cases, a heterologous polypeptide that facilitates uptake of an RNP into a eukaryotic cell and that is suitable for inclusion in a fusion polypeptide of the present disclosure comprises the amino acid sequence AVKRPAATKKAGQAKKK (SEQ ID NO: 1098). In some cases, a heterologous polypeptide that facilitates uptake of an RNP into a eukaryotic cell and that is suitable for inclusion in a fusion polypeptide of the present disclosure comprises the amino acid sequence AVKRPAATKK-AGQAKKK (SEQ ID NO: 1098), and has a length of 17 amino acids. In some cases, a heterologous polypeptide that facilitates uptake of an RNP into a eukaryotic cell and that is suitable for inclusion in a fusion polypeptide of the present disclosure comprises the amino acid sequence KRPAATK-KAGQAKKKKLD (SEQ ID NO: 1099), and has a length of 18 amino acids. In some cases, a heterologous polypeptide that facilitates uptake of an RNP into a eukaryotic cell and that is suitable for inclusion in a fusion polypeptide of the present disclosure comprises the amino acid sequence PKKKRKVED (SEQ ID NO: 1248); and has a length of 9 amino acids. In some cases, a heterologous polypeptide that facilitates uptake of an RNP into a eukaryotic cell and that is suitable for inclusion in a fusion polypeptide of the present disclosure comprises the amino acid sequence PKKKRKVDT (SEQ ID NO: 1249); and has a length of 9 amino acids.

In some cases, a heterologous polypeptide that facilitates uptake of an RNP into a eukaryotic cell and that is suitable for inclusion in a fusion polypeptide of the present disclosure is at or near the N-terminus of a class 2 CRISPR/Cas polypeptide (e.g., a type II, type V, or type VI CRISPR/Cas site-directed modifying polypeptide). In some cases, a heterologous polypeptide that facilitates uptake of an RNP into a eukaryotic cell and that is suitable for inclusion in a fusion polypeptide of the present disclosure is at or near the C-terminus of a class 2 CRISPR/Cas polypeptide (e.g., a type II, type V, or type VI CRISPR/Cas site-directed modifying polypeptide). In some cases, a heterologous polypeptide that facilitates uptake of an RNP into a eukaryotic cell and that is suitable for inclusion in a fusion polypeptide of the present disclosure is located internally within a class 2 CRISPR/Cas polypeptide (e.g., a type II, type V, or type VI CRISPR/Cas site-directed modifying polypeptide).

In some cases, where a fusion site-directed modifying polypeptide (e.g., a fusion class 2 CRISPR/Cas polypeptide) of the present disclosure comprises two or more heterologous polypeptides that facilitate uptake of an RNP into a eukaryotic cell, the two or more heterologous polypeptides are at or near the N-terminus of a class 2 CRISPR/Cas polypeptide. In some cases, where a fusion site-directed modifying polypeptide (e.g., a fusion class 2 CRISPR/Cas polypeptide) of the present disclosure comprises two or more heterologous polypeptides that facilitate uptake of an RNP into a eukaryotic cell, the two or more heterologous polypeptides are at or near the C-terminus of a class 2 CRISPR/Cas polypeptide. In some cases, where a fusion site-directed modifying polypeptide (e.g., a fusion class 2 CRISPR/Cas polypeptide) of the present disclosure comprises two or more heterologous polypeptides that facilitate uptake of an RNP into a eukaryotic cell, the two or more heterologous polypeptides are at or near the N-terminus and at or near the C-terminus of a class 2 CRISPR/Cas polypeptide. In some cases, where a fusion site-directed modifying polypeptide (e.g., a fusion class 2 CRISPR/Cas polypeptide) of the present disclosure comprises two or more heterologous polypeptides that facilitate uptake of an RNP into a eukaryotic cell, the two or more heterologous polypeptides are at or near the N-terminus and located internally within a class 2 CRISPR/Cas polypeptide. In some cases, where a fusion site-directed modifying polypeptide (e.g., a fusion class 2 CRISPR/Cas polypeptide) of the present disclosure comprises two or more heterologous polypeptides that facilitate uptake of an RNP into a eukaryotic cell, the two or more heterologous polypeptides are at or near the C-terminus and located internally within a class 2 CRISPR/Cas polypeptide.

In some cases, a fusion polypeptide of the present disclosure comprises, in order from N-terminus to C-terminus: a) a heterologous polypeptide that facilitates entry into a eukaryotic cell; and b) a class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) two or more heterologous polypeptides that facilitates entry into a eukaryotic cell; and b) a class 2 CRISPR/Cas polypeptide (e.g., a type II, type V, or type VI CRISPR/Cas site-directed modifying polypeptide).

In some cases, a fusion polypeptide of the present disclosure comprises, in order from N-terminus to C-terminus: a) a class 2 CRISPR/Cas polypeptide (e.g., a type II, type V, or type VI CRISPR/Cas site-directed modifying polypeptide); and b) a heterologous polypeptide that facilitates entry into a eukaryotic cell. In some cases, a fusion polypeptide of the present disclosure comprises, in order from N-terminus to C-terminus: a) a class 2 CRISPR/Cas polypeptide (e.g., a type II, type V, or type VI CRISPR/Cas site-directed modifying polypeptide); and b) two or more heterologous polypeptides that facilitates entry into a eukaryotic cell.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; and c) a class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a linker polypeptide of from about 3 amino acids to about 25 amino acids in length; c) a second heterologous polypeptide that facilitates entry into a eukaryotic cell; and d) a class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a first linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; and e) a Class 2 CRISPR/Cas polypeptide (e.g., a type II, type V, or type VI CRISPR/Cas site-directed modifying polypeptide).

In some cases, the first and the second heterologous polypeptides are identical. In other instances, the first and the second heterologous polypeptides are different, e.g., differ from one another in amino acid sequence by at least one amino acid.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a Class 2 CRISPR/Cas polypeptide (e.g., a type II, type V, or type VI CRISPR/Cas site-directed modifying polypeptide); and d) a third heterologous polypeptide that facilitates entry into a eukaryotic cell. In some cases, a fusion polypeptide of the present disclosure comprises, in order from N-terminus to C-terminus: a) a first heterologous polypeptide that facilitates entry into a eukaryotic cell; b) a linker polypeptide of from about 3 amino acids to about 25 amino acids in length; c) a second heterologous polypeptide that facilitates entry into a eukaryotic cell; d) a Class 2 CRISPR/Cas polypeptide (e.g., a type II, type V, or type VI CRISPR/Cas site-directed modifying polypeptide); and e) a third heterologous polypeptide that facilitates entry into a eukaryotic cell. In some cases, a fusion polypeptide of the present disclosure comprises, in order from N-terminus to C-terminus: a) a first heterologous polypeptide that facilitates entry into a eukaryotic cell; b) a first linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a Class 2 CRISPR/Cas polypeptide (e.g., a type II, type V, or type VI CRISPR/Cas site-directed modifying polypeptide); and f) a third heterologous polypeptide that facilitates entry into a eukaryotic cell. In some cases, the first, the second, and the third heterologous polypeptides are identical. In other instances, the first, the second, and the third second heterologous polypeptides are different, e.g., differ from one another in amino acid sequence by at least one amino acid. In some cases, the first and the second heterologous polypeptides are identical; and the third heterologous polypeptide differs from the first and the second heterologous polypeptides.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a third heterologous polypeptide that facilitates entry into a eukaryotic cell; and d) a Class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; and f) a Class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a first linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a third linker polypeptide of from about 3 amino acids to about 25 amino acids in length; and g) a Class 2 CRISPR/Cas polypeptide (e.g., a type II, type V, or type VI CRISPR/Cas site-directed modifying polypeptide). In some cases, the first, the second, and the third heterologous polypeptides are identical. In other instances, the first, the second, and the third second heterologous polypeptides are different, e.g., differ from one another in amino acid sequence by at least one amino acid.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a third heterologous polypeptide that facilitates entry into a eukaryotic cell; d) a Class 2 CRISPR/Cas polypeptide (e.g., a type II, type V, or type VI CRISPR/Cas site-directed modifying polypeptide); and e) a fourth heterologous polypeptide that facilitates entry into a eukaryotic cell. In some cases, a fusion polypeptide of the present disclosure comprises, in order from N-terminus to C-terminus: a) a first heterologous polypeptide that facilitates entry into a eukaryotic cell; b) a linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a Class 2 CRISPR/Cas polypeptide (e.g., a type II, type V, or type VI CRISPR/Cas site-directed modifying polypeptide); g) a fourth heterologous polypeptide that facilitates entry into a eukaryotic cell. In some cases, a fusion polypeptide of the present disclosure comprises, in order from N-terminus to C-terminus: a) a first heterologous polypeptide that facilitates entry into a eukaryotic cell; b) a first linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a third linker polypeptide of from about 3 amino acids to about 25 amino acids in length; g) a Class 2 CRISPR/Cas polypeptide (e.g., a type II, type V, or type VI CRISPR/Cas site-directed modifying polypeptide); and h) a fourth heterologous polypeptide that facilitates entry into a eukaryotic cell. In some cases, the first, the second, the third, the fourth heterologous polypeptides are identical. In other instances, the first, the second, the third, and the fourth heterologous polypeptides are different, e.g., differ from one another in amino acid sequence by at least one amino acid. In some cases, the first, the second, and the third heterologous polypeptides are identical; and the fourth heterologous polypeptide differs from the first, the second, and the third heterologous polypeptides.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a third heterologous polypeptide that facilitates entry into a eukaryotic cell; d) a fourth heterologous polypeptide that facilitates entry into a eukaryotic cell; and e) a Class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a third linker polypeptide of from about 3 amino acids to about 25 amino acids in length g) a fourth heterologous polypeptide that facilitates entry into a eukaryotic cell; and h) a Class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a first linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a third linker polypeptide of from about 3 amino acids to about 25 amino acids in length g) a fourth heterologous polypeptide that facilitates entry into a eukaryotic cell; h) a fourth linker polypeptide of from about 3 amino acids to about 25 amino acids in length; and i) a Class 2 CRISPR/Cas polypeptide (e.g., a type II, type V, or type VI CRISPR/Cas site-directed modifying polypeptide). In some cases, the first, second, third, and fourth heterologous polypeptides are identical. In other instances, the first, second, third, and fourth heterologous polypeptides are different, e.g., differ from one another in amino acid sequence by at least one amino acid.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a third heterologous polypeptide that facilitates entry into a eukaryotic cell; d) a fourth heterologous polypeptide that facilitates entry into a eukaryotic cell; e) a Class 2 CRISPR/Cas polypeptide (e.g., a type II, type V, or type VI CRISPR/Cas site-directed modifying polypeptide); and f) a fifth heterologous polypeptide that facilitates entry into a eukaryotic cell. In some cases, a fusion polypeptide of the present disclosure comprises, in order from N-terminus to C-terminus: a) a first heterologous polypeptide that facilitates entry into a eukaryotic cell; b) a linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a third linker polypeptide of from about 3 amino acids to about 25 amino acids in length; g) a fourth heterologous polypeptide that facilitates entry into a eukaryotic cell; h) a Class 2 CRISPR/Cas polypeptide (e.g., a type II, type V, or type VI CRISPR/Cas site-directed modifying polypeptide); and i) a fifth heterologous polypeptide that facilitates entry into a eukaryotic cell. In some cases, a fusion polypeptide of the present disclosure comprises, in order from N-terminus to C-terminus: a) a first heterologous polypeptide that facilitates entry into a eukaryotic cell; b) a first linker polypeptide of from about 3 amino acids to about 25 amino acids in length; c) a second heterologous polypeptide that facilitates entry into a eukaryotic cell; d) a second linker polypeptide of from about 3 amino acids to about 25 amino acids in length; e) a third heterologous polypeptide that facilitates entry into a eukaryotic cell; f) a third linker polypeptide of from about 3 amino acids to about 25 amino acids in length g) a fourth heterologous polypeptide that facilitates entry into a eukaryotic cell; h) a fourth linker polypeptide of from about 3 amino acids to about 25 amino acids in length; i) a Class 2 CRISPR/Cas polypeptide (e.g., a type II, type V, or type VI CRISPR/Cas site-directed modifying polypeptide); j) a fifth heterologous polypeptide that facilitates entry into a eukaryotic cell. In some cases, the first, second, third, and fourth heterologous polypeptides are identical. In other instances, the first, second, third, and fourth heterologous polypeptides are different, e.g., differ from one another in amino acid sequence by at least one amino acid. In some cases, the first, second, third, fourth, and fifth heterologous polypeptides are identical. In some cases, the first, second, third, fourth, and fifth heterologous polypeptides are different, e.g., differ from one another in amino acid sequence by at least one amino acid. In some cases, the first, second, third, and fourth heterologous polypeptides are identical; and the fifth heterologous differs from the first, second, third, and fourth heterologous polypeptides.

In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a third heterologous polypeptide that facilitates entry into a eukaryotic cell; d) a fourth heterologous polypeptide that facilitates entry into a eukaryotic cell; e) a fifth heterologous polypeptide that facilitates entry into a eukaryotic cell; and f) a Class 2 CRISPR/Cas polypeptide (e.g., a type II, type V, or type VI CRISPR/Cas site-directed modifying polypeptide). In some cases, a fusion polypeptide of the present disclosure comprises, in order from N-terminus to C-terminus: a) a first heterologous polypeptide that facilitates entry into a eukaryotic cell; b) a second heterologous polypeptide that facilitates entry into a eukaryotic cell; c) a third heterologous polypeptide that facilitates entry into a eukaryotic cell; d) a fourth heterologous polypeptide that facilitates entry into a eukaryotic cell; e) a fifth heterologous polypeptide that facilitates entry into a eukaryotic cell; f) a sixth heterologous polypeptide that facilitates entry into a eukaryotic cell; and g) a Class 2 CRISPR/Cas polypeptide (e.g., a type II, type V, or type VI CRISPR/Cas site-directed modifying polypeptide). In any of these embodiments, a linker can be interposed between any two heterologous polypeptides and/or between a heterologous polypeptide and a Class 2 CRISPR/Cas polypeptide (e.g., a type II, type V, or type VI CRISPR/Cas site-directed modifying polypeptide).

Linkers

In some embodiments, a fusion site-directed modifying polypeptide (e.g., a fusion class 2 CRISPR/Cas polypeptide) of the present disclosure includes one or more internally inserted linker polypeptides, where a linker polypeptide can be between two heterologous polypeptides that facilitate crossing a eukaryotic plasma membrane; between a heterologous polypeptide that facilitate crossing a eukaryotic plasma membrane and a site-directed modifying polypeptide; and the like. The linker polypeptide may have any of a variety of amino acid sequences. Proteins can be joined by a spacer peptide, generally of a flexible nature, although other chemical linkages are not excluded. Suitable linkers include polypeptides of from 3 amino acids to 40 amino acids in length, e.g., from 3 amino acids to 25 amino acids in length, from 3 amino acids to 10 amino acids in length, from 3 amino acids to 5 amino acids in length, etc. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Exemplary linker polypeptides include glycine polymers $(G)_n$, glycine-serine polymers (including, for example, GGS, $(GS)_n$, $GSGGS_n$ (SEQ ID NO: 517), $GGSGGS_n$ (SEQ ID NO: 518), and $GGGS_n$ (SEQ ID NO: 519), where n is an integer of at least one, and can range from 1 to about 10), glycine-alanine polymers, alanine-serine polymers. Exemplary linkers can comprise amino acid sequences including, but not limited to, GS, GGS, GGSG (SEQ ID NO: 520), GGSGG (SEQ ID NO: 521), GSGSG (SEQ ID NO: 522), GSGGG (SEQ ID NO: 523), GGGSG (SEQ ID NO: 524), GSSSG (SEQ ID NO: 525), and the like. The ordinarily skilled artisan will recognize that design of a peptide conjugated to any elements described above can include linkers that are all or partially flexible, such that the linker can include a flexible linker as well as one or more portions that confer less flexible structure.

Class 2 CRISPR/Cas Site-Directed Modifying Polypeptides

In some cases, a fusion site-directed modifying polypeptide (e.g., a fusion class 2 CRISPR/Cas polypeptide) of the present disclosure is a fusion class 2 CRISPR/Cas site-directed modifying polypeptide and therefore comprises a class 2 CRISPR/Cas polypeptide. In class 2 CRISPR systems, the functions of the effector complex (e.g., cleaving target DNA) are carried out by a single protein (e.g., see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97). As such, the term class 2 CRISPR/Cas protein is used herein to encompass the effector protein (the target nucleic acid cleaving protein) from class 2 CRISPR systems. Thus, the term "class 2 CRISPR/Cas protein" as used herein encompasses type II CRISPR/Cas proteins (e.g., Cas9), type V CRISPR/Cas proteins (e.g., Cpf1, C2c1, C2C3), and type VI CRISPR/Cas proteins (e.g., C2c2). To date, class 2 CRISPR/Cas proteins encompass type II, type V, and type VI CRISPR/Cas proteins, but the term is also meant to encompass any class 2 CRISPR/Cas protein suitable for forming a subject RNP complex.

Type II CRISPR/Cas Site-Directed Modifying Polypeptides

As noted above, in some cases, a fusion site-directed modifying polypeptide of the present disclosure comprises a type II CRISPR site-directed modifying polypeptide (e.g., a "Cas9 polypeptide").

In some cases, a fusion site-directed modifying polypeptide of the present disclosure comprises: a) Cas9 protein; and b) a heterologous polypeptide that facilitates entry of an RNP (where the RNP comprises the fusion site-directed modifying polypeptide and a guide RNA) into a eukaryotic cell. In some cases, a fusion site-directed modifying polypeptide of the present disclosure comprises: a) chimeric Cas9 protein; and b) a heterologous polypeptide that facilitates entry of an RNP (where the RNP comprises the fusion site-directed modifying polypeptide and a guide RNA) into a eukaryotic cell. In some cases, a fusion site-directed modifying polypeptide of the present disclosure comprises: a) variant Cas9 protein that is a nickase; and b) a heterologous polypeptide that facilitates entry of an RNP (where the RNP comprises the fusion site-directed modifying polypeptide and a guide RNA) into a eukaryotic cell. In some cases, a fusion site-directed modifying polypeptide of the present disclosure comprises: a) variant Cas9 protein that exhibits reduced enzymatic activity (e.g., a "dead Cas9" or "dCas9"); and b) a heterologous polypeptide that facilitates entry of an RNP (where the RNP comprises the fusion site-directed modifying polypeptide and a guide RNA) into a eukaryotic cell.

Cas9 Polypeptides

A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein, where the heterologous protein provides an activity not provided by the Cas9 protein, where the activity is other than facilitating entry of an RNP into a eukaryotic cell. The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to Streptococcus pyogenes Cas9).

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a chimeric Cas9 protein includes a heterologous polypeptide that has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a chimeric Cas9 protein includes a heterologous polypeptide that has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 presents motifs that can be used to help determine whether a given protein is a Cas9 protein.

TABLE 1

Table 1 lists 4 motifs that are present in Cas9 sequences from various species. The amino acids listed in Table 1 are from the Cas9 from S. pyogenes (SEQ ID NO: 5)

| Motif # | Motif | Amino acids (residue #s) | Highly conserved |
|---|---|---|---|
| 1 | RuvC-like I | IGLDIGTNSVGWAVI (7-21) (SEQ ID NO: 1) | D10, G12, G17 |

TABLE 1-continued

Table 1 lists 4 motifs that are present in Cas9 sequences from various species. The amino acids listed in Table 1 are from the Cas9 from *S. pyogenes* (SEQ ID NO: 5)

| Motif # | Motif | Amino acids (residue #s) | Highly conserved |
|---|---|---|---|
| 2 | RuvC-like II | IVIEMARE (759-766) (SEQ ID NO: 2) | E762 |
| 3 | HNH-motif | DVDHIVPQSFLKDDSIDNKVLTRSDKN (837-863)(SEQ ID NO: 3) | H840, N854, N863 |
| 4 | RuvC-like II | HHAHDAYL (982-989) (SEQ ID NO: 4) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:1-4), or to the corresponding portions in any of the amino acid sequences set forth as SEQ ID NOs: 6-816.

As used herein, the term "Cas9 protein" encompasses a "chimeric Cas9 protein." As used herein, the term "Cas9 protein" encompasses a variant Cas9 that is a nickase. As used herein, the term "Cas9 protein" encompasses a variant Cas9 that exhibits reduced enzymatic activity (e.g., a "dead Cas9" or "dCas9").

Variant Cas9 Proteins—Nickases and dCas9

In some cases, a fusion site-directed modifying polypeptide of the present disclosure comprises: a) a variant Cas9 protein; and b) a heterologous polypeptide that facilitates entry of an RNP (where the RNP comprises the fusion site-directed modifying polypeptide and a guide RNA) into a eukaryotic cell. A variant Cas9 protein has an amino acid sequence that is different by one amino acid (e.g., has a deletion, insertion, substitution, fusion) (i.e., different by at least one amino acid) when compared to the amino acid sequence of a wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as "dCas9." A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In some cases, a variant Cas9 protein has a reduced ability to cleave both the complementary and the non-complementary strands of a double stranded target nucleic acid. As a non-limiting example, in some cases, the variant Cas9 protein harbors mutations at amino acid positions corresponding to residues D10 and H840 (e.g., D10A and H840A) of SEQ ID NO: 5 (or the corresponding residues of any of the proteins set forth as SEQ ID NOs: 6-261 and 264-816) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "dead" Cas9 or simply "dCas9." See, e.g., SEQ ID NO: 264.

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 5 (or the corresponding mutations of any of the proteins set forth as SEQ ID NOs: 6-816) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 5 or the corresponding mutations of any of the proteins set forth as SEQ ID NOs: 6-816, e.g., D10A, G12A, G17A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816.

Type V and Type VI CRISPR Site-Directed Modifying Polypeptides

In some cases, a fusion site-directed modifying polypeptide of the present disclosure comprises a type V CRISPR/Cas protein (polypeptide) (e.g., Cpf1, C2c1, C2c3). In some cases, a fusion site-directed modifying polypeptide of the present disclosure comprises a type VI CRISPR/Cas protein (polypeptide) (e.g., C2c2). In some cases, a fusion site-directed modifying polypeptide of the present disclosure comprises a type V or type VI CRISPR/Cas protein (polypeptide) (e.g., Cpf1, C2c1, C2c2, C2c3). Thus, in some cases, a fusion site-directed modifying polypeptide (e.g., a fusion class 2 CRISPR/Cas polypeptide) of the present disclosure comprises: a) a Type V or type VI CRISPR/Cas polypeptide (e.g., Cpf1, C2c1, C2c2, C2c3); and b) a heterologous polypeptide that facilitates entry of an RNP (where the RNP comprises the fusion site-directed modifying polypeptide and a guide RNA) into a eukaryotic cell. In some cases, a Type V CRISPR/Cas polypeptide is a Cpf1 protein.

Examples and guidance related to type V and type VI CRISPR/Cas proteins (e.g., cpf1, C2c1, C2c2, and C2c3 guide RNAs) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

In some cases, the a Type V or type VI CRISPR/Cas polypeptide (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the a Type V or type VI CRISPR/Cas polypeptide (e.g., Cpf1, C2c1, C2c2, C2c3) exhibits reduced enzymatic activity relative to a corresponding wild-type a Type V or type VI CRISPR/Cas polypeptide (e.g., Cpf1, C2c1, C2c2, C2c3), and retains DNA binding activity.

In some cases a type V CRISPR/Cas protein is Cpf1. In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 8 (SEQ ID NOs: 1252-1256). In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence depicted in FIG. 8 (SEQ ID NOs: 1252-1256).

In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a Cpf1 polypeptide of the amino acid sequence depicted in FIG. 8 (SEQ ID NOs: 1252-1256). In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a Cpf1 polypeptide of the amino acid sequence depicted in FIG. 8 (SEQ ID NOs: 1252-1256). In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a Cpf1 polypeptide of the amino acid sequence depicted in FIG. 8 (SEQ ID NOs: 1252-1256).

In some cases, the Cpf1 polypeptide exhibits reduced enzymatic activity relative to a wild-type Cpf1 polypeptide (e.g., relative to a Cpf1 polypeptide comprising the amino acid sequence depicted in FIG. 8 (SEQ ID NOS: 1252-1256), and retains DNA binding activity. In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 8 (SEQ ID NOS: 1252-1256); and comprises an amino acid substitution (e.g., a D→A substitution) at an amino acid residue corresponding to amino acid 917 of the amino acid sequence depicted in FIG. 8 (SEQ ID NOS: 1252-1256). In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 8 (SEQ ID NOS: 1252-1256); and comprises an amino acid substitution (e.g., an E→A substitution) at an amino acid residue corresponding to amino acid 1006 of the amino acid sequence depicted in FIG. 8 (SEQ ID NOS: 1252-1256). In some cases, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 8 (SEQ ID NOS: 1252-1256); and comprises an amino acid substitution (e.g., a D-A substitution) at an amino acid residue corresponding to amino acid 1255 of the amino acid sequence depicted in FIG. 8 (SEQ ID NOS: 1252-1256).

In some cases, a suitable Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to an amino acid sequence depicted in FIG. 8 (SEQ ID NOs: 1252-1256).

In some cases a type V CRISPR/Cas protein is C2c1 (examples include those depicted in FIG. 8 as SEQ ID NOs: 1280-1287). In some cases, a C2c1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence set forth in SEQ ID NOs: 1280-1287). In some cases, a C2c1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence set forth in SEQ ID NOs: 1280-1287).

In some cases, a C2c1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a C2c1 polypeptide of the amino acid sequence set forth in SEQ ID NOs: 1280-1287). In some cases, a C2c1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a C2c1 polypeptide of the amino acid sequence set forth in SEQ ID NOs: 1280-1287). In some cases, a C2c1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a C2c1 polypeptide of the amino acid sequence set forth in SEQ ID NOs: 1280-1287).

In some cases, the C2c1 polypeptide exhibits reduced enzymatic activity relative to a wild-type C2c1 polypeptide (e.g., relative to a C2c1 polypeptide comprising the amino acid sequence set forth in SEQ ID NOs: 1280-1287), and retains DNA binding activity. In some cases, a suitable C2c1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to an amino acid sequence depicted in FIG. 8 (SEQ ID NOs: 1280-1287).

In some cases a type V CRISPR/Cas protein is C2c3 (examples include those depicted in FIG. 8 as SEQ ID NOs: 1290-1293). In some cases, a C2c3 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence set forth in SEQ ID NOs: 1290-1293). In some cases, a C2c3 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence set forth in SEQ ID NOs: 1290-1293).

In some cases, a C2c3 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a C2c3 polypeptide of the amino acid sequence set forth in SEQ ID NOs: 1290-1293). In some cases, a C2c3 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a C2c3 polypeptide of the amino acid sequence set forth in SEQ ID NOs: 1290-1293). In some cases, a C2c3 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a C2c3 polypeptide of the amino acid sequence set forth in SEQ ID NOs: 1290-1293).

In some cases, the C2c3 polypeptide exhibits reduced enzymatic activity relative to a wild-type C2c3 polypeptide (e.g., relative to a C2c3 polypeptide comprising the amino acid sequence set forth in SEQ ID NOs: 1290-1293), and retains DNA binding activity. In some cases, a suitable C2c3 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to an amino acid sequence depicted in FIG. 8 (SEQ ID NOs: 1290-1293).

In some cases a type VI CRISPR/Cas protein is C2c2 (examples include those depicted in FIG. 8 as SEQ ID NOs: 1300-1311). In some cases, a C2c2 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence set forth in SEQ ID NOs: 1300-1311). In some cases, a C2c2 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence set forth in SEQ ID NOs: 1300-1311).

In some cases, a C2c2 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a C2c2 polypeptide of the amino acid sequence set forth in SEQ ID NOs: 1300-1311). In some cases, a C2c2 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a C2c2 polypeptide of the amino acid sequence set forth in SEQ ID NOs: 1300-1311). In some cases, a C2c2 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a C2c2 polypeptide of the amino acid sequence set forth in SEQ ID NOs: 1300-1311).

In some cases, the C2c2 polypeptide exhibits reduced enzymatic activity relative to a wild-type C2c2 polypeptide (e.g., relative to a C2c2 polypeptide comprising the amino acid sequence set forth in SEQ ID NOs: 1300-1311), and retains DNA binding activity. In some cases, a suitable C2c2 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to an amino acid sequence depicted in FIG. 8 (SEQ ID NOs: 1300-1311).

Guide RNA

A nucleic acid molecule that binds to a class 2 CRISPR/Cas protein (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA."

A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

A guide RNA can be referred to by the protein to which it corresponds. For example, when the class 2 CRISPR/Cas protein is a Cas9 protein (e.g., a fusion Cas9 polypeptide), the corresponding guide RNA can be referred to as a "Cas9 guide RNA." Likewise, as another example, when the class 2 CRISPR/Cas protein is a Cpf1 protein (e.g., a Cpf1 fusion polypeptide), the corresponding guide RNA can be referred to as a "Cpf1 guide RNA."

In some embodiments, a guide RNA includes two separate nucleic acid molecules: an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Cas9 Guide RNA

A nucleic acid molecule that binds to a CRISPR/Cas9 protein and targets the complex to a specific location within a target nucleic acid is referred to herein as a "Cas9 guide RNA."

A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein, e.g., a fusion Cas9 polypeptide, form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein, e.g., a fusion Cas9 polypeptide, to any desired sequence of any desired target nucleic acid, with the exception (e.g., as described herein) that the PAM sequence can be taken into account. Thus, for example, a Cas9 guide RNA can have a targeting segment with a sequence that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075, or complements thereof. For example, in some cases, sequences from SEQ ID NOs: 827-957 (which are from tracrRNAs) or complements thereof, can pair with sequences from SEQ ID NOs: 964-1075 (which are from crRNAs), or complements thereof, to form a dsRNA duplex of a protein binding segment.

Targeting Segment of a Cas9 Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 guide RNAs can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10): 1163-71; Cho et al., Genetics. 2013 November; 195(3): 1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2): 333-9; and U.S. patents and patent applications: U.S. Pat. Nos. 8,906,616; 8,895,308; 8,889,418; 8,889,356; 8,871, 445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Guide RNAs Corresponding to Type V and Type VI CRISPR/Cas Proteins

Cpf1 Guide RNA

A nucleic acid molecule that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

A type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt,).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex).

The target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

The guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

The guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotide and 23 complementary nucleotides with the target nucleic acid sequence.

The duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an example, a duplex-forming segment of a Cpf1 guide RNA can comprise a nucleotide sequence selected from (5' to 3'): AAUUUCUACUGUUGUAGAU (SEQ ID NO: 1257), AAUUUCUGCUGUUGCAGAU (SEQ ID NO: 1258), AAUUUCCACUGUUGUGGAU (SEQ ID NO: 1259), AAUUCCUACUGUUGUAGGU (SEQ ID NO: 1260), AAUUUCUACUAUUGUAGAU (SEQ ID NO: 1261), AAUUUCUACUGCUGUAGAU (SEQ ID NO: 1262), AAUUUCUACUUUGUAGAU (SEQ ID NO: 1263), and AAUUUCUACUUGUAGAU (SEQ ID NO: 1264). The guide sequence can then follow (5' to 3') the duplex forming segment.

A non-limiting example of an activator RNA (e.g. tracrRNA) of a C2c1 guide RNA (dual guide or single guide) is an RNA that includes the nucleotide sequence GAAUUUUUCAACGGGUGUGCCAAUGGCCAC-UUUCCAGGUGGCAAAGCCCG UUGAGCUUCU-CAAAAAG (SEQ ID NO: 1265). In some cases, a C2c1 guide RNA (dual guide or single guide) is an RNA that includes the nucleotide sequence In some cases, a C2c1 guide RNA (dual guide or single guide) is an RNA that includes the nucleotide sequence GUCUA-GAGGACAGAAUUUUCAACGGGUGUGC-CAAUGGCCACUUUCCAGG UGGCAAAGCCCGUUGAGCUUCUCAAAAAG (SEQ ID NO: 1266). In some cases, a C2c1 guide RNA (dual guide or single guide) is an RNA that includes the nucleotide sequence UCUAGAGGACAGAAUUUUUCAACGGGU-GUGCCAAUGGCCACUUUCCAGGU GGCAAAGCCCGUUGAGCUUCUCAAAAAG (SEQ ID NO: 1267). A non-limiting example of an activator RNA (e.g. tracrRNA) of a C2c1 guide RNA (dual guide or single guide) is an RNA that includes the nucleotide sequence ACUUUCCAGGCAAAGCCCGUUGAGCUUCU-CAAAAAG (SEQ ID NO: 1268). In some cases, a duplex forming segment of a C2c1 guide RNA (dual guide or single guide) of an activator RNA (e.g. tracrRNA) includes the nucleotide sequence AGCUUCUCA (SEQ ID NO: 1269) or the nucleotide sequence GCUUCUCA (SEQ ID NO: 1270) (the duplex forming segment from a naturally existing tracrRNA.

A non-limiting example of a targeter RNA (e.g. crRNA) of a C2c1 guide RNA (dual guide or single guide) is an RNA with the nucleotide sequence CUGA GAAGUGGCACNNNNNNNNNNNNNNNNNNNN (SEQ ID NO: 1271), where the Ns represent the guide sequence, which will vary depending on the target sequence, and although 20 Ns are depicted a range of different lengths are acceptable. In some cases, a duplex forming segment of a C2c1 guide RNA (dual guide or single guide) of a targeter RNA (e.g. crRNA) includes the nucleotide sequence CUGAGAAGUGGCAC (SEQ ID NO: 1272) or includes the nucleotide sequence CUGAGAAGU (SEQ ID NO: 1273) or includes the nucleotide sequence UGAGAAGUGGCAC (SEQ ID NO: 1274) or includes the nucleotide sequence UGAGAAGU (SEQ ID NO: 1275).

Examples and guidance related to type V or type VI CRISPR/Cas guide RNAs (e.g., cpf1, C2c1, C2c2, and C2c3 guide RNAs) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

Donor DNA Template

As noted above, in some cases, an RNP of the present disclosure comprises: a) a fusion site-directed modifying polypeptide (e.g., a class 2 CRISPR/Cas polypeptide) of the present disclosure; b) a guide RNA; and c) a donor DNA polynucleotide. In some cases, a method of the present disclosure for modifying a target nucleic acid comprises contacting a eukaryotic cell comprising a target nucleic acid with an RNP of the present disclosure, where the RNP comprises: a) a fusion site-directed modifying polypeptide of the present disclosure (e.g., a class 2 CRISPR/Cas polypeptide); b) a guide RNA; and c) a donor DNA polynucleotide. In some cases, the contacting occurs under conditions that are permissive for nonhomologous end joining (NHEJ) or homology-directed repair (HDR). In some cases, the target DNA is contacted with the donor polynucleotide (donor DNA template), wherein the donor polynucleotide, a portion of the donor polynucleotide, a copy of the donor polynucleotide, or a portion of a copy of the donor polynucleotide integrates into the target DNA.

In some cases, the donor polynucleotide comprises a nucleotide sequence that includes at least a segment with homology to the target DNA sequence, and the subject methods may be used to add, i.e. insert or replace, nucleic acid material to a target DNA sequence (e.g. to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., a promoter, a polyadenylation signal, an internal ribosome entry sequence (IRES), a 2A peptide, a start codon, a stop codon, a splice signal, a localization signal, etc.), to modify a nucleic acid sequence (e.g., introduce a mutation), and the like. As such, a complex (RNP) comprising a guide RNA and a fusion site-directed modifying polypeptide (e.g., a fusion class 2 CRISPR/Cas polypeptide) of the present disclosure is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, anti-pathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into a target DNA sequence, a polynucleotide comprising a donor sequence to be inserted is also provided to the cell, e.g., a donor polynucleotide is included in an RNP of the present disclosure. By a "donor sequence" or "donor polynucleotide" it is meant a nucleic acid sequence to be inserted at the cleavage site induced by a fusion site-directed modifying polypeptide (e.g., a fusion class 2 CRISPR/Cas polypeptide) of the present disclosure. The donor polynucleotide will contain sufficient homology to a genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor nucleic acid may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor nucleic acid at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor nucleic acid may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor nucleic acid, additional lengths of sequence may be included outside of the regions of homology that can be degraded without adversely affecting recombination. A donor nucleic acid can be introduced into a cell as part of a vector molecule having additional sequences such as, for example, replication origins, promoters and genes encoding antibiotic resistance. Moreover, a donor nucleic acid can be introduced as naked nucleic acid, as nucleic acid complexed with an agent such as a liposome or poloxamer, or can be delivered by a virus (e.g., adenovirus, adeno-associated virus, etc.).

Methods of Target Nucleic Acid Modification

A fusion site-directed modifying polypeptide (e.g., a fusion class 2 CRISPR/Cas polypeptide), or an RNP comprising same, is useful in a variety of methods for target nucleic acid modification, which methods are also provided.

A fusion site-directed polypeptide of the present disclosure, or an RNP of the present disclosure, can be used in any method in which a Cas9 protein or a Cpf1 protein can be used. For example, a fusion site-directed polypeptide of the present disclosure, or an RNP of the present disclosure, can be used to (i) modify (e.g., cleave, e.g., nick; methylate; etc.) a target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Because a method that uses a fusion sited-directed polypeptide includes binding of the fusion site-directed polypeptide to a particular region in a target nucleic acid (by virtue of being targeted there by an associated guide RNA (e.g., a Cas9 guide RNA or a Cpf1 guide RNA)), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid, modulation of translation of the target nucleic acid, genome editing, modulation of a protein associated with the target nucleic acid, isolation of the target nucleic acid, etc.). For examples of suitable methods, Cas9 variants, guide RNAs, etc., see, for example, Jinek et al., Science. 2012 Aug. 17; 337(6096): 816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 February 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et Al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

For example, the present disclosure provides methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like. The methods generally involve contacting a eukaryotic cell, which eukaryotic cell comprises a target nucleic acid, with a fusion site-directed modifying polypeptide (e.g., a fusion class 2 CRISPR/Cas polypeptide) of the present disclosure in complex with a guide RNA. In some cases, the methods comprising contacting a eukaryotic cell, which eukaryotic cell comprises a target nucleic acid, with an RNP comprising a fusion site-directed modifying polypeptide (e.g., a fusion class 2 CRISPR/Cas polypeptide) of the present disclosure and a guide RNA. In some cases, the methods comprising contacting a eukaryotic cell, which eukaryotic cell comprises a target nucleic acid, with: a) an RNP comprising a fusion site-directed modifying polypeptide (e.g., a fusion class 2 CRISPR/Cas polypeptide) of the present disclosure and a guide RNA; and b) a donor nucleic acid.

As used herein, the terms/phrases "contact a target nucleic acid" and "contacting a target nucleic acid", for example, with a fusion site-directed modifying polypeptide (e.g., a fusion class 2 CRISPR/Cas polypeptide) of the present disclosure, etc., encompass: 1) introducing a fusion site-directed modifying polypeptide (e.g., a fusion class 2 CRISPR/Cas polypeptide) of the present disclosure into a cell; and introducing a guide RNA (a Cas9 guide RNA or a Cpf1 guide RNA) into a cell by introducing the guide RNA itself into the cell; 2) introducing a fusion site-directed modifying polypeptide (e.g., a fusion class 2 CRISPR/Cas polypeptide) of the present disclosure into a cell; and introducing a guide RNA (Cas9 guide RNA or Cpf1 guide RNA) into a cell by introducing into the cell a nucleic acid encoding the guide RNA; 3) introducing into the cell an RNP comprising: i) a fusion site-directed modifying polypeptide (e.g., a fusion class 2 CRISPR/Cas polypeptide) of the present disclosure; and ii) a guide RNA (e.g., a Cas9 guide RNA, a Cpf1 guide RNA); 4) introducing into the cell a complex comprising: a) a donor polynucleotide; and b) an RNP comprising: i) a fusion site-directed modifying polypeptide (e.g., a fusion class 2 CRISPR/Cas polypeptide) of the present disclosure; and ii) a guide RNA (e.g., a Cas9 guide RNA, a Cpf1 guide RNA). As such, when, for example, performing a method in a cell (e.g., inside of a cell in vitro, inside of a cell in vivo, inside of a cell ex vivo), a method that includes contacting the target nucleic acid encompasses the introduction into the cell of the guide RNA in its active/final state (e.g., in the form of an RNA in some cases for the guide RNA), and also encompasses the introduction into the cell of one or more nucleic acids encoding one or more of the components (e.g., nucleic acid(s) having nucleotide sequence(s), nucleic acid(s) having nucleotide sequence(s) encoding guide RNA(s), and the like). Contacting a target nucleic acid encompasses contacting the target nucleic acid inside of a cell in vitro, inside of a cell in vivo, inside of a cell ex vivo, etc.

Target Nucleic Acids and Target Cells of Interest

A fusion site-directed modifying polypeptide (e.g., a fusion class 2 CRISPR/Cas polypeptide) of the present disclosure, when bound to a guide RNA, can bind to a target nucleic acid, and in some cases, can bind to and modify a target nucleic acid. A target nucleic acid can be any nucleic acid (e.g., DNA, RNA), can be double stranded or single stranded, can be any of a number of types of nucleic acid (e.g., a chromosome, derived from a chromosome, chromosomal, plasmid, viral, mitochondrial, chloroplast, linear, circular, etc.) and can be from any organism (e.g., as long as the guide RNA (e.g., Cas9 guide RNA, Cpf1 guide RNA) can hybridize to a target sequence in a target nucleic acid, such that target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded. In some cases, a target nucleic acid is a double-stranded DNA.

A target nucleic acid can be located within a eukaryotic cell, for example, inside of a eukaryotic cell in vitro, inside of a eukaryotic cell in vivo, inside of a eukaryotic cell ex vivo. Suitable target cells (which can comprise target nucleic acids) include, but are not limited to: a single-celled eukaryotic organism; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens C. agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), a somatic cell, e.g. a fibroblast, an oligodendrocyte, a glial cell, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

Target cells include in vivo target cells. Target cells include retinal cells (e.g., Müller cells, ganglion cells, amacrine cells, horizontal cells, bipolar cells, and photoreceptor cells including rods and cones, Müller glial cells, and retinal pigmented epithelium); neural cells (e.g., cells of the thalamus, sensory cortex, zona incerta (ZI), ventral tegmental area (VTA), prefontal cortex (PFC), nucleus accumbens (NAc), amygdala (BLA), substantia nigra, ventral *pallidum*, globus pallidus, dorsal striatum, ventral striatum, subthalamic nucleus, hippocampus, dentate gyrus, cingulate gyms, entorhinal cortex, olfactory cortex, primary motor cortex, or cerebellum); liver cells; kidney cells; immune cells; cardiac cells; skeletal muscle cells; smooth muscle cells; lung cells; and the like.

Where the target cell is an in vivo retinal cell, an RNP of the present disclosure (e.g., an RNP comprising: i) a fusion site-directed modifying polypeptide (e.g., a fusion class 2 CRISPR/Cas polypeptide) of the present disclosure; and ii) a guide RNA) can be administered via intraocular injection, by intravitreal injection, by intravitreal implant, subretinal injection, suprachoroidal administration, intravenous administration, or by any other convenient mode or route of administration.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA). Because the guide RNA provides specificity by hybridizing to target nucleic acid, a mitotic and/or post-mitotic cell of interest in the disclosed methods may include a cell from any organism (e.g. a single-celled eukaryotic organism, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent (e.g., mouse; rat), a cell from a human, etc.).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Constructs encoding Cas9, with various numbers of NLS at the N-terminus of the Cas9 protein, and 2 NLSs at the C-terminus of the Cas9 protein, were generated. The NLS-modified Cas9 protein produced included, from N-terminus to C-terminus: a) 0, 1, 2, 3, or 4 NLSs; b) Cas9; c) 2 NLSs; and a superfolder green fluorescent protein (sfGFP). The amino acid sequences of the N-terminal and C-terminal NLS-containing regions are depicted in FIG. 2A. The NLS-modified Cas9 proteins were combined with guide RNA to generate RNPs. The RNPs were tested for passive uptake into neural stem cells in vitro. The data are depicted in FIG. 2A-2D.

FIG. 2A-2D. 4×N-Terminal NLS on Cas9 Significantly Improves Passive Cas9 RNP Uptake and Genome-Editing in Neural Stem Cells in Culture.

Figure 2D:
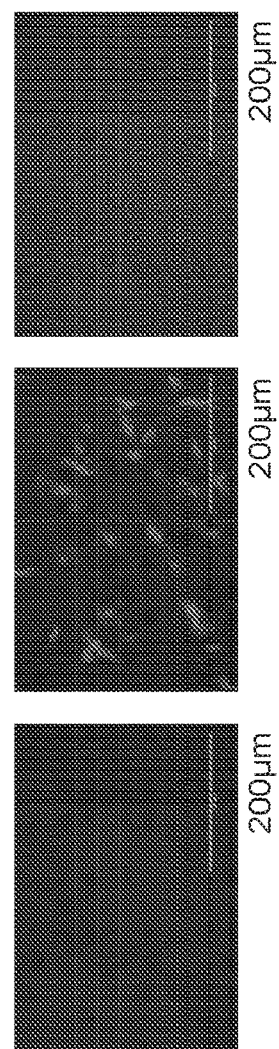

FIG. 2A shows design of Cas9 protein with various numbers of N-terminal NLS. FIG. 2B: tdTomato reporter system activates expression of tdTomato Red Fluorescent Protein (RFP) in genome-edited cells. 4×NLS-Cas9 design is significantly more efficient at genome-editing cells than other designs. FIG. 2C: Representative pictures of cells, scale bar 1000 µm. FIG. 2D: Representative pictures of cells, scale bar 200 µm.

A construct encoding a *Streptococcus pyogenes* Cas9 (SpyCas9) with 4 NLSs at the N-terminus and 2 NLSs at the C-terminus was generated. The 4×NLS-SpyCas9-2×NLS included a superfolder green fluorescent protein (sfGFP) at the C-terminus. The encoded protein is referred to as "4×NLS-SpyCas9-2×NLS-sfGFP." The amino acid sequence of the 4×NLS-SpyCas9-2×NLS-sfGFP polypeptide is depicted in FIG. 7. The 4×NLS-SpyCas9-2×NLS-sfGFP polypeptide was incorporated into ribonucleoprotein (RNP) with guide RNA. The data are shown in FIG. 3-6.

FIG. 3.

Figure 3:
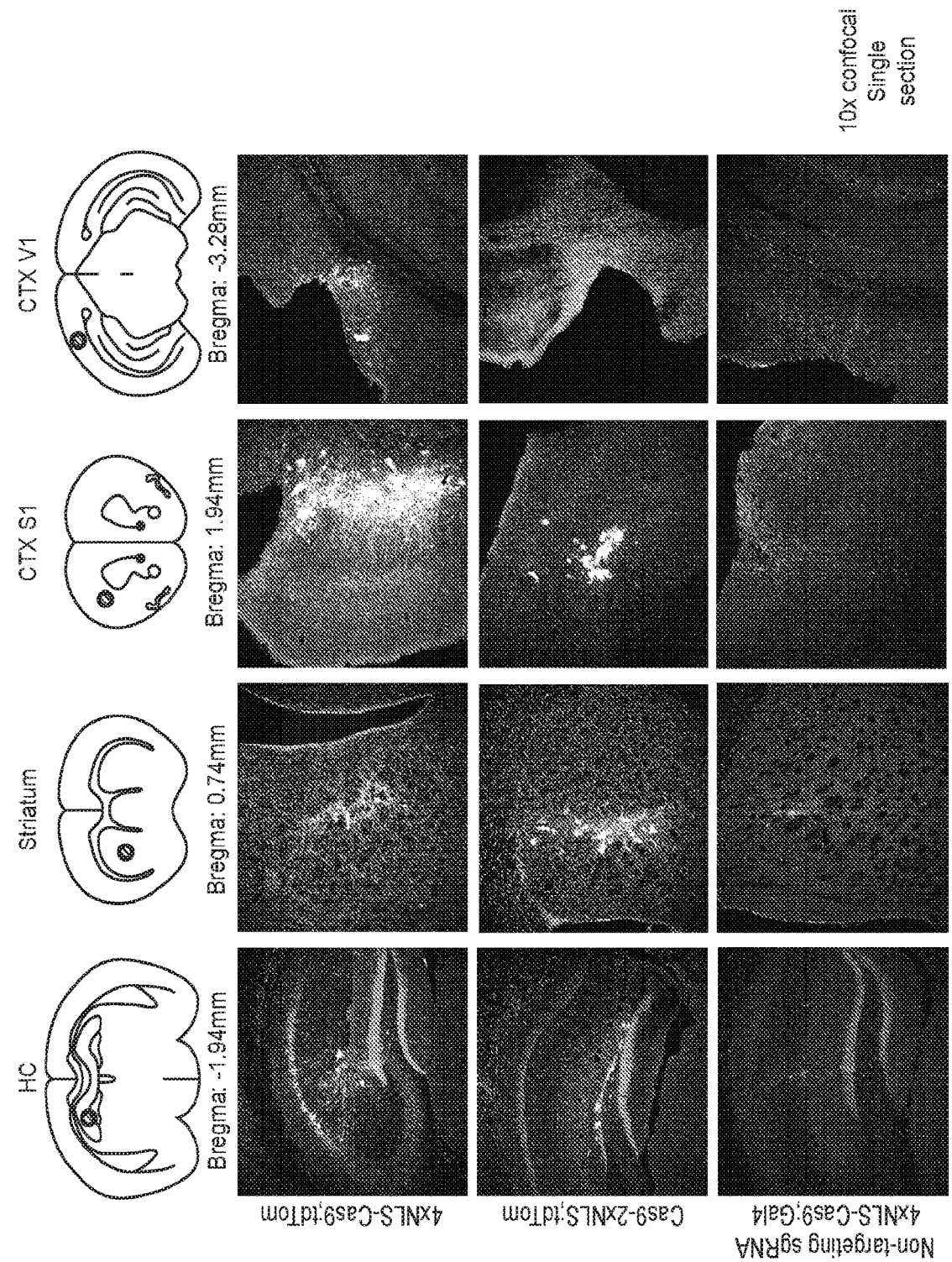
FIG. 3 depicts genome editing following injection of Cas9 RNP into multiple brain regions.

Experimental plan: The Cas9 constructs and single-guide RNAs (sgRNAs) were as follows: a) 2 Cas9 constructs: i) Cas9-2×NLS-sfGFP; and ii) 4×NLS-Cas9-2×NLS-sfGFP; b) 2 sgRNAs: i) tdTomato(298), 5'-AAGTAAAACCTCTA-CAAATG-3' (SEQ ID NO:1312); and ii) non-targeting Gal4 (339), 5'-AACGACTAGTTAGGCGTGTA-3' (SEQ ID NO:1313). The RNP was delivered in a per-dose concentration of 4 pmol/0.5 µl. Four injection sites were used: HC=Hippocampus, S=Striatum, CTX S1=Primary Somatosensory Complex (S1), CTX V1=Primary Visual Cortex V1. Three mice were injected for each injection site. The mice were 14-15 weeks old. 24 total animals. Brains were analyzed 12-14 days post injections. The data are depicted in FIG. 3. As shown in FIG. 3, injection of Cas9 RNP into multiple brain regions results in precise genome-editing.

FIG. 4A-4D. 4×NLS-Cas9 Significantly Improves In Vivo Cortical Cas9 RNP Genome-Editing.

Figure 4A:
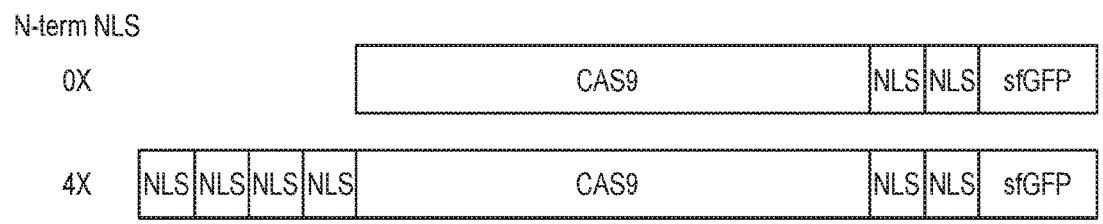
FIG. 4A-4D depict the effect of 4×NLS-Cas9 on in vivo Cas9/RNP-mediated genome editing.
Figure 4B:
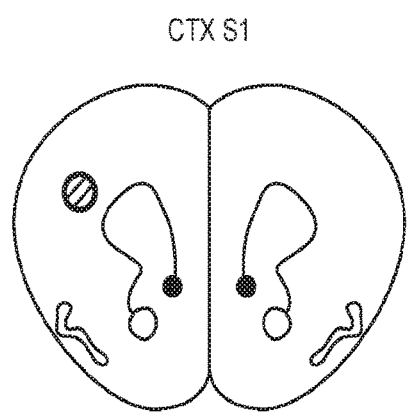
Figure 4D:
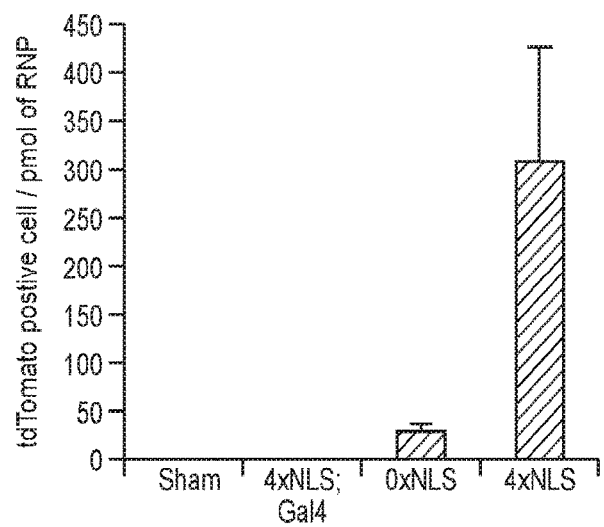
Figure 4C:
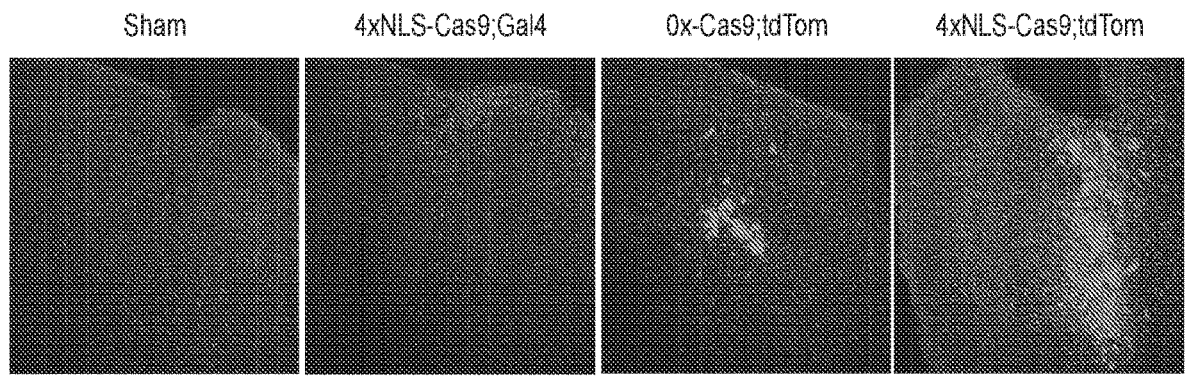

FIG. 4A: Schematic of Cas9 proteins used for in vivo injections. FIG. 4B: 4 pmol Cas9 RNP in 0.5 µl volume was injected into CTX S1=Primary Somatosensory Complex (S1). Red dot is injection location. FIG. 4C: Representative pictures of brain sections with genome-edited cells expressing tdTomato RFP. FIG. 4D: Quantification of genome-edited tdTomato positive cells per pmol Cas9 RNP. Cas9 construct; sgRNA. Sham is injection buffer only. tdTom sgRNA targets tdTomato reporter locus. Gal4 is a non-targeting sgRNA control and neither targets nor edits the tdTomato locus. The data indicate that 4×NLS-Cas9 significantly improves in vivo cortical Cas9 RNP genome-editing.

FIG. 5A-5D. 4×NLS-Cas9 Significantly Improves In Vivo Hippocampal Cas9 RNP Genome-Editing.

Figure 5A:
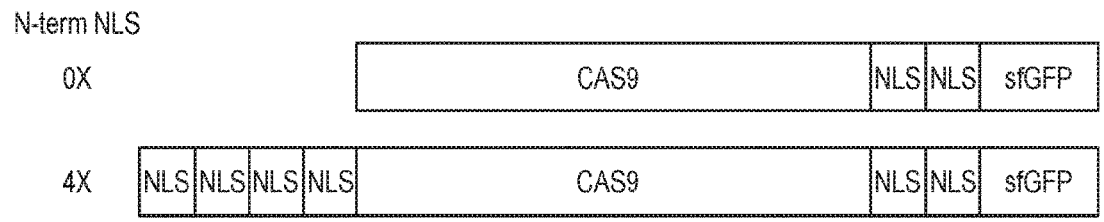
FIG. 5A-5D depict the effect of 4×NLS-Cas9 on in vivo hippocampal Cas9/RNP-mediated genome editing.
Figure 5B:
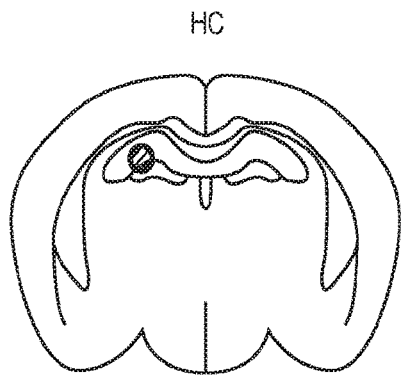
Figure 5D:
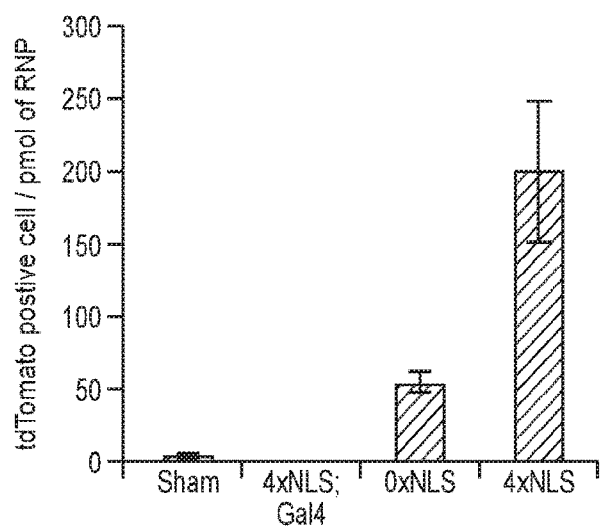
Figure 5C:
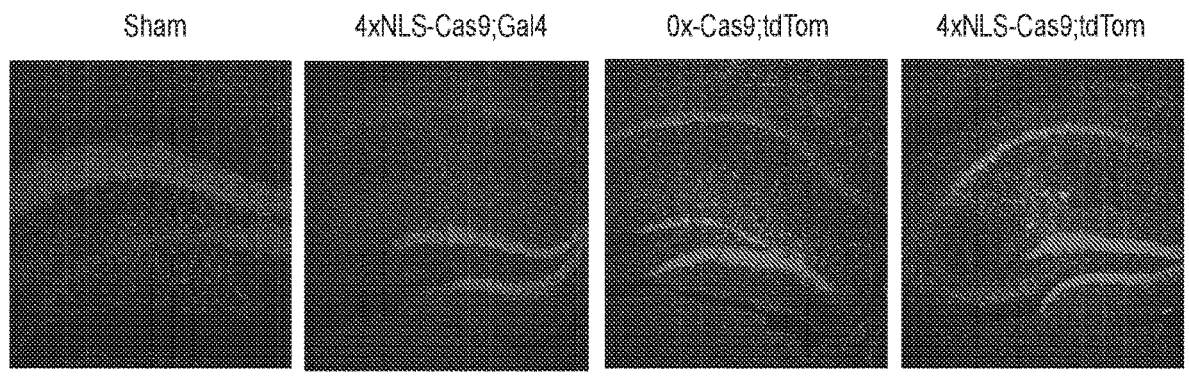

FIG. 5A. Schematic of Cas9 proteins used for in vivo injections. FIG. 5B: 4 pmol Cas9 RNP in 0.5 µl volume was injected into the Hippocampus. Red dot is injection location. FIG. 5C: Representative pictures of brain sections with genome-edited cells expressing tdTomato RFP. FIG. 5D: Quantification of genome-edited tdTomato positive cells per pmol Cas9 RNP. Cas9 construct; sgRNA. Sham is injection buffer only. tdTom sgRNA targets tdTomato reporter locus. The data indicate that 4×NLS-Cas9 significantly improves in vivo hippocampal Cas9 RNP genome-editing.

Figure 6A:
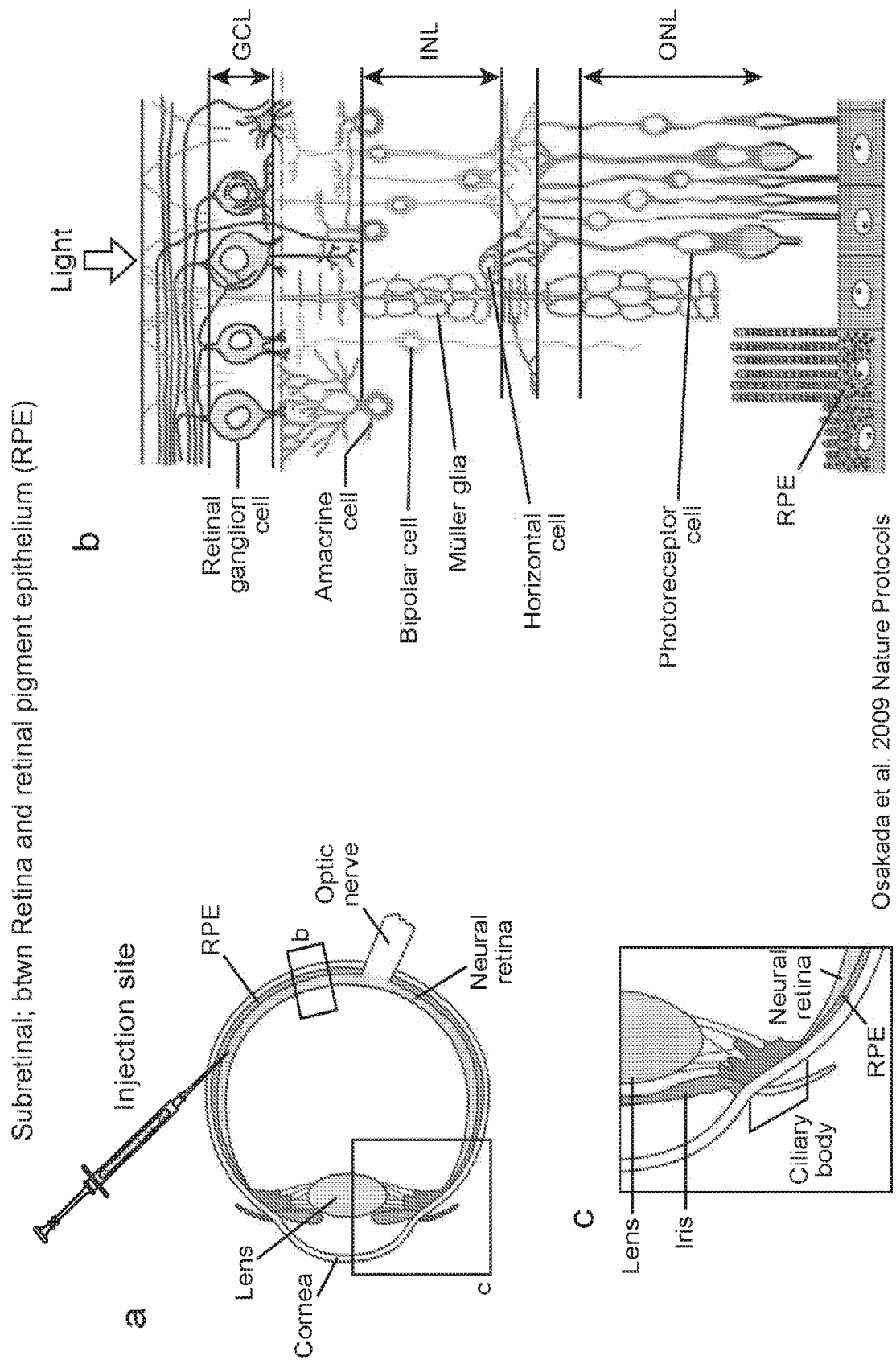
FIG. 6A-6C depict the effect of subretinal Cas9/RNP injections on genome editing in the retina.
Figure 6B:
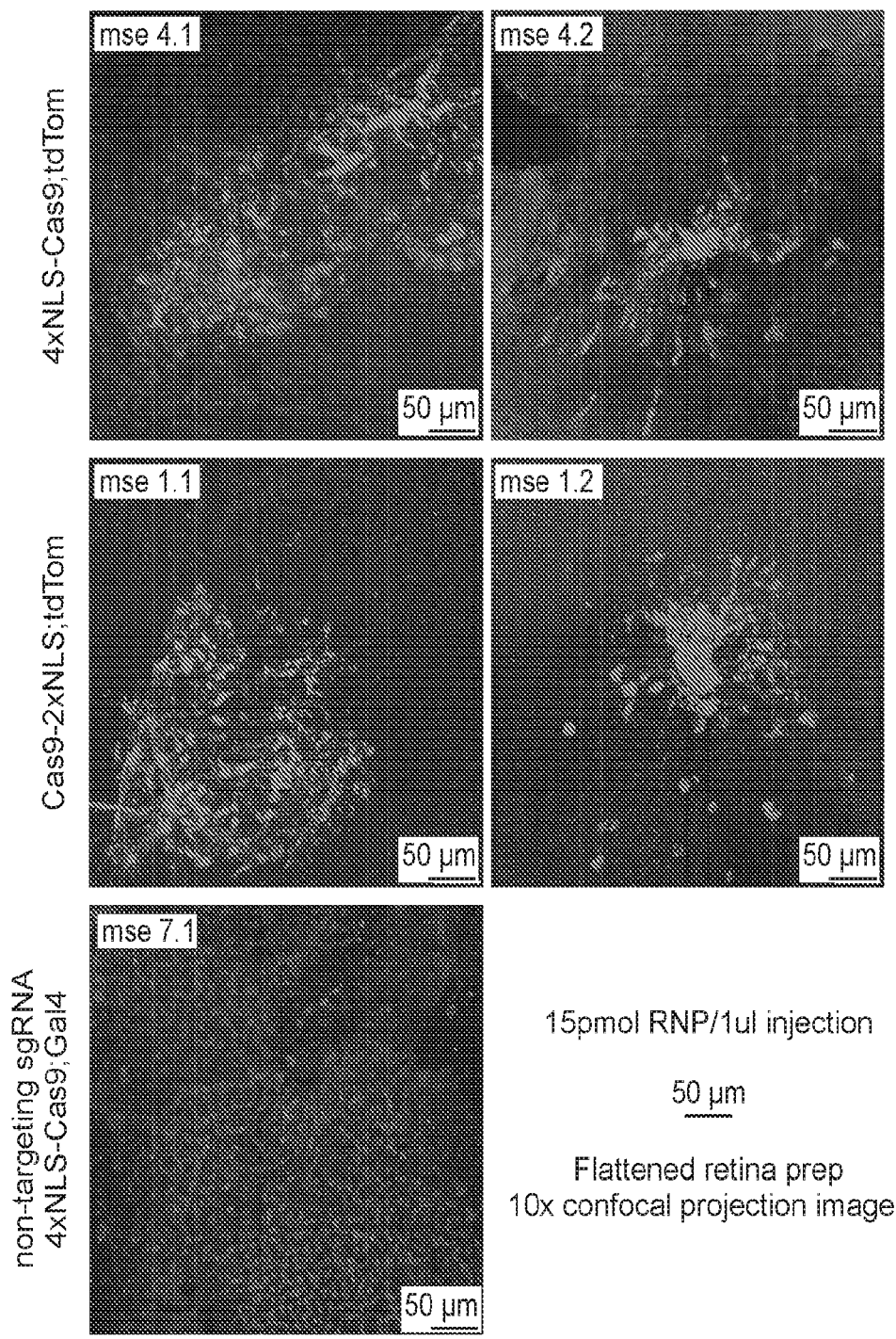
Figure 6C:
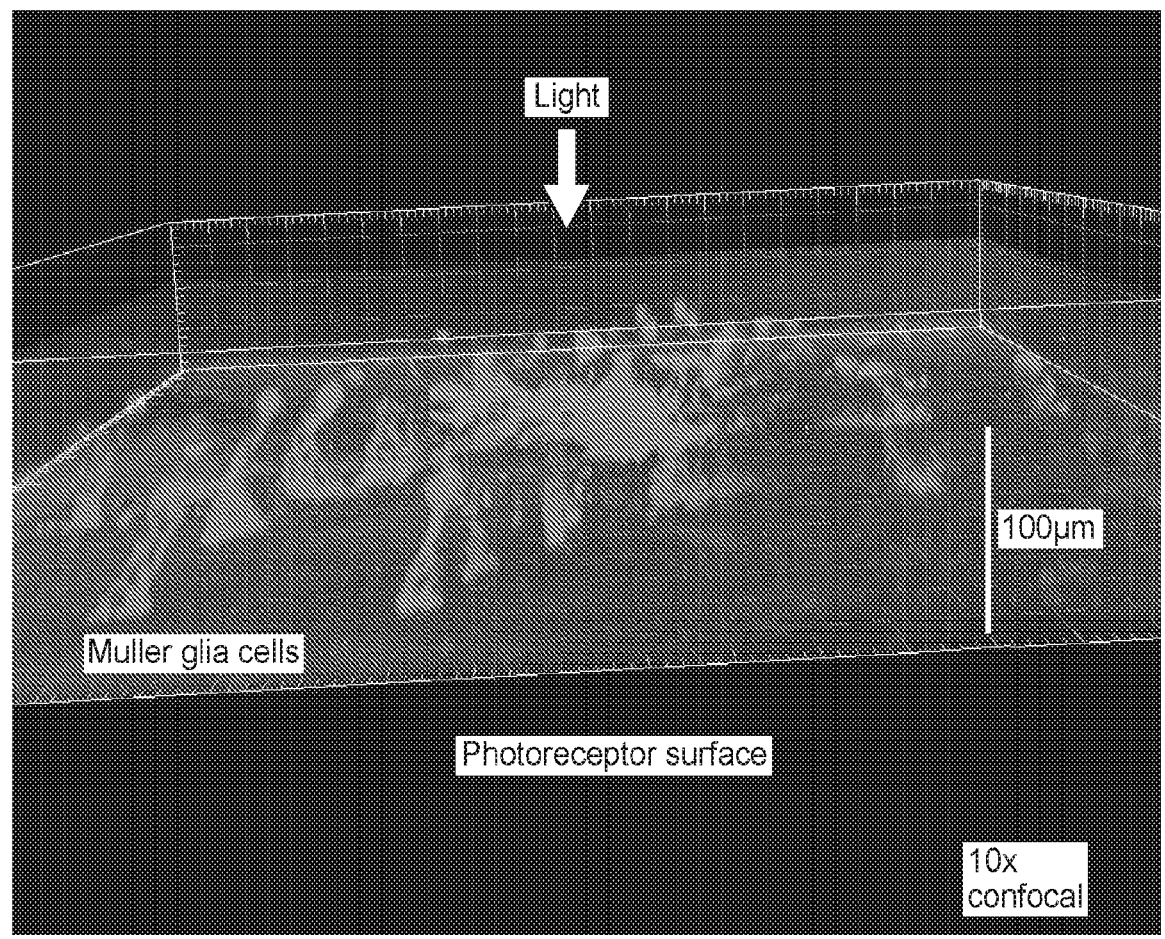

FIG. 6A-6C. Subretinal Cas9 RNP Injections: Genome-Editing in Retina Includes Cells Surrounding Injection Site and Distal Müller Glia.

FIG. 6A presents a schematic of Subretinal injection site. FIG. 6B: 15 pmol Cas9 RNP in 1 µl volume was injected subretinal. tdTomato+ cells report precise genome-editing by Cas9 RNP. Non-targeting Gal4 sgRNA does not activate tdTomato reporter gene. FIG. 6C: Volume display of mse 4.2, 4×NLS-Cas9 RNP, showing Cas9-edited Müller glia cells expressing tdTomato.

Figure 9:
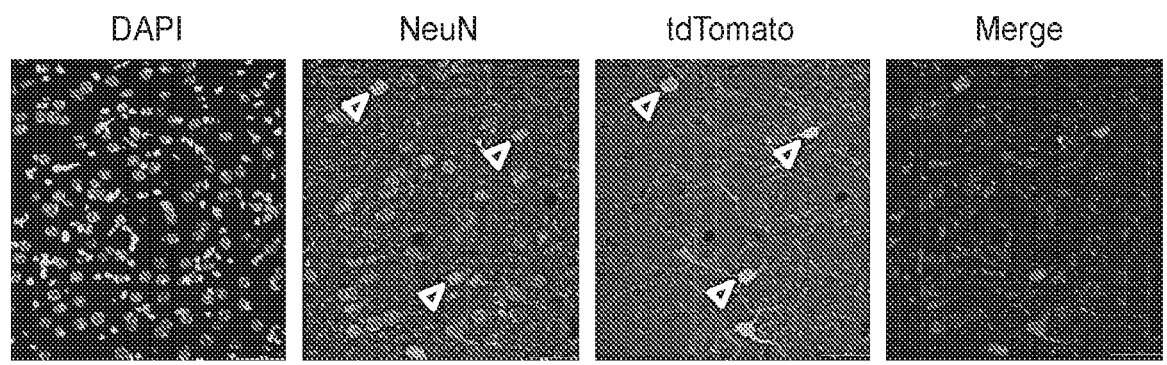
FIG. 9 depicts antibody staining of brain sections from 4×-NLS-Cas9 RNP genome-edited animals.

FIG. 9. Antibody Staining of Brain Sections from 4×-NLS-Cas9 RNP Genome-Edited Animals.

The images are confocal microscopy images. Colocalization with the marker proteins identifies the edited tdTomato+ neurons. Scale bar is 50 µm. CTIP2: aka BCL 11 a, a Transcription factor present in CA 1 Hippocampus and Striatum neurons. GFAP: Glial fibrillary acidic protein is an intermediate filament (IF) protein that is expressed by numerous cell types of the central nervous system (CNS) including astrocytes, and ependymal cells. DARP-32: cAMP-regulated neuronal phosphoprotein, a well-documented marker of Striatum Medium Spiny Neurons. NeuN: a neuronal specific nuclear protein in vertebrates.

Example 2

Materials and Methods:

Neural Progenitor Cell (NPCs) Line Creation:

NPCs were isolated from cortices from Embryonic Day 13.5 Ai9-tdTomato homozygous mouse embryos (Madisen et al. 2009. *Nat. Neurosci.* 13:133-140). Cells were cultured as neurospheres in NPC Medium: DMEM/F12 with glutamine, Na-Pyruvate, 10 mM HEPES, Non-essential amino acid. Pen/Strep (100×), 2-mercaptoethanol (1000×), B-27 without vitamin A, N2 supplement, bFGF and EGF, both 20 ng/ml as final concentration. NPCs were passaged using MACS Neural Dissociation Kit (Papain) cat #130-092-628 following manufacturer's protocol. bFGF and EGF were refreshed every other day and passaged every six days. The NPC line was authenticated by immunocytochemistry marker staining; the cell line was tested for *mycoplasma* using Hoechst stain with visual analysis and was negative.

HEK293T-EGFP-PEST Cell Line Creation:

The d2EGFP reporter construct was created in a modified lentivirus backbone with EF1-a promoter driving the gene of interest and a second PGK promoter driving production of a gene which confers resistance to hygromycin. The EGFP is destabilized by fusion to residues 422-461 of mouse ornithine decarboxylase, giving an in vivo half-life of ~2 hours. Transduced 293T cells were selected with hygromycin (250 μg/ml). d2EGFP clones were isolated by sorting single cells into 96 well plates and characterized by intensity of d2EGFP. Lentivirus was produced by PEI (Polysciences Inc., 24765) transfection of 293T cells with gene delivery vector co-transfected with packaging vectors pspax2 and pMD2.G essentially as described by (Tiscornia et al. 2006, *Nature Protocols*. 1:241-245). The parental HEK293T cell line was obtained from UC Berkeley Scientific Facilities and authenticated using STR analysis by DDCM; the cell line wasted for *mycoplasma* using Hoechst stain with visual analysis and was negative.

HEK 293T EGFP Disruption Assay:

GFP disruption assays were based on those previously described (Gilbert et al. 2013, *Cell*. 154:442-451). HEK-293T-d2EGFP cells were used in this experiment because they are efficiently transfected with Cas9-RNP mixed with lipofectamine2000 and therefore useful for this experiment which is analyzing the activity of the 0xNLS- and 4xNLS-Cas9 RNPs post cell penetration. Briefly, HEK293T-d2EGFP cells were cultured in 10 cm dishes using Dulbecco's Modification of Eagle's Medium (DMEM) with 4.5 g/L glucose L-glutamine & sodium pyruvate (Corning cellgro) plus 10% fetal bovine serum, 1xMEM Non-Essential Amino Acids Solution (Gibco) and Pen-Strep (gibco). One day before transfection ~3x10^4 cells were plated into each well of a 96 well plate with the DMEM medium plus hygromycin and allowed to settle. The next day Cas9 RNP was complexed with Lipofectamine 2000 (Life Technologies) at 0.005-50 pmol RNP+1 μl Lipofectamine in 20 μl OMEM media and added to the cells. Cells were analyzed for EGFP expression at 48 hours post transfection using a BD LSR Fortessa High-throughput sequencer.

Cas9 Purification:

The recombinant *S. pyogenes* Cas9 used in this study carries two C-terminal SV40 nuclear localization sequences. The protein was expressed with a N-terminal hexahistidine tag and maltose binding protein in *E. coli* Rosetta 2 cells (EMD Millipore, Billerica, Mass.) from plasmids based on pMJ915 (Addgene plasmid #69090) (Lin et al. 2014, *eLife*. 3:e04766). N-terminal nuclear localization sequence peptide arrays and sfGFP modifications were cloned into the plasmid using Gibson DNA assembly technique (FIG. 19). The His tag and maltose binding protein were cleaved by TEV protease, and Cas9 was purified by the protocols described in (Jinek et al. 2012, *Science*. 337:816-821). Cas9 was stored in "Buffer 5": 20 mM 2-[4-(2-hydroxyethyl)piperazin-1-yl] ethanesulfonic acid (HEPES) at pH 7.5, 150 mM KCL, 10% glycerol, 1 mM tris(2-chloroethyl) phosphate (TCEP) and stored at −80° C. For in vivo experiments Cas9 was buffer exchanged into "Buffer #1": 25 mM Na phosphate pH 7.25, 300 mM NaCl, 200 mM 300 trehalose before size exclusion column and stored at −80° C. Cas9 protein endotoxin levels were measured using Pierce LAL Chromogenic Endotoxin Quantification Kit Cat. #88282.

FIG. 19 provides the primary sequence data for N-terminal NLS-Cas9 fusions.

sgRNA Target Site Prediction:

sgRNA target sequences were selected using the website accessed by entering "http:" followed by "//crispr.mit" followed by".edu" into an internet browser (Hsu et al. 2013. *Nat. Biotechnol.* 31:827-832).

In Vitro T7 Transcription of sgRNA:

The DNA template encoding for a T7 promoter, a 20 nt target sequence and an optimized sgRNA scaffold (Chen et al. 2013, *Cell*. 155:1479-1491) was assembled from synthetic oligonucleotides (Integrated DNA Technologies, San Diego, Calif.) by overlapping polymerase chain reaction (PCR). Target sequences are: sgRNA298/tdTom (targets STOP cassette in tdTomato locus), 5'-AAGTAAAACCTC-TACAAATG-3' (SEQ ID NO:1312), sgRNA non-targeting (aka sgRNA339 targets Gal4 sequence that is not present in mouse genome), 5'-AACGACTAGTTAGGCGTGTA-3' (SEQ ID NO:1313), sgRNA-NT3 (targets EGFP gene) 5'-GGTGGTGCAGATGAACTTCA-3' (SEQ ID NO:1314). Briefly, for the sgRNA298/tdTom template, the PCR reaction contains 20 nM premix of BS298 (5'-TAA TAC GAC TCA CTA TAG AAG TAA AAC CTC TAC AAA TGG TTT AAG AGC TAT GCT GGA AAC AGC ATA GCA AGT TTA AAT AAG G-3') (SEQ ID NO:1315) and BS6 (5'-AAA AAA AGC ACC GAC TCG GTG CCA CTI TT CAA GTT GAT AAC GGA CTA GCC TTA TTT AAA CTT GCT ATG CTG TTT CCA GC-3') (SEQ ID NO:1316), 1 μM premix of T25_long (5'-GAA ATT AAT ACG ACT CAC TAT AG-3') (SEQ ID NO:1317) and BS7 (5'-AAA AAA AGC ACC GAC TCG GTG C-3') (SEQ ID NO:1318), 200 μM dNTP and Phusion Polymerase (NEB, Ipswich, Mass.) according to manufacturer's protocol. The thermocycler setting consisted of 40 cycles of 95° C. for 10 s, 59° C. for 10 s and 72° C. for 10 s. The PCR product was extracted once with phenol:chloroform:isoamylalcohol and thenonce with chloroform, before isopropanol precipitation overnight at −20° C. The DNA pellet was washed three times with 70% ethanol, air-dried and resuspended in Elution Buffer.

An 400-μl T7 in vitro transcription reaction consisted of 50 mM Tris-HCl (pH 8), 30 mM $MgCl_2$, 0.01%

325 Triton X-100, 2 mM spermidine, 20 mM fresh dithiothreitol, 5 mM of each ribonucleotide triphosphate, 100 μg/ml T7 Pol and 1 μM DNA template. The reaction was incubated at 37° C. for 4 hr-to-overnight, and 5 units of RNase-free DNaseI (Promega, Madison, Wis.) was added to digest the DNA template 37° C. for 1 hr. The reaction was quenched with 2xSTOP solution (95% deionized formamide, 0.05% bromophenol blue and 20 mM EDTA) at 60° C. for 5 min. The RNA was purified by electrophoresis in 10% polyacrylamide gel containing 6 M urea. The RNA band was excised from the gel, grinded up in a 15-ml tube, and eluted with 5 vol of 300 mM sodium acetate (pH 5) overnight at 4° C. The supernatant was filtered through a 0.2 um filter to remove acrylamide fragments. 2.5 equivalents of ethanol was added to precipitate the RNA overnight at −20° C. The RNA pellet was collected by centrifugation, washed three times with 70% ethanol, and air-dried or vacuum-dried. To refold the sgRNA, the RNA pellet was re-dissolved in dPBS-Ca,-Mg. The sgRNA was heated to 70° C. for 5 min and cooled to room temperature for 5 min. $MgCl_2$ was added to a final concentration of 1 mM. The sgRNA was again heated to 50° C. for 5 min, cooled to room temperature for 5 min and kept on ice. The sgRNA concentration was determined by OD260 nm using Nanodrop (Thermo Fisher Scientic, Waltham, Mass.). The sgRNA was stored at −80° C.

Cas9 RNP Assembly:

Cas9 RNP either was prepared immediately before experiments or prepared and snap-frozen in liquid nitrogen and frozen at −80 C for later use. Loss in activity upon freeze-thawing Cas9 RNP complexes was not measured. To prepare the Cas9 RNP complexes Cas9 protein was incubated with sgRNA at 1:1.2 molar ratio. Briefly sgRNA was added to Buffer #1 (25 mM NaPi, 150 mM NaCl, 200 mM trehalose, 1 mM $MgCl_2$). Then the Cas9 was added to the sgRNA, slowly, swirling it in. The mixture was incubated at 37° C. for 10 min to form RNP complexes. Filtration step: 0.22 um Costar Filter 8160 was wet with 200 ul Buffer #1, spun at 15 k×g for 1 min. Buffer #1 was removed from tube and RNP was added to filter, spun at 15 k×g for 1 min. If needed the RNP was concentrated in Millipore Ultra 100Kd cutoff, 0.5 ml FC510096. Spun at 14 k×g for 3 min to desired volume (ul). Flipped and spun out at 1 k×g for 2 min.

Cas9 Nucleofection:

NPCs were dissociated by the MACS Neural Dissociation Kit (Papain) cat #130-092-628, spun down by centrifugation at 80×g for 3 min, and washed once with dPBS-Ca,-Mg. Nucleofection of NPCs with Cas9 RNP was performed using Lonza (Allendale, N.J.) P3 cell kits and program EH-100 in an Amaxa 96-well Shuttle system. Each nucleofection reaction consisted of approximately $2.5 \times 10^5$ cells in 20 μl of nucleofection reagent and mixed with 10 μl of RNP. After nucleofection, 70 μl of growth media was added to the well to transfer the cells to tissue culture plates. For plasmid nucleofection a modified pX330-U6-Chimeric_BB-CBh-hSpCas9 vector was used (was a gift from Feng Zhang (Addgene plasmid #42230)) (Cong et al. 2013, *Science*. 339:819-823) that contained puromycin N-acetyltransferase PuroR gene and optimized sgRNA scaffold (Chen et al. 2013, *Cell*. 155:1479-1491). Nucleofection was done with 700 ng plasmid with $4 \times 10^5$ NPCs and Lonza P3 cell kit and program DS-113 in an Amaxa 96-well Shuttle system. The cells were incubated at 37° C. for 1-5 days depending on the assay. For genomic DNA analysis the media was removed by aspiration, and 100 μl of Quick Extraction solution (Epicentre, Madison, Wis.) was added to lyse the cells (65° C. for 20 min and then 95° C. for 20 min) and extract the genomic DNA. The cell lysate was stored at −20° C. The concentration of genomic DNA was determined by NanoDrop. tdTomato activation in NPCs were analyzed by FACS. UC Berkeley FACS Core facilities were used.

Animals:

Mice were maintained on a 12 h light dark cycle with ad libitum access to food and water. All animals were group housed and experiments were conducted in strict adherence to the Swiss federal ordinance on animal protection and welfare as well as according to the rules of the Association for Assessment and Accreditation of Laboratory Animal Care International (AAALAC), and with the explicit approval of the local veterinary authorities. Animals at University of California, Berkeley were maintained on a 12 h light dark cycle with ad libitum access to food and water. All animals were group housed and experiments were conducted in strict adherence to the University of California, Berkeley's Animal Care and Use Committee (ACUC) ethical regulations. No randomization was used to allocate animals to experimental groups.

Stereotaxic Infusion of Cas9 RNP's:

Cas9, 4×NLS-Cas9 and 4×NLS-Cas9-GFP RNPs were prepared and shipped by Brett Staahl, UC Berkeley to Roche Pharmaceuticals Basel, Switzerland. 15-20 weeks old male Ai14 tdTomato mice (which lack the NeoR cassette present in Ai9 tdTomato mice but are otherwise identical) (Madisen et al. 2009. *Nat. Neurosci.* 13:133-140) were anesthetized using injectable anesthesia (Fentanyl 0.05 mg/Kg+Medetomidine 0.5 mg/kg+Midazolam 5 mg/kg; s.c.). The anesthetized mouse was then aligned on an Angle two stereotactic frame (Leica, Germany) and craniotomies were performed with minimal damage to brain tissue. All stereotaxic coordinates were relative to bregma. Stereotaxic surgery targeted the mouse striatum (+0.74 mm anteroposterior, ±1.74 mm mediolateral, −3.37 mm dorsoventral). Cas9 RNPs were infused (Striatum—0.5 μl/side) using a Neuros 75 5 μL syringe (Hamilton). After infusion, the injector was left at the injection site for 5 min and then slowly withdrawn. After the injections, the operation field was cleaned with sterile 0.9% NaCl and closed with suture (Faden Monocryl Plus 5-0, Aichele Medico) and surgical glue (3M™ Vetbond™ Tissue Adhesive). The mouse was kept warm at 37° C. during the surgical procedure and also post-surgery. To avoid drying of the eyes during surgery, an ointment was applied outside of the eyes of the mouse. The mice were left undisturbed for 12 days before cellular analysis. Sample size was chosen based on expected effect size. No randomization was applied while allocating animals to groups.

Immunofluorescence:

For immunofluorescence, mice were perfused with 4% paraformaldehyde and post-fixed overnight. Brains were sectioned (coronal plane sections) on a vibratome and 50 μm thick sections were used for 0 antibody labeling. Sections were first treated with blocking solution (0.3% Triton X-100, 10% goat serum in 1×PBS) and incubated with the primary antibody (in blocking solution) overnight at 4° C. Sections were washed with 1×PBS and incubated in the secondary antibody at room temperature for 3 hours. Finally, sections were washed three times in 1×PBS, stained with the DNA binding fluorescence probe DAPI (1 μg/ml, Roche Life science, Switzerland) and mounted on glass slides in a Prolong gold anti-fade medium (Thermo Fischer, USA).

Primary antibodies used were polyclonal rabbit anti-IBA1 (1:100, Wako, #019-19741), polyclonal rabbit anti-S100β (1:1000; Abcam, #ab41548), monoclonal rabbit anti-DARPP32 (1;100, Cell signaling technologies, #2306), monoclonal mouse anti-NeuN (1:500; Millipore, #MAB377), Polyclonal chicken anti-GFAP (1:500; Abcam, #ab4674), and monoclonal rat anti-CTIP2 (1:100; clone 25B6, Abcam, #ab18465). Secondary antibodies used were donkey anti-rabbit Alexa Fluor 488 (1:500, Jackson Lab, USA, #711-545-152), and donkey anti-rat Alexa Fluor 488 (1:500, Thermo Fischer, USA, #A-21208), donkey anti-chicken Alexa Fluor 488 (1:500; Jackson Labs, Bar Harbor, Me., #703-545-155), donkey anti-mouse Alexa Fluor 488 (1:500; Jackson Labs, Bar Harbor, Me., #715-545-150).

Confocal Imaging:

Confocal fluorescent images were acquired using a Leica TCS SP5 (Leica Microsystems) inverted microscope. Image analysis and maximum intensity projections of images acquired along the z-axis was done using LAS-AF software.

Cell Counting:

Images for cell counting were acquired using a Leica TCS SP5 (Leica Microsystems) inverted microscope with 20× dry objective. Image analysis and maximum intensity projections of images acquired along the z-axis was done using LAS-AF software. Every sixth section from the dorsal striatum was stained with DAPI and used for cell counting. Quantification of Td-tomato and DAPI double positive cells was done using ImageJ. The total number of edited cells per brain was quantified by multiplying the number of cells counted with the section periodicity (here it was 6). The experimenter was blinded to treatment condition while performing cell counting.

Quantification of Fluorescence Intensity:

Images for quantification were acquired a Leica TCS SP5 (Leica Microsystems) inverted microscope with 20× dry objective. All parameters were kept constant to allow comparative measurements between images. To quantify the fluorescence intensity corresponding to microglia (IBA-1 staining) at the injection site, reconstruction of the injection site of the slice was performed by recording at least 140 single optical layers (step size system optimized of 0.18 mm) at a 512-512 pixel resolution. The brightest sample was used to define optimal confocal settings with such settings used for the acquisition of all subsequent z stacks. LAS AF Lite software was used to reconstruct 3D Projection of the section. Quantification of the intensity of IBA-1 staining in the striatum was done with ImageJ Software. Data are represented as mean±SEM (One way ANOVA; p=0.4496 and F2, 7=0.898). n=3 animals per condition with 2-8 cells analyzed per animal. The experimenter was blinded to treatment condition while performing quantitation of fluorescence intensity.

GUIDE-Seq:

GUIDE-Seq samples were prepared as described (Tsai et al. 2014, Nat. Biotechnol. 33:187-197). Cortical neurons were isolated from post-natal day 0 (P0), Ai9 tdTomato mice. $4 \times 10^5$ cells in 20 µl Lonza P3 buffer+100 pmol dsODN in 1 µl hybridization buffer+40 pmol of 1 of 4 RNP complexes: 0×NLS-Cas9;sgRNAtdTom, 4×NLS-Cas9;sgRNAtdTom, 0×NLS-Cas9;sgRNAGal4 or 4×NLS-Cas9;sgRNAGal4 in 10 ul Buffer #1. Cells were nucleofected with program CL-133 of the Amaxa shuttle system and genomic DNA collected 5 days later using Quick Extraction solution (Epicentre, Madison, Wis.).

GUIDE-seq analysis: The GUIDE-seq analysis package was used with default options (retrieved from the website accessed by entering https://followed by "github." followed by "com/aryeelab/guideseq" into an internet browser on Aug. 10, 2016). A synthetic genome was created by inserting the tdTomato transgene (Ai9 was a gift from Hongkui Zeng (Addgene plasmid #22799)) (Madisen et al. 2009. Nat. Neurosci. 13:133-140) into mm10 at chromosome 6 between coordinates 113075330 and 113076736 and was used for the alignment step. In some embodiments, possibly due to the repetitive nature of the tdTomato target site (FIG. 11), the bwa aligner assigned low MAPQ scores to the alignments. Therefore, the GUIDE-seq analysis package was modified to report all alignments regardless of MAPQ score. The GUIDE-seq reads were also mapped onto a synthetic genome containing only one repeat of the stop cassette and obtained similar results, although the version with three repeated stop cassettes was ultimately used as in some embodiments, it may be a more faithful representation of the genome of the Ai9 and Ai14 tdTomato mouse lines. UC Berkeley Genome Sequencing Core Facilities were used.

Results:

Cas9 RNP Editing of tdTomato Neural Progenitor Cells (NPCs) In Vitro:

To develop a strategy for direct delivery of Cas9 RNPs into the brain in vivo, the Ai9/Ai14 tdTomato mouse model (hereafter referred to as tdTomato mouse) was first tested whether it could be adapted to "report" Cas9 editing in neural cells (Madisen et al. 2009. Nat. Neurosci. 13:133-140) (FIG. 10). These mice harbor a modification at the Rosa26 locus with a ubiquitously expressed CAGGS promoter and a loxP-flanked STOP cassette (three repeats of the SV40 polyA sequence) that prevents expression of the tdTomato fluorescent protein. Cre-mediated recombination at the loxP sites leads to STOP cassette deletion and tdTomato expression. This mouse model provides a robust, high-throughput, quantitative readout of site-specific genome modification at the loxP-flanked locus with a gain-of-function fluorescent signal in modified cells. One of the two loxP sites lacks a Protospacer Adjacent Motif (PAM) site necessary for Cas9-mediated DNA cleavage, and therefore, two unique single-guide RNAs (sgRNAs) would be needed for Cas9 to cut as Cre does at the loxP sites. Therefore it was set out to find a unique targetable sequence within the STOP cassette that is capable of activating the tdTomato reporter. To test this, E13.5 Neural Progenitor/Stem cells (NPCs) were isolated from the tdTomato mouse (FIG. 11). These cultures were nucleofected with plasmids encoding S. pyogenes Cas9 protein and various sgRNA's that targeted the STOP-cassette (FIG. 11). From this experiment a STOP cassette-targeting sgRNA, sgRNA298 was determined, hereafter referred to as sgRNAtdTom, that most efficiently activated the tdTomato reporter gene. A dose-dependent effect was observed corresponding to the amount of RNP that was introduced by nucleofection (FIG. 10B). Next generation sequence analysis (NGS) of the STOP cassette locus using primers 344F and 345R confirmed Cas9 RNP induced insertion/deletion (indel) mutations (FIG. 10D and FIG. 12) (Güell et al. 2014, Bioinformatics. 30:2968-2970).

FIG. 10A-10G. Cas9 RNP-Mediated Editing of Neural Progenitor/Stem Cells (NPCs).

Figure 10A:
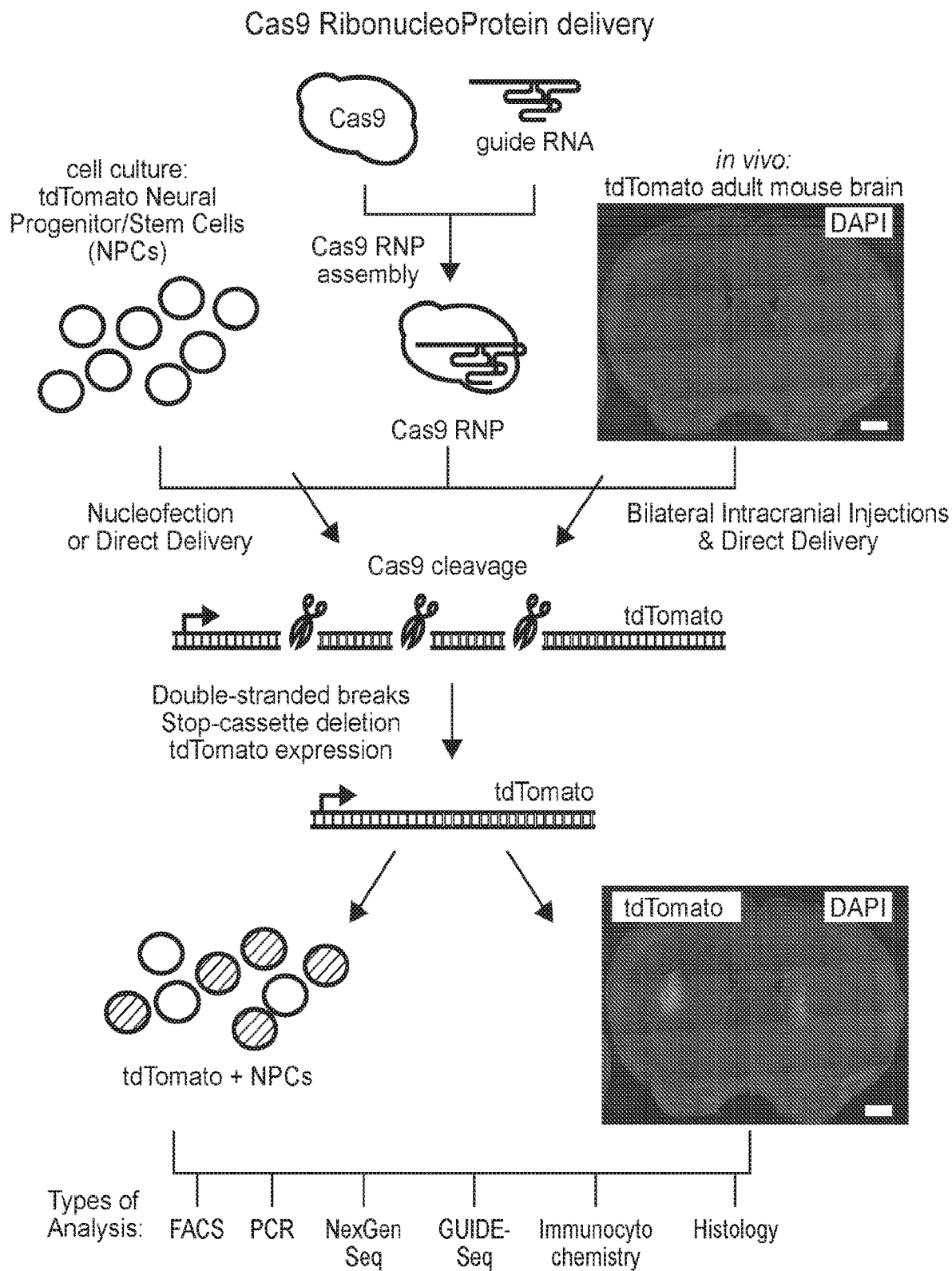
Figure 10D:
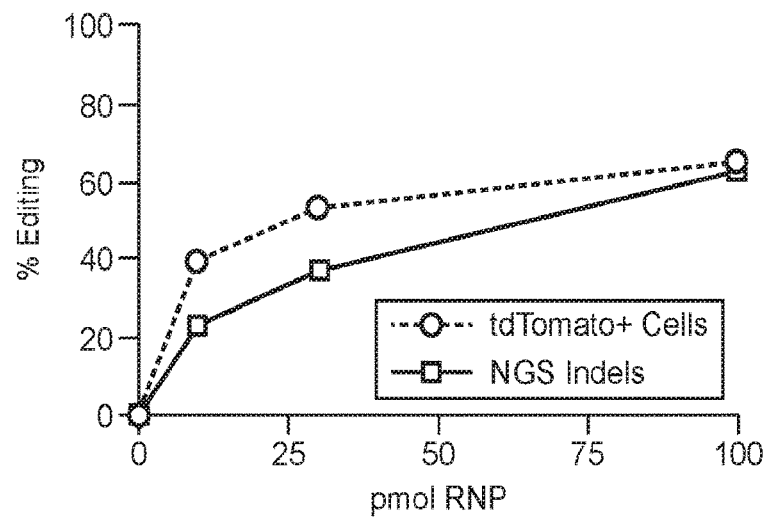
Figure 10E:
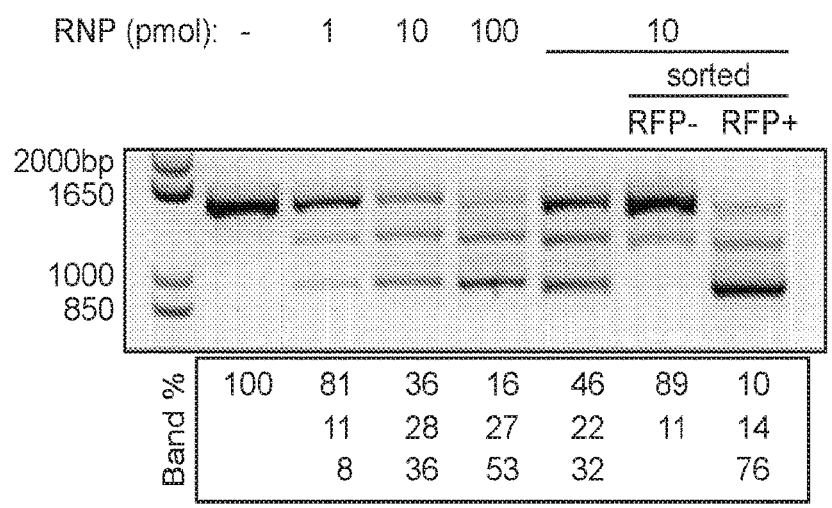
Figure 10F:
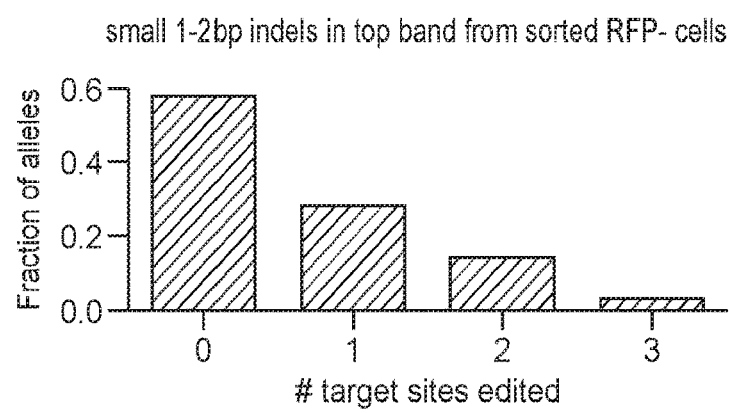
Figure 10G:
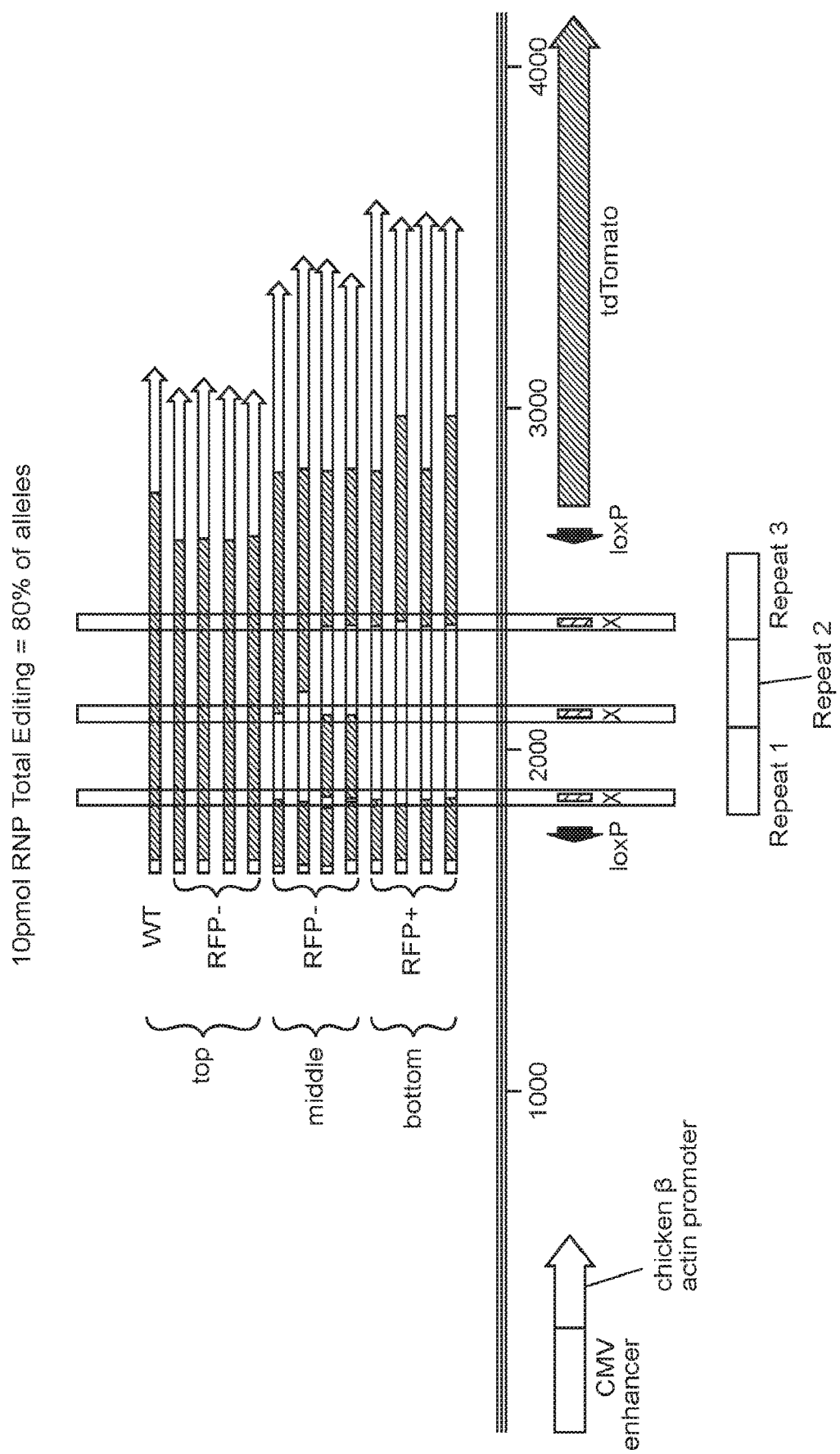

FIG. 10A) Experimental scheme of Cas9:single-guide RNA ribonucleoprotein (Cas9 RNP) complexes delivery to NPCs OR Intracranial injection into adult mouse brains for genome editing, followed by genetic and phenotypic characterization. Scale bar 1 mm. FIG. 10B) Images of NPC neurospheres with activated tdTomato RFP 3 days following nucleofection of 10, 30 and 100 pmol Cas9 RNP complexes into $2.5 \times 10^5$ cells. (10 pmol Cas9 RNP=$2.4 \times 10^7$ RNP molecules/cell) Scale bar 400 um. FIG. 10C) FACS Analysis of editing efficiency from FIG. 10B cultures. Representative data from n=3 biological replicates. FIG. 10D) Quantification of activation of tdTomato reporter by FACs and editing efficiency by Next Generation Sequencing in NPCs. n=3 biological replicates for FACS analysis. FIG. 10E) PCR analysis of edited STOP cassette 3 days post RNP nucleofection. Triple DNA ladder pattern at STOP cassette locus in edited cells; Top band=unedited or small 1-2 bp indels, middle band=single repeat deletion, bottom band=double repeat deletion pattern. These three observed bands correspond to the 6 expected products due to the shared sizes of some of the products. PCR analysis of FACS sorted RFP⁻ and RFP⁺ cells, indicates that only double repeat deletion/bottom band in STOP cassette activates tdTomato RFP. FIG. 10F) Sanger sequencing of 100 clones from the top band from 10 pmol RNP nucleofected, FACS sorted RFP⁻ NPCs. 45% of the bands are edited with small 1-2 bp indels at 1, 2 or 3 of the sgRNA298 target site indicated by "X" in FIG. 10G. FIG. 10G) Representative clones from Sanger sequencing of gel purified top, middle and bottom bands from 10 pmol RNP nucleofected NPCs.

FIG. 11A-11D.

Figure 11A:
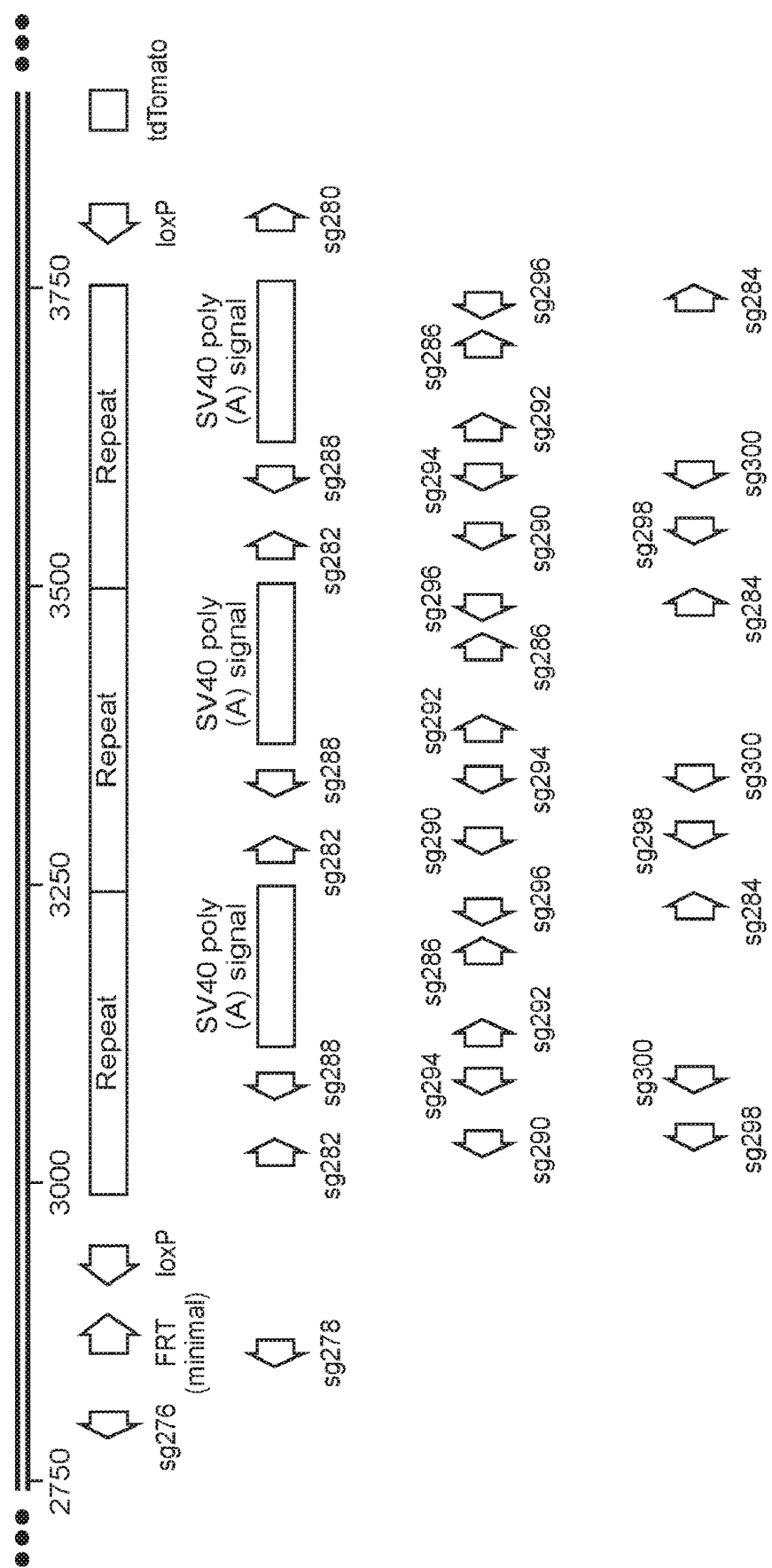

FIG. 11A) Location of sgRNA's on tdTomato STOP cassette. FIG. 11B) Cas9;sgRNA target sites differentially activate tdTomato reporter gene. sgRNA organized on histogram by 5'-3' position on tdTomato STOP cassette. FIG. 11C) Table of sgRNA sequences with Off-target hit scores (Hsu et al. 2013. Nat. Biotechnol. 31:827-832). FIG. 11D) Neural Progenitor Cell cultures are Nestin+, a neural progenitor/stem cell marker protein. Scale bar=100 um.

Figure 12:
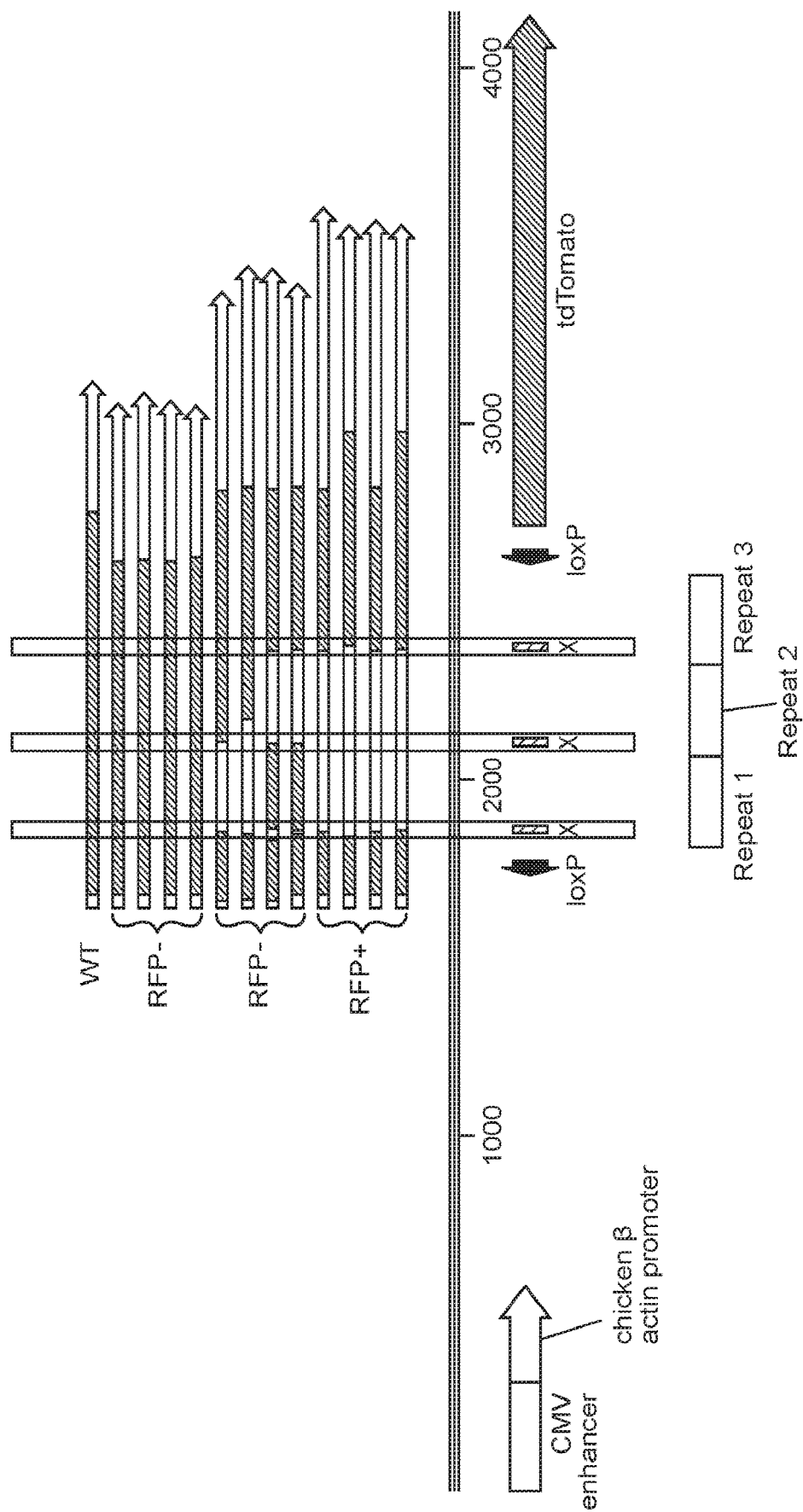
FIG. 12 depicts Cas9 RNP-mediated editing of Ai9 mouse tdTomato STOP cassette.

FIG. 12. Cas9 RNP-Mediated Editing of Ai9 Mouse tdTomato STOP Cassette.

Representative wild-type (WT) and edited alleles amplified from genomicDNA with primers 272Fd/273R. DNA bands were gel purified, cloned, Sanger sequenced and aligned to tdTomato STOP cassette.

sgRNAtdTom has three target sites in the STOP cassette and therefore can generate six types of edits, including three small indels that do not generate a deletion, two types of single-repeat deletions and one double-repeat deletion (FIG. 12). PCR analysis of the STOP cassette locus (272F and 273R primers) using genomic DNA from Cas9 RNP-treated cells revealed the expected three DNA band laddering pattern in edited cells (FIG. 10E). To determine which type of edits activate tdTomato expression fluorescence-activated cell sorting (FACS) was used to separate fluorescent (RFP$^+$) and non-fluorescent (RFP$^-$) cells within samples of 10 pmol RNP nucleofected NPCs in which 38% of the cells were RFP$^+$. PCR analysis showed that products corresponding to a double repeat deletion were only present in RFP$^+$ cells, whereas the single repeat deletion occurred in both RFP$^+$ and RFP$^-$ cell populations. Therefore, activation of tdTomato required double repeat deletion that removed two of three SV40 polyA repeat sequences, while single repeat deletions did not activate tdTomato. Sanger sequencing of 100 clones of the RFP FACS sorted cells revealed that 45% of these alleles contained small 1-2 bp indels that did not activate tdTomato expression (FIG. 10E). Based on these data, it was estimate that 80% of alleles in the 10 pmol RNP nucleofected samples were edited, with 38% of the alleles and thus cells acquiring the multiple edits necessary to activate tdTomato expression. These results show that the tdTomato reporter system can be harnessed for robust and positive visual detection of genome editing by CRISPR-Cas9, and could be useful for visualization of edited cells in vivo.

Enhanced Cell Penetration of Cas9 RNPs In Vitro:

Nucleofection of Cas9 RNP complexes is useful for treating cells in culture and isolated primary cells ex vivo. Recently electroporation has also been used to deliver Cas9 into muscle and retina with low efficiency. In some embodiments, editing CNS neurons in adult animals with high efficiency will require an alternative delivery strategy. Cas9 RNP has no innate cell penetrating activity, and its direct protein-based delivery into cells required chemical conjugation of poly-arginine peptides, a strategy prone to inefficiency and heterogeneity or mixing with lipid carrier molecules which are immunogenic, inflammatory and toxic. An alternative direct delivery approach was developed by engineering cell penetrating capabilities into Cas9 RNP complexes.

Figure 13A:
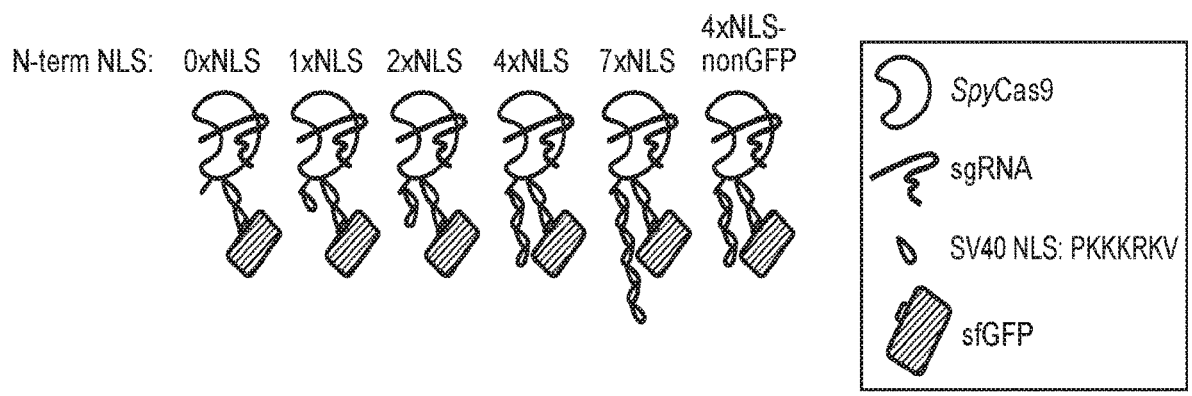
FIG. 13A-13D depict that direct delivery of cell penetrating Cas9 RNPs increases editing efficiency in vitro.
Figure 13B:
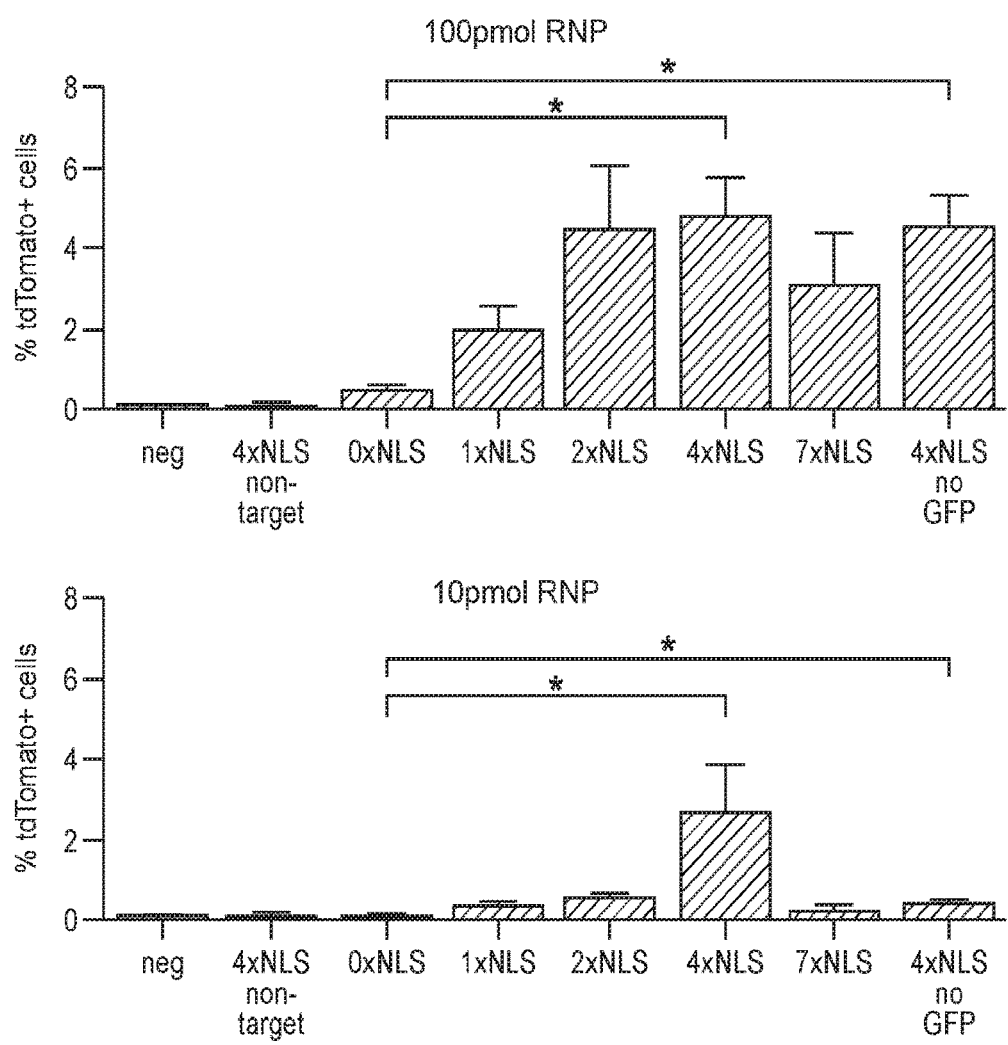
Figure 13C:
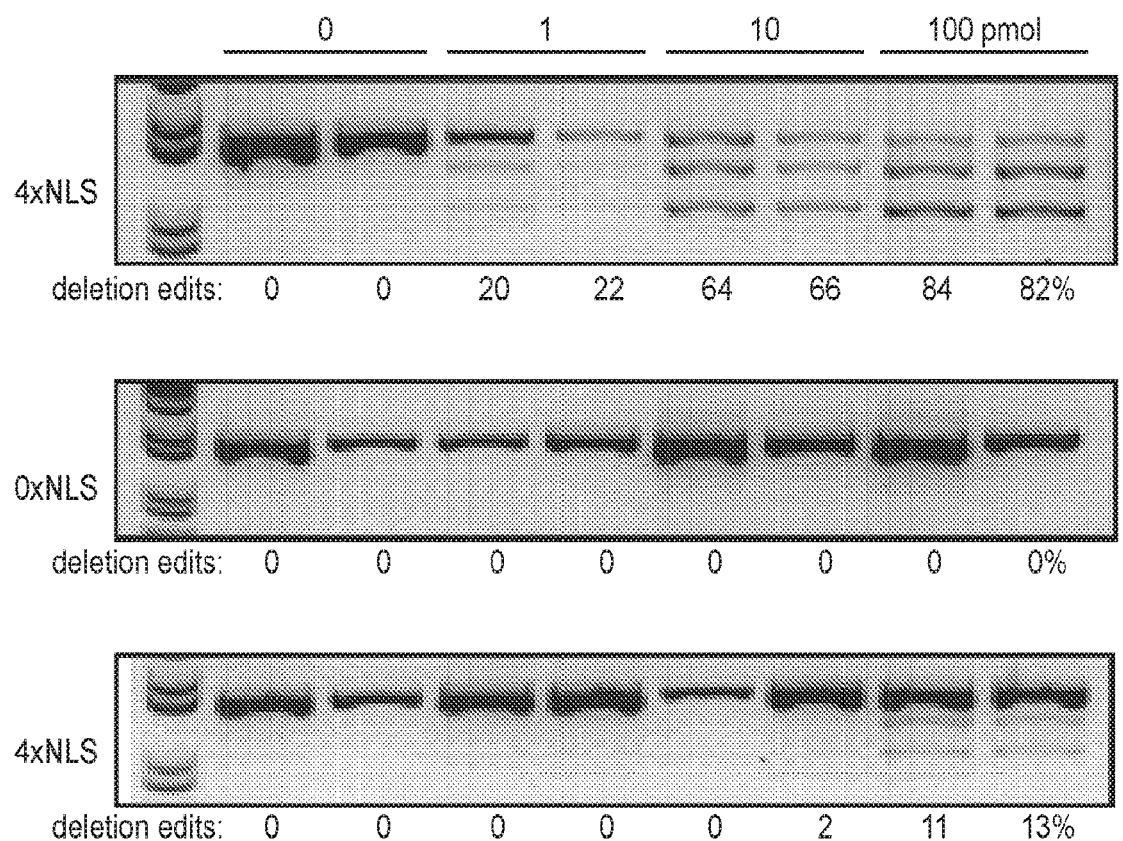

Arrays of Simian vacuolating virus 40 (SV40) nuclear localization sequences (NLSs) enhanced the innate cell penetrating capabilities of zinc finger nucleases (Liu J, Gaj T, Wallen M C, Barbas C F. 2015. Improved Cell-Penetrating Zinc-Finger Nuclease Proteins for Precision Genome Engineering. 1-9). Although the Cas9 protein that was used for cell-based experiments contains two SV40 NLS on the C-terminus, it was found that RNPs generated using this protein are not cell-penetrating. Therefore Cas9 proteins with increasing numbers of SV40 NLS arrays on the N-terminus were designed, expressed and purified. These N-terminal NLS-Cas9 fusions are referred to as 0×, 1×, 2×, 4× and 7×NLS-Cas9. These were made with and without superfolder(sf)GFP (Pédelacq et al. 2005, Nat. Biotechnol. 24:79-88) fused on the C-terminus of Cas9 (FIG. 13A). To test potential cell penetrating properties of these Cas9 variants, RNP complexes were prepared and added directly to the media of tdTomato NPC cultures. Site-specific genome editing was monitored by observing activation of tdTomato reporter expression after three days of cell outgrowth. Editing efficiency increased for each RNP sample up to 4×NLS-Cas9 and then decreased for the 7×NLS-Cas9. TdTomato activation levels increased markedly as the number of NLS sequences on Cas9 was increased from none to 4 copies; at 100 pmol RNP, <0.5% tdTomato$^+$ cells was observed for 0×NLS-Cas9 vs. 5% for 4×NLS-Cas9 and at 10 pmol RNP; 0% for 0×NLS-Cas9 vs. 2.5% for 4×NLS-Cas9 (FIG. 13B). TdTomato expression was not detected in control experiments using a non-targeting sgRNA (target sequence is GALA) indicating that genome editing is sequence specific. PCR analysis of the tdTomato locus in these cells confirmed the expected deletion edits and, showed higher total deletion efficiency than reported by tdTomato fluorescent protein expression; at 100 pmol RNP, 0×NLS-Cas9 was below detection levels vs. 4×NLS-Cas9 which yielded 12% total deletion efficiency (FIG. 13C).

FIG. 13A-13D. Direct Delivery of Cell Penetrating Cas9 RNPs Increases Editing Efficiency In Vitro.

Figure 13D:
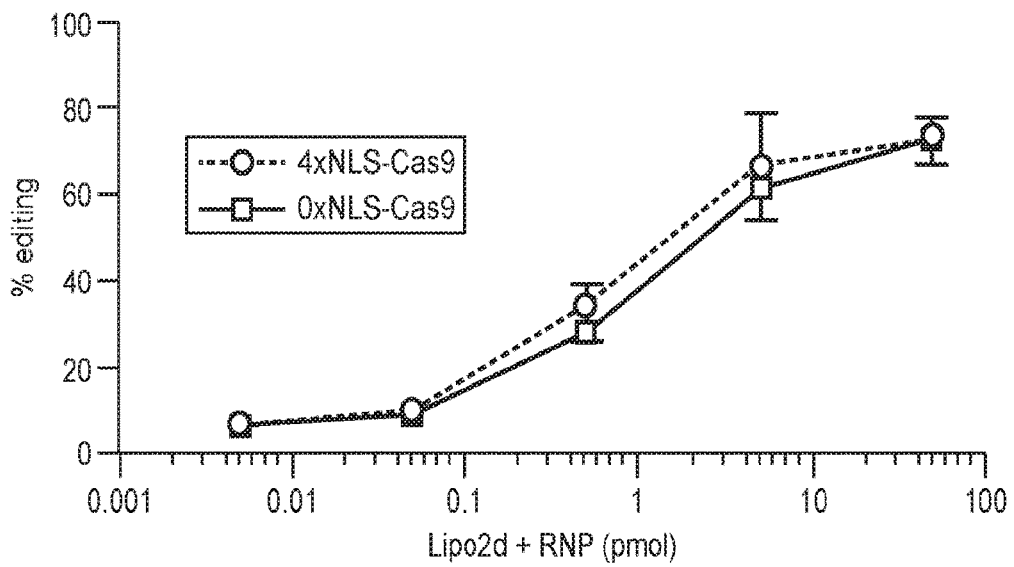

FIG. 13A) 1-7×N-terminal NLS-Cas9 design; (SV40 nuclear localization sequence a.a. PKKKRKV—SEQ ID NO:1090) FIG. 13B) Direct incubation of 1-7×NLS-Cas9 in NPCs led to expression of tdTomato in genome-edited NPC cells. 4×NLS-Cas9 design is significantly more efficient at genome-editing cells than other designs. Data are represented as mean±SEM (100 pmol 0×NLS vs. 4×NLS; Two-tailed Unpaired t test with Welch's correction; p=0.0126 and $F_{4,2}$=109. 100 pmol 0×NLS vs. 4×NLS-noGFP; Two-tailed Unpaired t test with Welch's correction; p=0.0057 and $F_{4,\ 2}$=63.69. 10 pmol 0×NLS vs. 2×NLS; Two-tailed Unpaired t test with equal SD; p=0.0096 and $F_{2,\ 2}$=2.597. 10 pmol 0×NLS vs. 4×NLS-noGFP; Two-tailed Unpaired t test with equal SD; p=0.0462 and $F_{3,\ 2}$=4.072) n=3 biological replicates with 2 technical replicates each. FIG. 13C) PCR of STOP cassette locus validates tdTomato reporter FACS analysis. Cas9-RNP nucleofection efficiency compared with direct-delivery efficiency. 4×NLS-Cas9 RNP complexes yield deletion edits (lower 2 bands) while 0×NLS-Cas9 RNP complexes do not. Direct delivery RNP was added to media and incubated with cells for 24 hours, then cells were washed 2× with 200 U/ml Heparin in DMEM media and allowed to grow for 24 additional hours. Representative gel from n=3 biological replicates with 2 technical replicates each. FIG. 13D) Cas9 RNP complexes targeting d2EGFP are mixed with Lipofectamine2000 and delivered to HEK293T-d2EGFP cells. Percent editing is measured by EGFP gene disruption by FACS analysis. No significant difference in editing efficiency. Data are represented as mean±SD (4×NLS-Cas9;sgRNA-NT3 vs. 0×NLS-Cas9;sgRNA-NT3; Two-tailed Unpaired t test with equal SD; p=0.9032 and $F_{,\ 5}$=1.034). n=3 biological replicates with 3 technical replicates each.

To assess if there was a difference in DNA targeting activity of 0×NLS-Cas9 versus 4×NLS-Cas9 RNP complexes, the cell-penetration step was bypassed by mixing the RNPs with Lipofectamine2000 to trigger delivery into the cytoplasm by cell membrane fusion (Zuris J A, Thompson D B, Shu Y, Guilinger J P, Bessen J L, Hu J H, Maeder M L, Joung J K, Chen Z-Y, Liu D R. 2014. Cationic lipid-mediated delivery of proteins enables efficient protein-based genome editing in vitro and in vivo. Nat Biotechnol.). Since lipofectamine-based RNP delivery into NPCs is inefficient, readily-transfectable cultured human embryonic kidney (HEK293) was used for this experiment. When Cas9 RNPs targeting EGFP (Chen et al. 2013, Cell. 155:1479-1491) were delivered into HEK293-d2EGFP cells using lipofectamine, the editing activity of the 0×NLS-Cas9 and 4×NLS-Cas9 were not significantly different (FIG. 13D). These data may suggest that once inside the cytoplasm, both 0×NLS-Cas9 and 4×NLS-Cas9 RNPs can find and cleave target DNA in the nucleus with equal efficiency. An NLS is not required on Cas9 for genome editing as long as cells are cultured for sufficient time to allow cell divisions, during which the nuclear envelope breaks down. Both these Cas9's have 2×NLS on the C-terminus. Therefore the difference observed in editing efficiency between 0×NLS-Cas9 and 4×NLS-Cas9 RNP complexes in the direct delivery experiment is likely to result from differences in cell penetrating ability rather than differing efficiencies of nuclear localization or target DNA cleavage.

In Vivo Delivery of Cas9 RNPs into Neurons of the Adult Brain:

With the knowledge that the N-terminal 4×NLS sequence array increased significantly the direct delivery of Cas9 RNP complexes in NPC cultures, experiments were designed to test the gene-modification capabilities of these RNP complexes in adult mouse brains. An intracranial injection system was set up using the tdTomato mouse that, as in the cell culture experiments, reports gene editing by activating expression of tdTomato fluorescent protein. To test Cas9 RNP activity in diverse neuronal subtypes, four brain regions were targeted: the hippocampus, the dorsal striatum, the primary somatosensory cortex (S1) and the primary visual cortex (V1) (FIG. 14A). In initial experiments, an RNP dose of 4 pmol/0.5 µL was used for stereotaxic injection. Brains were analyzed 12-14 days post-injection to allow time for the tdTomato protein to be expressed and accumulate in genome-edited cells.

Figure 14C:
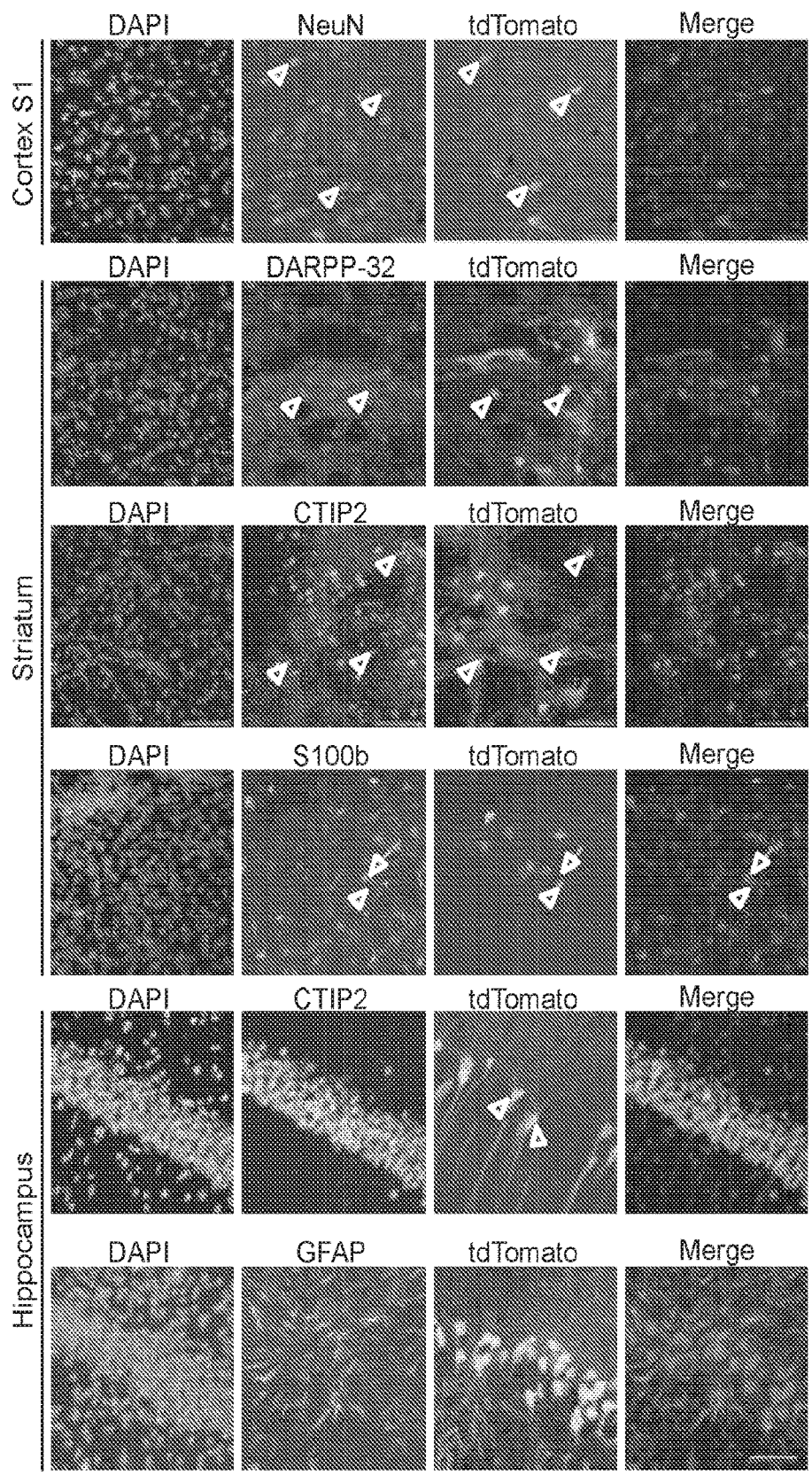

FIG. 14A-14C. Injection of Cas9 RNP into Multiple Brain Regions in Adult Mice Results in Precise and Programmable Genome-Editing.

FIG. 14A) Dots indicate stereotaxic injection sites on coronal cartoons of mouse brain. Single injection of 4 pmol Cas9 RNP in 0.5 ul volume was injected into 1 of 4 injection sites: HC=Hippocampus, S=Striatum, CTX S1=Primary Somatosensory Complex (S1), CTX V1=Primary Visual Cortex V1. Male mice are 14-15 weeks old. Brains are analyzed 12-14 days post injection. 50 um thick floating sections, 1 section every 300 um analyzed. Cas9 RNP components are: 0×NLS-Cas9-2×NLS-sfGFP or 4×NLS-Cas9-2×NLS-sfGFP. sgRNAtdTom (targets STOP cassette in tdTomato locus), sgRNA non-targeting (targets Gal4 sequence not present in mouse genome). FIG. 14B) Quantification of genome-edited tdTomat+ cells/pmol RNP delivered (Cas9 construct; sgRNA). 4×NLS-Cas9 RNP complexes are significantly more efficient compared to 0×NLS-Cas9 RNP complexes for in vivo genome-editing in all brain regions tested. Sham (injection buffer only) and 4×NLS-Cas9; non-targeting RNP complexes do not activate tdTomato indicating specificity of genome editing with Cas9 RNP complexes. Data are represented as mean±SEM (4×NLS;tdTom vs. 0×NLS;tdTom; Two-tailed Unpaired t test with equal SD; p=0.002 and $F_{5,5}$=5.9 for the striatum. Two-tailed Unpaired t test with Welch's correction p=0.03 and $F_{5,5}$=215 for Cortex S1. p=0.03 and $F_{5,5}$=25 for Cortex V1. p=0.04 and $F_{5,5}$=83 for the hippocampus.) The sample size for each group is as follows: Sham (buffer only injections): n=4 (2 biological replicates with 2 technical replicates each), 4×NLS;non-targeting sgRNA: n=4 (2 biological replicates with 2 technical replicates each), 0×NLS;tdTom sgRNA: n=6 (3 biological replicates with 2 technical replicates each), 4×NLS;tdTom sgRNA: n=6 (3 biological replicates with 2 technical replicates each). FIG. 14C) Representative pictures of brain sections with genome-edited cells expressing tdTomato and antibody staining against various marker proteins. Antibody staining of brain sections from 4×NLS-Cas9 RNP treated animals shows editing in neurons and not astrocytes. Confocal microscopy images used for qualitative analysis of tdTomato+ co-localization with marker proteins to identify edited cells. NeuN, a neuronal specific nuclear protein in vertebrates. CTIP2, aka BCL11a, a transcription factor present in CA1 hippocampus and striatum neurons. DARPP-32, cAMP-regulated neuronal phosphoprotein, a marker of striatum medium spiny neurons. GFAP, glial fibrillary acidic protein is an intermediate filament (IF) protein that is expressed by astrocytes and ependymal cells of the CNS. S100β, a gene highly expressed in striatal astrocytes. Scale bar is 50 µm.

In vivo editing was observed for both the 0× and 4×NLS-Cas9 RNP complexes that targeted tdTomato, but not for RNPs containing a non-targeting sgRNA. Similar to results in cultured cells, the 4×NLS-Cas9 RNP was 10-fold more efficient at editing cells in the brain compared to the 0×NLS-Cas9 RNP in all four brain regions tested as assessed by counting RFP+ cells in serial sections from the primary somatosensory cortex (S1), the primary visual cortex (V1), the hippocampus, and the dorsal striatum (FIG. 14B). Notably, in the 4×NLS-Cas9 treatment the occurrence of tdTomato+ cells extended ~1 mm3 from the injection site (FIG. 15). Therefore, the 4×NLS-Cas9 RNP complexes were significantly more efficient at editing cells in the adult brain than the 0×NLS-Cas9 RNP complexes.

Figure 15A:
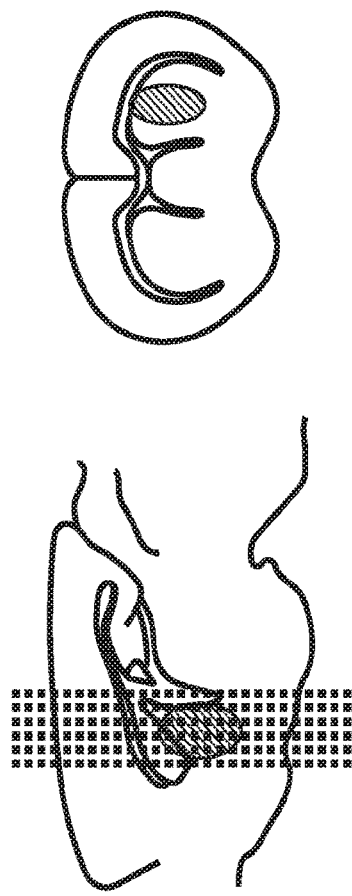
FIG. 15A-15C depict that bilateral intrastriatal injection measurements of tdTomato+ cell volume and density indicates RNP dose dependent increase in edited tissue volume.
Figure 15B:
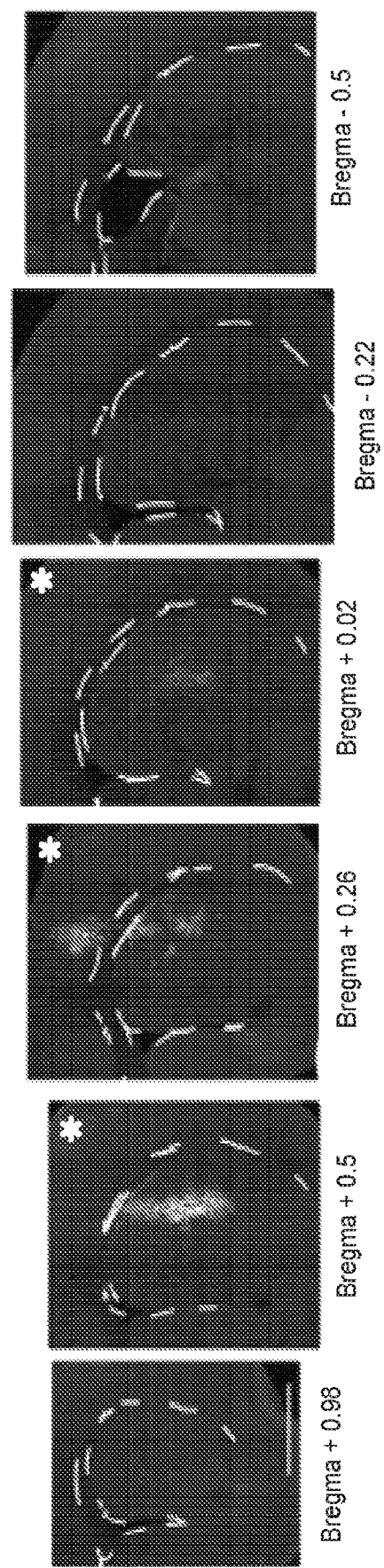
Figure 15C:
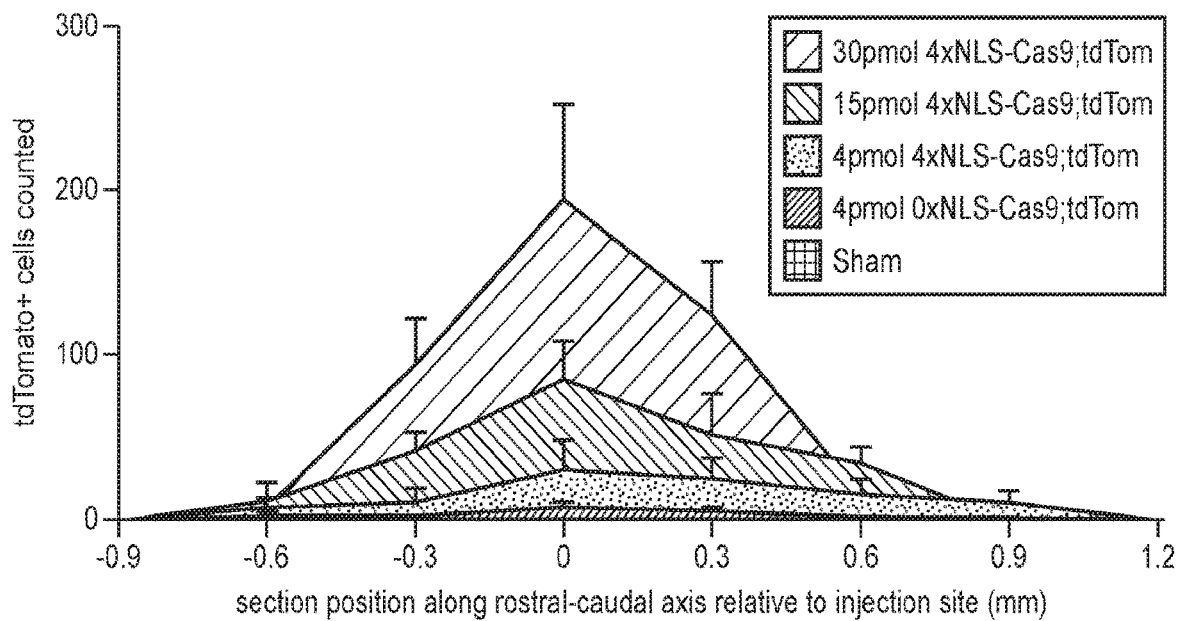

FIG. 15A-15C. Bilateral Intrastriatal Injection Measurements of tdTomato+ Cell Volume and Density Indicates RNP Dose Dependent Increase in Edited Tissue Volume.

FIG. 15A) Shaded oval indicates region of tdTomato+ cells on sagittal and coronal cartoons of mouse brain. Dashed lines on sagittal section represent approximate positions of 50 m coronal sections along the rostral-caudal axis. FIG. 15B) Representative images of serial coronal sections from a 30 pmol 4×NLS-Cas9 injected striatum are presented here with approximate Bregma positions. With serial sectioning at the periodicity of 1 in 6, each coronal section represented here samples 300 m of tissue making the volume of edited cells 1.5 mm3. Asterisks (*) indicate position of tissue sections used for LASER microdissection of tdTomato+ dorsal striatal tissue. Scale bar=1.4 mm. FIG. 15C) Area representation with # of tdTomato+ cells on Y axis and rostral-caudal position of coronal sections analyzed on X axis. X axis units are millimeters (mm). 4 pmol 0×NLS-Cas9 RNP edits fewer cells and extends for ~1 mm on rostral-caudal axis. Density and volume of tdTomato+ cells along rostral-caudal axis increases with increasing dose of 4×NLS-Cas9. n=6 for each group comprising 3 biological replicates with 2 technical replicates each. Data are represented as mean±SEM.

Dual color immunofluorescence was performed to identify the specific cell-types that are edited upon Cas9 RNP injection. In the cortex, tdTomato+ cells were also positive for the post-mitotic neuronal marker, NeuN (FIG. 14C). In the hippocampus, the edited tdTomato+ cells co-localized with the post-mitotic marker, CTIP2 (also known as BCL11a), a transcription factor present in CA1 hippocampus and striatal neurons. In the hippocampus co-localization of tdTomato+ cells was not observed with GFAP, an astrocyte marker. In the striatum, editing of medium spiny neurons was identified by co-localization of tdTomat+ cells with CTIP2 and DARPP-32 (cAMP-regulated neuronal phosphoprotein), a well-documented marker of striatal medium spiny neurons. As in the hippocampus, genome editing was not detected in astrocytes because there was no colocalization between tdTomato+ cells and GFAP nor S100β, both astrocyte marker proteins.

To assess possible immunogenicity of Cas9 RNP complexes injected into the brain, microglia were analyzed by staining for the marker protein IBA-1 (ionized calcium-binding adapter molecule 1, also known as Allograft inflammatory factor 1 (AIF-1)). IBA-1 is useful as an indicator of activated microglia because 1) its levels increase and 2) the cytoplasmic staining pattern can be used to assess microglia morphological changes that occur upon activation, namely close association with neuron cell bodies (Chen Z. et al. 1AD. Microglial displacement of inhibitory synapses provides neuroprotection in the adult brain. Nature Communications 5: 1-12). Significant IBA-1 intensity differences or morphological differences were not observed between control and RNP injected brains (FIG. 16). Taken together, the cellular analysis revealed Cas9 RNP mediated editing in diverse neuronal subtypes in the cortex, hippocampus and the dorsal striatum and no evidence of a microglia-mediated innate immune response following Cas9 RNP injection.

Figure 16A:
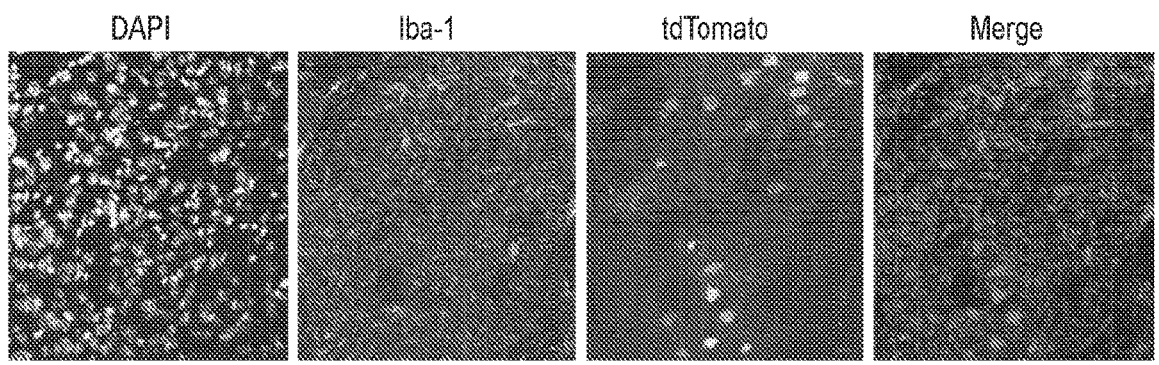
FIG. 16A-16B depict the analysis of innate immune response in treated and untreated brains.
Figure 16B:
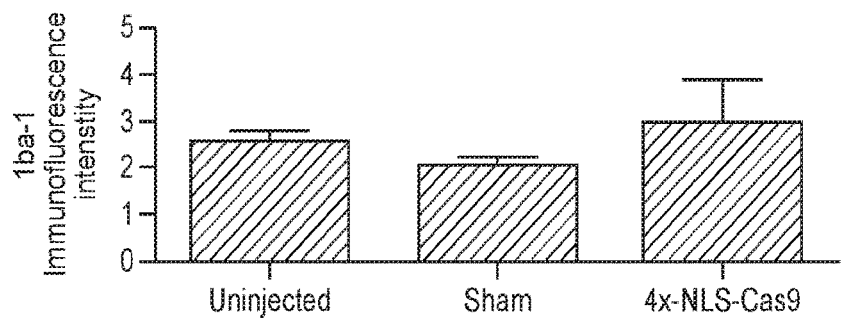

FIG. 16A-16B. Analysis of Innate Immune Response in Treated and Untreated Brains.

FIG. 16A) Morphological appearance of microglia in the mouse brain in Csa9 RNP complex treated and untreated mice (visualized in green by immunostaining with anti-IBA-1 antibody). Cas9 RNP treated mice, microglia have small cell bodies and long and slender processes indicating they are not activated. When activated, microglia enlarge their cell bodies and thicken their processes, which closely enwrap neuronal cell bodies. FIG. 16B) Quantification of IBA-1 protein intensity in control and 4×-NLS Cas9 treated mice. Data are represented as mean±SEM (One way ANOVA; p=0.4496 and F2, 7=0.898). n=3 animals per condition with 2-8 cells analyzed per animal. The experimenter was blinded to treatment condition while performing quantitation of fluorescence intensity.

To investigate whether an increased dose of 4×NLS-Cas9 RNP complexes in the dorsal striatum would improve genome editing efficiency an intrastriatal injection dose course of 4, 15 and 30 pmol/0.5 μl injections was performed (FIG. 17A). RNP was prepared at 8 μM, 30 μM and 60 μM concentrations and injected into the dorsal striatum. Brains were harvested 14 days later, sectioned, DAPI counterstained, and tdTomato+ cells counted. An RNP dose dependency on total number of edited cells/injection was observed, 4 pmol (588±90), 15 pmol (1339±331), 30 pmol (2675±613) (FIG. 17B. 17C). It was noted that at the highest amount of RNP injected (30 pmol 4×NLS-Cas9 RNP), a 3-fold larger volume of tissue was edited compared to that observed using the lowest (4 pmol) RNP amount (~1.5 mm³ vs. ~1 mm³ of edited tissue; FIG. 15). Since the same injection volume was used in each case, this result hints at a volume independent mechanism of RNP spreading through the interstitial space. Also observed was an increased density of edited cells in tissue receiving the highest amount of Cas9 RNP as detected by counting tdTomato+ cells from tissue sections spaced every 300 μm along the rostral-caudal axis (FIG. 15). The efficiency of 4×NLS-Cas9 RNP-mediated genome editing was ~100 tdTomato+ cells per pmol of RNP delivered and was not significantly different across the three RNP doses in the intrastriatal injection experiments (FIG. 17D).

FIG. 17A-17F. Increasing Dose of 4×NLS-Cas9 RNP Complexes Significantly Increases the Number of tdTomato+ Genome-Edited Cells in the Striatum.

FIG. 17A) Dots indicate bilateral stereotaxic injection sites on coronal cartoon of mouse brain. Coronal section mosaic tile image of bilateral 30 pmol RNP injections with tdTomato+ signal reporting precise editing in the striatum. Blue=DAPI staining nuclei, Red=endogenous tdTomato expression. FIG. 17B) tdTomato+ cells in single injection dose response: 4, 15, 30 pmol/0.5 μl injection. Confocal images of region of edited striatum tissue. Scale bar 100 um. FIG. 17C) Quantification of total #tdTomato+ edited striatal cells per injection site. Data are represented as mean±SEM (p=0.0022; Kruskal-Wallis test; Two-tailed Unpaired t test with Welch's correction p=0.018 and $F_{5, 5}$=46.03 for 4 pmol v. 30 pmol. p=0.0736 and $F_{5, 5}$=13.43 for 4 pmol v. 15 pmol. Two-tailed Unpaired t test with equal SD; p=0.0845 and $F_{5, 5}$=3.428 for 15 pmol v. 30 pmol. n=6 for each group comprising 3 biological replicates with 2 technical replicates each). FIG. 17D) Quantification of tdTomato+ cells per pmol RNP delivered (1 edited cell/10 fmol RNP). Data are represented as mean±SEM (p=0.213; Kruskal-Wallis test. n=6 for each group comprising 3 biological replicates with 2 technical replicates each). FIG. 17E) PCR analysis of gDNA isolated by LASER microdissection of 30 pmol RNP treated dorsal striatum. Tissue from three 50 μm sections, marked with an asterisk in FIG. 15, taken at 300 μm intervals spanning ~1 mm on the rostral-caudal axis of tdTomato+ dorsal striatum were used. ~1 mm×1.5 mm rectangles of tissue containing tdTomato+ cells were microdissected and pooled. PCR analysis confirmed the expected genomic deletions in 7.5% of the alleles (FIG. 17D). n=6 for each group comprising 3 biological replicates with 2 technical replicates each. FIG. 17F) Sanger sequencing of 88 clones isolated from top DNA band in FIG. 17E reveals 8.8% of alleles have small 1-2 bp indels at 1, 2, or 3 target sites.

To quantify the efficiency of allele editing in the 30 pmol 4×NLS-Cas9 RNP treated animals LASER microdissection of tdTomato+ dorsal striatum tissue was performed. Three 50 μm thick sections spanning ~1 mm along rostral-caudal axis were used (marked with asterisk in FIG. 15). ~1 mm×1.5 mm rectangles of tissue containing tdTomato+ cells were microdissected and pooled. Genomic DNA was isolated from this tissue and PCR analysis confirmed the expected genomic deletions in 7.5% of the alleles (FIG. 17D). Sanger sequencing of the top band PCR product (corresponding in size to wild-type and small 1-2 bp indel editing events, revealed an additional 7.5% of alleles with small 1-2 bp indels as was observed for tdTomato mouse NPCs edited in vitro.

Cas9 RNP based systems have been shown to have significantly decreased off-target editing potential compared to genetically encoded systems. GUIDE-Seq technique was used to search for bona fide 0× and 4×NLS-Cas9 RNP on and off-target sites. Because chromatin structure influences Cas9 targeting, GUIDE-Seq was performed in primary cortical neuron cultures isolated from post-natal day 0 (P0) tdTomato mice and nucleofected with 0× and 4×NLS-Cas9 RNPs. The target site was identified and no off-target editing was observed. Also no difference in fidelity of targeting was observed between the 0× and 4×NLS-Cas9 RNPs (FIG. 18).

FIG. 18. GUIDE-Seq Analysis for Off-Target Editing and 0×NLS-Cas9 vs. 4×NLS-Cas9 Fidelity.

GUIDE-Seq (Tsai et al. 2014, Nat. Biotechnol. 33:187-197) analysis in Ai9 tdTomato primary cortical neuron cultures isolated at postnatal day 0 brains and nucleofected with 0×NLS or 4×NLS-Cas9 RNPs complex with sgRNAtd- Tom or sgRNA-nontargeting. Target site edits were identified but no off-target editing was observed. No difference in fidelity of targeting was observed between the 0× and 4×NLS-Cas9 RNPs.

GUIDE-seq analysis was carried out for the eight different samples described in FIG. 18. Sites that were present in both the sgRNA_tdTomato targeted cells and the sgRNA_Gal4 targeted cells were ignored, leaving only the tdTomato site.

Gal4 target sequence—SEQ ID NO:1333 and tdTomato target sequence—SEQ ID NO:1332. Analysis #1: "JDBS_1minus_S1_L001_R1_001_iden": Sequences were—SEQ ID NO:1335, 1335, 1336, 1337, 1338, 1339, 1340, 1341, 1342, 1343, 1344, 1345, 1346, 1347, 1348, 1349, 1350, 1351, 1352, 1353, 1354, 1355, 1355, 1356; Off-target sequences—SEQ ID NO:1357; and Target sequences—SEQ ID NO:1332. Analysis #2: "JDBS_1plus_S5_L001_R1_001_ident": Sequences were—SEQ ID NO:1358, 1359, 1360, 1361, 1362, 1363, 1364, 1365, 1366, 1367, 1368, 1369, 1370, 1371, 1347, 1372, 1373, 1374, 1375, 1376, 1377, 1378, 1379, 1380, 1381, 1382; Off-target sequences—SEQ ID NO:1357; and Target sequences—SEQ ID NO:1332. Analysis #3: "JDBS_2minus_S2_L001_R1_001_iden": Sequences were—SEQ ID NO:1383, 1384, 1385, 1386, 1387, 1388, 1389, 1390, 1363, 1391, 1392, 1393, 1394, 1347, 1347, 1347, 1395, 1396, 1397, 1398, 1399, 1400, 1401, 1402, 1403, 1404; Off-target sequences—SEQ ID NO:1357; and Target sequences—SEQ ID NO:1332. Analysis #4: "JDBS_2plus_S6_L001_R1_001_ident": Sequences were—SEQ ID NO:1405, 1406, 1407, 1358, 1408, 1409, 1410, 1411, 1412, 1413, 1414, 1347, 1371, 1347, 1415, 1416, 1398, 1400, 1417; Off-target sequences—SEQ ID NO:1357; and Target sequences—SEQ ID NO:1332. Analysis #5: "JDBS_3minus_S3_L001_R1_001_iden": Sequences were—SEQ ID NO:1418, 1419, 1420, 1421, 1422, 1389, 1423, 1424, 1425, 1391, 1426, 1427, 1428, 1429, 1430, 1431, 1432, 1433, 1434, 1435, 1436, 1437, 1438, 1439, 1440, 1441; and Target sequence—SEQ ID NO:1333. Analysis #6: "JDBS_3plus_S7_L001_R1_001_ident": Sequences were—SEQ ID NO:1442, 1443, 1444, 1445, 1446, 1447, 1448, 1449, 1340, 1450, 1451, 1452, 1391, 1453, 1454, 1416, 1351, 1455, 1456, 1457, 1458, 1380, 1459, 1460, 1461, 1462; and Target sequence-SEQ ID NO:1333. Analysis #7: "JDBS_4minus_S4_L001_R1_001_iden": Sequences were—SEQ ID NO:1463, 1464, 1465, 1466, 1423, 1467, 1468, 1367, 1469, 1380, 1374, 1470, 1471, 1472, 1473, 1379, 1458, 1474, 1475; and Target sequence—SEQ ID NO:1333. Analysis #8: "JDBS_4plus_S8_L001_R1_001_ident": Sequences were—SEQ ID NO:1476, 1477, 1478, 1479, 1480, 1481, 1339, 1363, 1482, 1365, 1483, 1387, 1484, 1419, 1485, 1486, 1349, 1487, 1488, 1489; and Target sequence—SEQ ID NO:1333.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11118194B2). An electronic copy of the "Sequence Listing" will also be available from the USPTO upon request and payment of the fee set forth in 37 CFR 1.19(b)(3).

What is claimed is:

1. A ribonucleoprotein (RNP) complex comprising:
    a) a fusion type II CRISPR/Cas polypeptide comprising, in order from N-terminus to C-terminus:
        i) two to six heterologous polypeptides that facilitate uptake of the RNP complex into a eukaryotic cell;
        ii) a type II CRISPR/Cas polypeptide; and
        iii) one or two heterologous polypeptides that facilitate uptake of the RNP complex into a eukaryotic cell; and
    b) a guide RNA.

2. The RNP complex of claim 1, wherein the type II CRISPR/Cas polypeptide is a Cas9 polypeptide that is:
    i) enzymatically active; or
    ii) a nickase; or
    iii) enzymatically inactive but retains target nucleic acid binding activity.

3. The RNP complex of claim 1, wherein the guide RNA is a single-molecule guide RNA or a dual-molecule guide RNA.

4. The RNP complex of claim 1, wherein the heterologous polypeptides that facilitate uptake of the RNP into a eukaryotic cell comprise an amino acid sequence having at least 40% lysine or arginine or an amino acid sequence of the formula K(K/R)X(K/R), where X is any amino acid.

5. The RNP complex of claim 1, wherein the heterologous polypeptides that facilitate uptake of the RNP complex into a eukaryotic cell comprise an amino acid sequence of the formula K(K/R)X(K/R), where X is any amino acid.

6. The RNP complex of claim 4, wherein the heterologous polypeptides that facilitate uptake of the RNP complex into a eukaryotic cell comprise the amino acid sequence PKKKRKV.

7. The RNP complex of claim 1, wherein the fusion type II CRISPR/Cas polypeptide comprises, in order from N-terminus to C-terminus:
    i) four heterologous polypeptides that facilitate uptake of the RNP complex into a eukaryotic cell;
    ii) a type II CRISPR/Cas site-directed DNA-modifying polypeptide; and
    iii) two heterologous polypeptides that facilitate uptake of the RNP complex into a eukaryotic cell.

8. The RNP complex of clai1m 1, wherein the two to six heterologous polypeptides that facilitate uptake of the RNP complex into a eukaryotic cell comprise the same amino acid sequence and have the same length.

9. The RNP complex of claim 1, wherein the two to six heterologous polypeptides that facilitate uptake of the RNP complex into a eukaryotic cell differ from one another in amino acid sequence and/or length.

10. A method of binding a target nucleic acid in a eukaryotic cell, the method comprising:
    contacting a eukaryotic cell comprising a target nucleic acid with the complex of claim 1, wherein the complex enters the cell, and wherein the guide RNA and the fusion class type II CRISPR/Cas polypeptide bind to the target nucleic acid in the cell.

11. The method of claim 10, wherein the fusion type II CRISPR/Cas polypeptide:
    i) modulates transcription from the target nucleic acid; or
    ii) modifies the target nucleic acid; or
    iii) cleaves the target nucleic acid.

12. A method of genetically modifying a eukaryotic target cell, the method comprising contacting the eukaryotic target cell with the complex of claim 1.

13. The RNP complex of claim 1, wherein each of the two to six heterologous polypeptides that facilitate uptake of the RNP complex into a eukaryotic cell has a length of from 5 amino acids to 10 amino acids.

* * * * *

UNITED STATES PATENT AND TRADEMARK OFFICE
CERTIFICATE OF CORRECTION

| | | |
|---|---|---|
| PATENT NO. | : 11,118,194 B2 | Page 1 of 1 |
| APPLICATION NO. | : 16/061291 | |
| DATED | : September 14, 2021 | |
| INVENTOR(S) | : Jennifer A. Doudna et al. | |

It is certified that error appears in the above-identified patent and that said Letters Patent is hereby corrected as shown below:

On the Title Page

Item (73) Assignee: it should read as:
The Regents of the University of California, Oakland, CA (US);
F. Hoffmann-La Roche AG, Basel (CH);

In the Specification

In Column 50, Line 24, please replace "CTI TT" with --- CTT TTT ---;

In Column 58, Line 66, please replace "tdTomat+" with --- tdTomato+ ---;

In the Claims

In Column 62, Claim 8, Line 66, please replace "clai1m 1" with --- claim 1 ---; and In Column 63, Claim 10, Line 12, please delete the word "class".

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*